US008841305B2

(12) United States Patent
Thomas et al.

(10) Patent No.: US 8,841,305 B2
(45) Date of Patent: Sep. 23, 2014

(54) ACTIVATORS OF THE HUMAN PYRUVATE KINASE M2 RECEPTOR

(75) Inventors: Craig J. Thomas, Gaithersburg, MD (US); Douglas S. Auld, Potomac, MD (US); James Inglese, Bethesda, MD (US); Amanda P. Skoumbourdis, Langhorne, PA (US); Jian-Kang Jiang, Columbia, MD (US); Matthew B. Boxer, Point of Rocks, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/123,297

(22) PCT Filed: Oct. 9, 2009

(86) PCT No.: PCT/US2009/060237
§ 371 (c)(1),
(2), (4) Date: Apr. 25, 2011

(87) PCT Pub. No.: WO2010/042867
PCT Pub. Date: Apr. 15, 2010

(65) Prior Publication Data
US 2011/0195958 A1 Aug. 11, 2011

Related U.S. Application Data

(60) Provisional application No. 61/104,091, filed on Oct. 9, 2008.

(51) Int. Cl.
| | |
|---|---|
| *C07D 403/12* | (2006.01) |
| *C07D 403/14* | (2006.01) |
| *C07D 405/12* | (2006.01) |
| *C07D 405/14* | (2006.01) |
| *C07D 401/12* | (2006.01) |
| *A61K 31/4965* | (2006.01) |
| *A61K 31/497* | (2006.01) |
| *A61P 33/00* | (2006.01) |

(52) U.S. Cl.
USPC .............. 514/253.04; 514/253.11; 544/364; 544/359; 544/377; 544/362; 544/376

(58) Field of Classification Search
USPC ......... 544/377, 368, 383, 364, 359, 362, 376; 514/254.02, 255.02, 253.04, 253.11
See application file for complete search history.

(56) References Cited

U.S. PATENT DOCUMENTS

| | | | |
|---|---|---|---|
| 3,998,828 A | 12/1976 | Wiedermann | |
| 4,235,871 A | 11/1980 | Papahadjopoulos et al. | |
| 4,315,940 A | 2/1982 | Hitzel et al. | |
| 4,501,728 A | 2/1985 | Geho et al. | |
| 4,593,102 A * | 6/1986 | Shanklin, Jr. ................. 546/216 |
| 4,798,897 A * | 1/1989 | Hidaka et al. ................. 546/139 |
| 4,837,028 A | 6/1989 | Allen | |
| 5,019,369 A | 5/1991 | Presant et al. | |
| 5,962,490 A | 10/1999 | Chan et al. | |
| 6,020,357 A | 2/2000 | Pinto et al. | |
| 7,214,673 B2 * | 5/2007 | Aicher et al. ................. 514/220 |
| 7,572,913 B2 | 8/2009 | McKerracher et al. | |

(Continued)

FOREIGN PATENT DOCUMENTS

| | | |
|---|---|---|
| EP | 1 586 558 A2 | 10/2005 |
| WO | WO 93/13072 A1 | 7/1993 |

(Continued)

OTHER PUBLICATIONS

Lee, et al., International J. Biochem. & Cell Biol., vol. 40, # 5, 2008, 1043-1054.*

(Continued)

*Primary Examiner* — James O Wilson
*Assistant Examiner* — Cecilia M Jaisle
(74) *Attorney, Agent, or Firm* — Leydig, Voit & Mayer, Ltd.

(57) ABSTRACT

Disclosed are pyruvate kinase M2 activators, which are bis sulfonamide piperazinyl and piperidinyl compounds of Formula (I), 2,4-disubstituted 4H-thieno[3,2-c]pyrrole-2-(substituted benzyl)pyridazin-3(2H)-ones of Formula (II) and 6-(3,4-dimethylphenylaminosulfonyl)-3,4-dihydro-1H-quinolin-2-one of formula (III), wherein L, $R^1$, $R^2$, $R^{11}$ to $R^{16}$, $R^{21}$ and $R^{22}$ are as defined herein, that are useful in treating a number of diseases that are treatable by the activation of PKM2, for example, cancer and anemia.

26 Claims, 4 Drawing Sheets

(56) References Cited

U.S. PATENT DOCUMENTS

| | | | |
|---|---|---|---|
| 8,058,313 B2* | 11/2011 | Reddy et al. | 514/679 |
| 8,642,660 B2 | 2/2014 | Goldfarb | |
| 2004/0152648 A1 | 8/2004 | Ullrich et al. | |
| 2005/0176675 A1 | 8/2005 | Gorny | |
| 2007/0032418 A1 | 2/2007 | Shapiro et al. | |
| 2007/0280918 A1 | 12/2007 | Schwartz et al. | |
| 2008/0021116 A1* | 1/2008 | Ullrich et al. | 514/789 |
| 2008/0044833 A1 | 2/2008 | Connors | |
| 2009/0048227 A1 | 2/2009 | Chakravarty et al. | |
| 2009/0163545 A1* | 6/2009 | Goldfarb | 514/312 |
| 2009/0270454 A1* | 10/2009 | Weingarten et al. | 514/326 |
| 2010/0179150 A1* | 7/2010 | Basarab et al. | 514/236.8 |
| 2011/0046083 A1 | 2/2011 | Cantley et al. | |
| 2011/0312931 A1* | 12/2011 | Cioffi et al. | 514/210.2 |

FOREIGN PATENT DOCUMENTS

| | | | |
|---|---|---|---|
| WO | WO 00/53596 A2 | | 9/2000 |
| WO | WO 02/095063 A1 | | 11/2002 |
| WO | WO 03082877 | * | 10/2003 |
| WO | WO 03106381 | * | 12/2003 |
| WO | WO 2006/004195 A1 | | 1/2006 |
| WO | WO 2006/016062 A1 | | 2/2006 |
| WO | WO 2007/127505 | * | 1/2007 |
| WO | WO 2007127505 | * | 1/2007 |
| WO | WO 2007/127505 A2 | | 11/2007 |
| WO | WO 2009/025781 A1 | | 2/2009 |
| WO | WO 2010/042867 A2 | | 4/2010 |

OTHER PUBLICATIONS

Hulleman, et al., Haematologica. Sep. 2009; 94(9): 1322-1324.*
Shi, et al., Cancer Science, vol. 101, # 6, 1447-1453, Jun. 2010.*
Hitosugi, et al., Sci. Signal., Nov. 17, 2009, vol. 2, Issue 97, p. ra73.*
Lee, et al., International J. Biochem. & Cell Biol., vol. 40, #5, 2008, 1043-1054.*
Helleman, et al., Haematologica, Sep. 2009, 94(9), 1322-1324.*
She, et al., Cancer Science, vol. 101, #6, 1447-1453, Jun. 2010.*
Iqbal, et al., Plos One, May 2012, 7, e36764, 8 pages.*
Sun, et al., PNAS Early Edition, 2011, 6 pages.*
Behun et al., "The Chemistry of Pyrazine and Its Derivatives. IV. The Alkylation and Arylation of Methylpyrazine," J. Org. Chem., 26 (9), 3379-3382 (1961).
Chan et al., "Synthesis and characterization of poly(amide sulfonamide)s (PASAs)," J. Polymer. Sci., 33 (15), 2525-2531 (1995).
Inglese et al., "Quantitative high-throughput screening: A titration-based approach that efficiently identifies biological activities in large chemical libraries," Proc. Natl. Acad. Sci., 103 (31), 11473-11478 (2006).
International Preliminary Report on Patentability, Application No. PCT/US2009/060237, dated Apr. 12, 2011.
International Search Report, Application No. PCT/US2009/060237, dated Jun. 16, 2010.
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Oeda, "On Some 2,5-Dialkyl-piperazines," Bull. Chem. Soc., 13, 465-470 (1938).
Paudler et al., "3,7-Disubstituted octahydro-1,5-diazocines. Their conversion into tetrahydro-1,5-diazocines and into ring-contracted products," J. Org. Chem., 32 (8), 2425-2430 (1967).
Pollard et al., "Some Amides of Piperazines," J. Am. Chem. Soc., 75 (2), 491 (1953).
Schroth et al., "RingschluBreaktion von Diacetylen mit Diaminen: Eine Ciniache Synthese von 2,3-Dihydro-1,4-diazepinen," Zeitschrift Fur Chemie., 6 (4), 143 (1969).
Seibel et al., "Synthesis and evaluation of σ-lactams (piperazones) as elastase inhibitors," Bioorg. Med. Chem. Ltrs., 13 (3), 387-389 (2003).
Stewart et al., "Piperazines. I. Derivatives of Piperazine-1-Carboxylic and -1,4-Dicarboxylic Acid,", J. Org. Chem., 18 (1), 1478-1483 (1953).
Szoka et al., "Comparative properties and methods of preparation of lipid vesicles (liposomes)," Ann. Rev. Biophys. Bioeng., 9, 467-508 (1980).
Uozumi et al., "Catalytic asymmetric construction of morpholines and piperazines by palladium-catalyzed tandem allylic substitution reactions," J. Org. Chem., 58 (24), 6826-6832 (1993).
Yar et al., "An Annulation Reaction for the Synthesis of Morpholines, Thiomorpholines, and Piperazines from β-Heteroatom Amino Compounds and Vinyl Sulfonium Salts," Angewandte Chemie., 47 (20), 3784-3786 (2008).
Coy et al., "Ambident Neighbouring Groups, Part V.[1] Mechanism of Cyclization of 2-Halogenoethylsulphonamides to Aziridines," Journal of the Chemical Society, Perkin Transactions 2, 53-58 (1974).
European Patent Office, Second Examination Report in European Patent Application No. 09740795.1 (Feb. 7, 2013).
U.S. Appl. No. 13/433,656, filed Mar. 29, 2012.
Hitosugi et al., "A Malignant Metabolic Switch," Sci. Signal., 97(2), ra73 (Nov. 17, 2009), Abstract.
Hulleman et al., "Pyruvate kinase M2 and prednisolone resistance in acute lymphoblastic leukemia," Haematologica, 94(9), 1322-1324 (Sep. 2009), Abstract.
Jiang et al., "Evaluation of thieno[3,2-b]pyrrole[3,2-d]pyridazinones as activators of the tumor cell specific M2 isoform of pyruvate kinase." Bioorg. Med. Chem. Lett., 20 (11), 3387-3393 (2010).
Lee, "Pyruvate kinase isozyme type M2 (PKM2) Interacts and cooperates with Oct-4 in regulating transcription," International J. Biochem. & Cell Biol., 40(5), 1043-1054 (2008).
Shi, "Silencing of pkm2 increases the efficacy of docetaxel in human lung cancer xenografts in mice," Cancer Science, 101(6), 1447-1453 (Jun. 2010).
Ahmed et al., "M2-PK as a novel marker in ovarian cancer. A prospective cohort study," Eur. J. Gynaecol. Oncol, 28(2), 83-88 (2007).
Wong et al., "PKM2, a Central Point of Regulation in Cancer Metabolism," International J. of Cell Biology, Article ID 242513, 1-11 (2013).
Zhou et al., "Pyruvate Kinase Type M2 Is Upregulated in Colorectal Cancer and Promotes Proliferation and Migration of Colon Cancer Cells," Life, 64(9), 775-782 (Sep. 2012).
Results of SciFinder Structure Search carried out on Sep. 15, 2008.
Anastasiou et al., "Figure 2: TEPP-46 and DASA-58 isoform specificity in vitro and in cells," Nature Chemical Biology, 2012, downloaded Feb. 5, 2014, http://www.nature.com/nchembio/journal/v8/n10/figtabinchennbio.1060 F2. html.
CA Registry No. 842112-70-3, entered into the Registry File on Mar. 4, 2005, supplied by AsinEx.
Fomchenko et al., "Mouse Models of Brain Tumors and Their Applications in Preclinical Trials," Clin. Cancer Res., 2006, 12(18), 5288-5297 (Sep. 15, 2006).
Goldfarb, "Method using lifespan-altering compounds for altering the lifespan of eukaryotic organisms, and screening for such compounds," Chemical Abstract, 151, No. 92842 (2009).
Lawrence et al., "A preclinical xenograft model of prostate cancer using human tumors," Nature Protocols, 8(5), 836-848 (2013).

* cited by examiner

ACTIVATORS OF THE HUMAN PYRUVATE KINASE M2 RECEPTOR

CROSS-REFERENCE TO RELATED APPLICATIONS

This patent application is a U.S. National Phase of International Patent Application No. PCT/US09/60237, filed Oct. 9, 2009, which claims the benefit of U.S. Provisional Patent Application No. 61/104,091, filed Oct. 9, 2008, the disclosures of which are incorporated by reference.

BACKGROUND OF THE INVENTION

Pyruvate kinase (PK) is a critical metabolic enzyme operating at the ultimate step in glycolysis where it catalyzes the transfer of a phosphate group from phosphoenolpyruvate to adenosine diphosphate (ADP), yielding one molecule of pyruvate and one molecule of adenosine triphosphate (ATP). In humans there are two pyruvate kinase genes and each produces two distinct gene products by alternative splicing. The L gene produces two different mRNAs that differ only in the first exon to produce the L (liver specific) and R (red blood cell) specific isozymes. Splicing of a single exon within the M gene produces the M1 isozyme that is found in most adult tissues and the M2 isozyme that is present in fetal tissues and is found to be re-expressed in tumors. Therefore, after embryonic development, adult tissues switch to either express PK-M1 or the tissue specific L or R isozymes. However, in all tumors or cell lines of cancer lineage (including those typically expressing either the L or R isozymes), PK gene expression reverts entirely to the M2 isoform.

PK is a tetrameric enzyme composed of four identical monomers that form a dimer of dimers in the final tetrameric structure. In humans, the M2, L, and R isozymes are activated by fructose-1,6-bis phosphate (FBP) that binds to a flexible loop region at the interface of the two dimers. Activation of PK shifts the enzyme to a state showing high affinity for phosphoenolpyruvate (PEP). In contrast, the M1 isoform is not regulated by FBP and displays only high affinity PEP binding similar to the activated state of PK.

Tumor cells undergo a metabolic transformation that is required to supply the biochemical precursors necessary for rapid cell growth and proliferation.

Various phosphotyrosine peptides can bind to PK-M2 near the activation loop that results in the removal of FBP from the enzyme which effectively down-regulates PK-M2 activity. When PK-M2 is activated, glucose is converted to pyruvate. However, when PK-M2 is inactivated, a build-up of glycolytic intermediates occurs which intermediates can be diverted towards nucleotide and lipid biosynthesis required for cell growth and proliferation.

In addition, PK deficiency is the second most common cause of enzyme-deficient hemolytic anemia, following G6PD deficiency. In patients with PK deficiency, a metabolic block is created in the pathway at the level of the deficient enzyme. Intermediate by-products and various glycolytic metabolites proximal to the metabolic block accumulate in the red blood cells, while such cells become depleted of the distal products in the pathway, such as lactate and ATP. The lack of ATP disturbs the cation gradient across the red cell membrane, causing the loss of potassium and water, which causes cell dehydration, contraction, and crenation, and leads to premature destruction of the red blood cell. The survival of patients with severe PK deficiency depends on a compensatory expression of the PK-M2 isozyme, widely distributed in various tissues, including red blood cells, in which the PK-M2 is the R isozyme.

Accordingly, there is a desire for new activators of PK-M2.

BRIEF SUMMARY OF THE INVENTION

The present invention provides compounds that are activators of the M2 isoform of human pyruvate kinase. In addition, the present invention provides compositions comprising these compounds and methods of using these compound as therapeutic agents in the treatment or prevention of cancer.

The invention provides a compound of the formula (I):

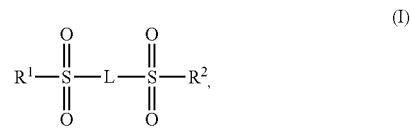

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;
or a pharmaceutically acceptable salt thereof.

The invention provides a compound of the formula (II):

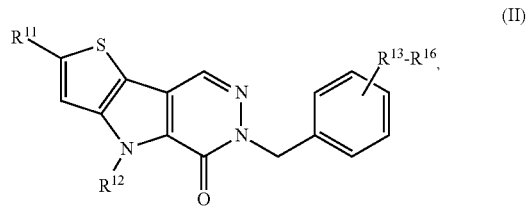

wherein:
$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl,
or a pharmaceutically acceptable salt thereof.

The invention also provides a pharmaceutical composition comprising a compound or salt of the invention and a pharmaceutically acceptable carrier.

The invention further provides a method for treating cancer comprising administering to a patient in need thereof a therapeutically effective amount of a compound of the invention to a mammal afflicted therewith.

The invention additionally provides a method for treating certain forms of anemia associated with downregulation of the R form of pyruvate kinase.

BRIEF DESCRIPTION OF THE SEVERAL VIEWS OF THE DRAWING(S)

DETAILED DESCRIPTION OF THE INVENTION

Figure 1A:
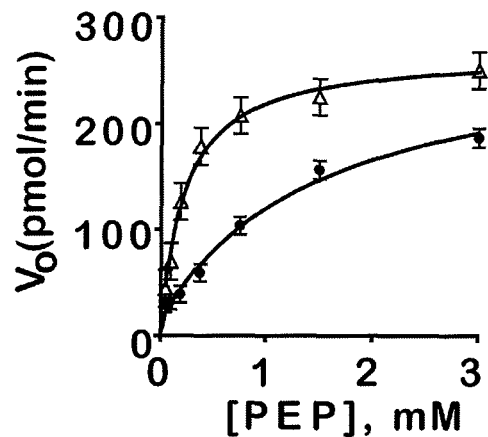
FIG. 1A illustrates that compound 1 increased the affinity of PKM2 for PEP, in accordance with an embodiment of the invention.

In accordance with an embodiment, the invention provides a compound of Formula I:

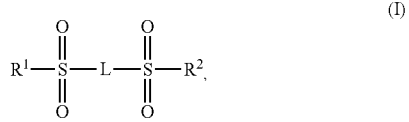

wherein $R^1$ and $R^2$ are aryl or heteroaryl, optionally substituted with one or more substituents selected from the group consisting of $C_1$-$C_{10}$ alkyl, $C_3$-$C_{10}$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

or a pharmaceutically acceptable salt thereof with the provisos that $R^1$ and $R^2$ are not dimethoxyphenyl or $R^1$ and $R^2$ are not both 4-methylphenyl simultaneously.

In accordance with an embodiment, L is a linear amino group, cyclic amino group, or a combination thereof.

In a particular embodiment, the compound of formula I is a compound of formula (Ia):

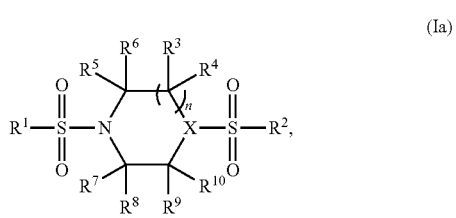

wherein n=1 to 3, $R^1$ and $R^2$ are aryl or heteroaryl optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N, or a pharmaceutically acceptable salt thereof.

In a specific embodiment, the compound or salt according to the above described embodiments is a compound wherein $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, CN, and halogen, $R^3$ and $R^4$ are independently selected from the group consisting of H, $C_1$-$C_{10}$ alkyl, and F, or, taken together, form C=O, and $R^5$ and $R^7$ to $R^{10}$ are independently H, $C_1$-$C_{10}$ alkyl, or F.

In any of the embodiments above, $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alkylenedioxy, CN, and halogen, and $R^3$ to $R^{10}$ are H.

In a particular embodiment of the compounds described above, X is N.

In a preferred embodiment of the compounds described above, n is 1.

Specific examples of the compounds described above include those wherein $R^1$ is selected from the group consisting of phenyl, 4-methylphenyl, 2-methylphenyl, 2-fluorophenyl, 4-chlorophenyl, 4-fluorophenyl, 4,2-difluorophenyl, 2,6-difluorophenyl, 2,4,5-trifluorophenyl, 4-chloro-2-fluorophenyl, 3-chloro-2-fluorophenyl, 4-trifluoromethylphenyl, 3-trifluoromethylphenyl, 2,6-difluoro-4-trifluoromethylphenyl, 2,6-difluoro-4-methoxyphenyl, 2,5-difluoro-4-propylphenyl, 2,6-difluoro-3-hydroxyphenyl, 2,4-difluorophenyl, 4-bromo-2-fluorophenyl, 2,6-difluoro-3-hydroxyphenyl, 3-methoxyphenyl, 4-methoxyphenyl, 4-cyanophenyl, 2-nitrophenyl, 2-pyridyl, 2-pyridyl-1-oxide, 2-(boronic acid)phenyl, 3-(boronic acid)phenyl, and 4-(boronic acid)phenyl; preferably wherein $R^1$ is selected from the group consisting of 2,6-difluoro-4-trifluoromethylphenyl, 2,6-difluorophenyl, 2,6-difluoro-4-methoxyphenyl, 2,6-difluoro-3-hydroxyphenyl, and 4-methoxyphenyl.

In accordance with an embodiment, specific examples of the compound of formula Ia is wherein $R^1$ is heterocyclyl or heteroaryl, selected from the group consisting of 2-pyridyl, 2-pyridyl-N-oxide, 3-pyridyl, 3-pyridyl-N-oxide, 4-pyridyl, 4-pyridyl-N-oxide, 2-pyrimidinyl, 2-pyrimidinyl-N-oxide, 4-pyrimidinyl-N-oxide, 5-pyrimidinyl, pyrimidinyl-N-oxide, 2-pyrazinyl, and 2-pyrazinyl-N-oxide.

In any of the embodiments above, $R^2$ is 6-(2,3-dihydrobenzo[b][1,4]dioxinyl), 7-(3,4-dihydro-2H-benzo[b][1,4]dioxepinyl), 5-benzo[d][1,4]dioxinyl, 7-(4-methyl-3,4-dihydro-2H-pyrido[3,2-b][1,4-oxazinyl), 2-naphthalenyl, 6-(2,2-dimethylchromanyl), 5-(1-methyl-1H-indolyl), 6-(2- methylbenzo[d]thiazolyl), or 4-methoxyphenyl, preferably 6-(2,3-dihydrobenzo[b][1,4]dioxinyl).

In keeping with the embodiments described above, specific examples of compounds include compounds of formula (Ia), wherein X is N, n=1, and $R^3$ to $R^{13}$ is H, and $R^1$ and $R^2$ are as follows:

$R^1$ is 4-methoxyphenyl and $R^2$ is 6-(2,3-dihydro-benzo[b][1,4]dioxinyl);
$R^1$ and $R^2$ are 6-(2,3-dihydro-benzo[b][1,4]dioxinyl);
$R^1$ and $R^2$ are 4-methoxyphenyl;
$R^1$ is 4-cyanophenyl and $R^2$ is 6-(2,3-dihydro-benzo[b][1,4]dioxinyl);
$R^1$ is 4-chlorophenyl and $R^2$ is 6-(2,3-dihydro-benzo[b][1,4]dioxinyl);
$R^1$ is 4-fluorophenyl and $R^2$ is 6-(2,3-dihydro-benzo[b][1,4]dioxinyl);
$R^1$ is 3-fluorophenyl and $R^2$ is 6-(2,3-dihydro-benzo[b][1,4]dioxinyl);
$R^1$ is 2-fluorophenyl and $R^2$ is 6-(2,3-dihydro-benzo[b][1,4]dioxinyl);
$R^1$ is 2,6-difluorophenyl and $R^2$ is 6-(2,3-dihydro-benzo[b][1,4]dioxinyl);
$R^1$ is 2,4,5-trifluorophenyl and $R^2$ is 6-(2,3-dihydro-benzo[b][1,4]dioxinyl);
$R^1$ is 2,6-difluoro-4-methoxyphenyl and $R^2$ is 6-(2,3-dihydro-benzo[b][1,4]dioxinyl);
$R^1$ is 2,5-difluoro-3-propylphenyl and $R^2$ is 6-(2,3-dihydro-benzo[b][1,4]dioxinyl);
$R^1$ is 2,6-difluoro-3-hydroxyphenyl and $R^2$ is 6-(2,3-dihydro-benzo[b][1,4]dioxinyl);
$R^1$ is 2,4-difluorophenyl and $R^2$ is 6-(2,3-dihydro-benzo[b][1,4]dioxinyl);
$R^1$ is phenyl and $R^2$ is 6-(2,3-dihydro-benzo[b][1,4]dioxinyl);
$R^1$ is 3-(trifluoromethylphenyl) and $R^2$ is 6-(2,3-dihydro-benzo[b][1,4]dioxinyl);
$R^1$ is 3-methoxyphenyl and $R^2$ is 6-(2,3-dihydro-benzo[b][1,4]dioxinyl);
$R^1$ is 4-methoxyphenyl and $R^2$ is 6-(2,3-dihydro-benzo[b][1,4]dioxinyl);
$R^1$ is 2-pyridyl and $R^2$ is 6-(2,3-dihydro-benzo[b][1,4]dioxinyl);
$R^1$ is 2-pyridyl-1-oxide and $R^2$ is 6-(2,3-dihydro-benzo[b][1,4]dioxinyl);
$R^1$ is 2,6-difluorophenyl and $R^2$ is 2,6-difluorophenyl;
$R^1$ is 2,6-difluorophenyl and $R^2$ is 7-(3,4-dihydro-2H-benzo[b][1,4]dioxepinyl);
$R^1$ is 2,6-difluorophenyl and $R^2$ is 5-benzo[d][1,4]dioxinyl;
$R^1$ is 2,6-difluorophenyl and $R^2$ is 7-(4-methyl-3,4-dihydro-2H-pyrido[3,2-b][1,4]oxazinyl);
$R^1$ is 2,6-difluorophenyl and $R^2$ is 2-naphthalenyl;
$R^1$ is 2,6-difluorophenyl and $R^2$ is 6-(2,2-dimethylchromanyl);
$R^1$ is 2,6-difluorophenyl and $R^2$ is 5-(1-methyl-1H-indolyl);
$R^1$ is 2,6-difluorophenyl and $R^2$ is 6-(2-methylbenzo[d]thiazolyl); or
$R^1$ is 2,6-difluorophenyl and $R^2$ is 6-(2,3-dihydrobenzo[b][1,4]dioxinyl).

In accordance with another embodiment of the compound of formula Ia, X is CH.

In a preferred embodiment, n is 1. In any of these embodiments, preferably $R^3$, $R^4$, and $R^5$ are H. Examples of such compounds include those wherein $R^1$ is selected from the group consisting of 4-methylphenyl, 2-methylphenyl, 2-fluorophenyl, 3-fluorophenyl, 4,2-difluorophenyl, 2,6-difluorophenyl, 2,4,5-trifluorophenyl, 2,6-difluoro-4-trifluoromethylphenyl, 4-chloro-2-fluoro, 3-chloro-2-fluoro, 4-trifluoromethylphenyl, 4-bromo-2-fluorophenyl, 4-methoxyphenyl, and 2-nitrophenyl, particularly wherein $R^1$ is selected from the group consisting of 2,6-difluoro-4-trifluoromethylphenyl, 2,6-difluorophenyl, and 4-methoxyphenyl. In an embodiment of these compounds, $R^2$ is 3,4-ethylenedioxyphenyl.

In another embodiment of the compound of formula Ia is the compound of formula (Ib):

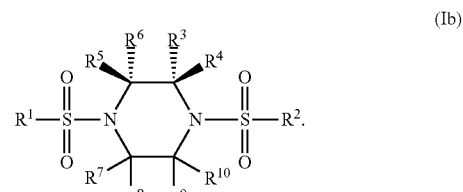

(Ib)

In a further embodiment and The compound or salt of claim 12, wherein the compound is of formula (Ic):

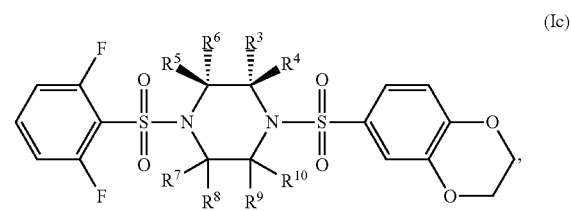

(Ic)

wherein $R^3$ to $R^{10}$ are H or methyl, $R^3$ to $R^6$ and $R^9$ and $R^{10}$ are H or methyl and $R^7$ form C=O, or $R^3$ to $R^8$ are H or methyl and $R^9$ and $R^{10}$ form C=O.

In accordance with an embodiment of the compound of formula (Ic), (i) $R^5$ is methyl and $R^3$, $R^4$, and $R^6$ to $R^{10}$ are H; (ii) $R^6$ is methyl and $R^3$ to $R^5$ and $R^7$ to $R^{10}$ are H; (iii) $R^3$ is methyl and $R^4$ to $R^{10}$ are H; (iv) $R^4$ is methyl and $R^3$ and $R^5$ to $R^{10}$ are H; (v) $R^3$ to $R^8$ are H and $R^9$ and $R^{10}$ form C=O; or (vi) $R^3$ to $R^6$ and $R^7$ and $R^8$ are H and $R^7$ and $R^8$ form C=O.

In accordance with an embodiment of the compound of formula I, L is an alkylene diamino group, cycloalkylamino amino, or cycloalkylamino alkylamino. Examples of compounds of this embodiment include compounds wherein L is N,N'-(ethane-1,2-diyl), N,N'-(propane-1,3-diyl), N,N'-(butane-1,4-diyl), N,N'-(pentane-1,5-diyl), N,N'-(hexane-1,6-diyl), N,N'-((trans)-cyclohexane-1,4-diyl), N,N'-((cis)-cyclohexane-1,4-diyl),

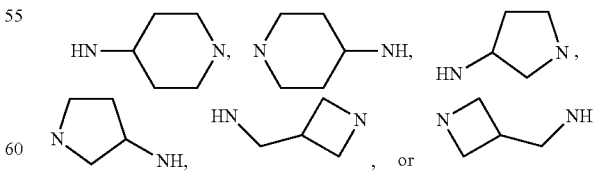

In a specific embodiment of the above compounds, $R^1$ is 2,6-difluorophenyl and $R^2$ is 6-(2,3-dihydrobenzo[b][1,4]dioxinyl)

In accordance with another embodiment, the invention provides a compound of Formula II:

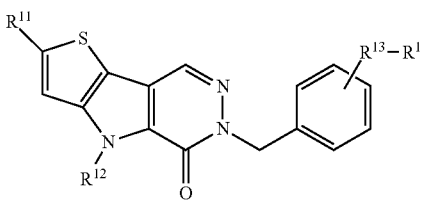

(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof, with the proviso that when $R^{11}$ is methyl, $R^{12}$ is methyl or allyl, and $R^{14}$ to $R^{16}$ are H, then $R^{13}$ is not methoxy or fluoro.

In accordance with an embodiment of the compound of formula II, $R^{11}$ is selected from the group consisting of H, $C_1$-$C_{10}$ alkyl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, methyl, $NCOR^{14}$, and $SO_2R^{14}$, $R^{13}$ to $R^{16}$ are selected from the group consisting of H, $C_1$-$C_{10}$ alkyl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H and $C_1$-$C_{10}$ alkyl.

In a particular embodiment of the compound of formula II, wherein $R^{11}$ is selected from the group consisting of H, $C_1$-$C_{10}$ alkyl, $OR^{17}$, $SR^{17}$, $SOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is H or $C_1$-$C_2$ alkyl, and $R^{13}$ to $R^{16}$ are selected from the group consisting of H, methyl, $CF_3$, methoxy, and halogen.

Referring now to terminology used generically herein, for compounds of formula I or II, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkylene," as used herein, means a cyclic alkylene group fused to the phenyl group to which it is attached and containing from, for example about 3 to about 5 carbon atoms, preferably from about 3 to about carbon atoms. Examples of such substituents include, together with the phenyl, dihydroindenyl and 1,2,3,4-tetrahydronaphthyl.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include propynyl, isopropynyl, n-butynyl, sec-butynyl, isobutynyl, tert-butynyl, pentynyl, isopentynyl, hexynyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heteroaryl," as used herein, refers to a monocyclic or bicyclic 5- or 6-membered aromatic ring system containing one or more heteroatoms selected from the group consisting of O, N, S, and combinations thereof. Examples of suitable monocyclic heteroaryl groups include but are not limited to furanyl, thiopheneyl, pyrrolyl, pyrazolyl, imidazolyl, 1,2,3-triazolyl, isoxazolyl, oxazolyl, isothiazolyl, thiazolyl, pyridinyl, pyrimidinyl, pyrazinyl, and triazinyl. The heteroaryl group can be attached to the sulfonamide group at any available position on the heteroaryl group. For example, a thiopheneyl group can be attached at the 2-position or the 3-position of the thiopheneyl group. A pyridyl group can be attached at the 2-, 3-, or 4-position of the pyridyl group. Suitable bicyclic heterocycloaryl groups include monocyclic heterocycloaryl rings fused to a $C_6$-$C_{10}$ aryl ring. Non-limiting examples of bicyclic heterocycloaryl groups include benzofuran, benzothiophene, quinoline, and isoquinoline. The heteroaryl group is optionally substituted with 1, 2, 3, 4, or 5 substituents as recited herein, wherein the optional substituent can be present at any open position on the heteroaryl group.

The term "heteroaryl oxide," as used herein, refers to an oxidized heteroaryl group as that term is defined herein, wherein one or more of the heteroatoms comprising the heteroaryl group is oxidized. Non-limiting examples of heteroaryl oxide groups include pyridine N-oxide, pyrimidine N-oxide, and pyrazine N-oxide.

The term "heterocyclyl" refers to a cyclic group, which may be aromatic or non-aromatic, or saturated or unsaturated, having one or more heteroatoms such as O, N, or S. Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, triazolyl, tetrazolyl, tetrazinyl, benzoxazolyl, morpholinyl, thiophorpholinyl, quinolinyl, and isoquinolinyl.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2\pi$ electrons, according to Mickel's Rule.

In a particular embodiment of the compound of formula II, $R^{11}$ is selected from the group consisting of H, methyl, ethyl, isopropyl, $OCH_3$, $SCH_3$, $S(O)CH_3$, $NO_2$, $NHCOCH_3$, CN, $COOCH_3$, CHO, $CH_2OH$, $B(OH)_2$, and $CH(OH)CH_3$, $R^{12}$ is methyl, $R^{13}$ is 2-fluoro or chloro, and $R^{14}$ to $R^{16}$ are H.

In any of the embodiments of the compound of formula II, $R^{11}$ and $R^{12}$ are methyl, $R^{13}$ is H, 2-fluoro, 3-fluoro, 4-fluoro, 2-chloro, 3-chloro, 4-chloro, 4-CF3, 4-methyl, or 4-methoxy, and $R^{14}$ to $R^{16}$ are H. Examples of $R^{11}$ and $R^{12}$ are methyl, and of $R^{13}$ and $R^{14}$ are 2-fluoro and 4-fluoro, 2-fluoro and 6-fluoro, 2-fluoro and 3-fluoro, 2-chloro and 6-fluoro, 2-fluoro and 3-methyl, 2-fluoro and 4-methyl, 2-fluoro and 4-$CF_3$, and 2-fluoro and 4-methoxy, and of $R^{15}$ and $R^{16}$ are H.

In a specific embodiment of the compound of the formula II, $R^{11}$ and $R^{12}$ are methyl, $R^{13}$ to $R^{15}$ are 2-fluoro, 3-fluoro, and 4-fluoro, and $R^{16}$ is H. In another specific embodiment of the compound of formula II, $R^{11}$ and $R^{12}$ are methyl, $R^{13}$ to $R^{16}$ are 2-fluoro, 3-fluoro, 5-fluoro, and 6-fluoro.

The present invention also provides a pharmaceutical composition comprising a compound or salt of any of the embodiments described above and a pharmaceutically acceptable carrier.

The present invention further provides a method of treating a disease responsive to activation of human PK-M2 comprising administering to a patient in need thereof a therapeutically effective amount of a compound of Formula I:

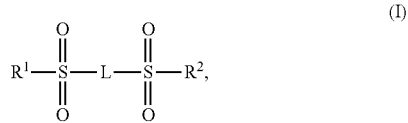

(I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

or a pharmaceutically acceptable salt thereof.

In accordance with an embodiment of the method, the compound is of formula Ia

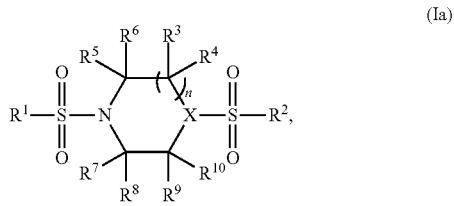

(Ia)

wherein n=1 to 3, $R^1$ and $R^2$ are aryl, phenyl or heteroaryl, optionally substituted with one or more substituents selected from the group consisting of $C_1$-$C_{10}$ alkyl, $C_3$-$C_6$ alkylene, alkenyl, $C_2$-$C_{10}$ alkynyl, haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N.

The present invention further provides a method of treating a disease responsive to activation of human PK-M2 comprising administering to a patient in need thereof a therapeutically effective amount of a compound of Formula II:

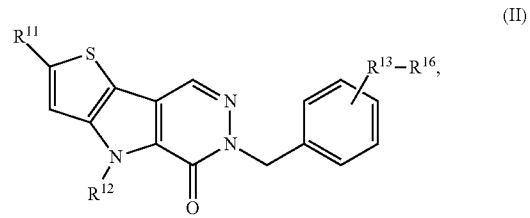

(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof.

The invention further provides the use of a compound or a pharmaceutically acceptable salt thereof in the manufacture of a medicament for treating a disease responsive to activation of human PK-M2 of a patient, wherein the compound is of formula I:

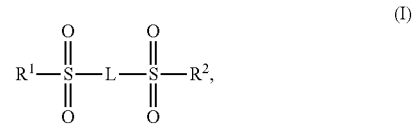

(I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

a compound of formula Ia:

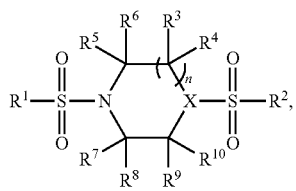

(Ia)

wherein n=1 to 3, $R^1$ and $R^2$ are aryl, phenyl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCO^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N; or a compound of formula II:

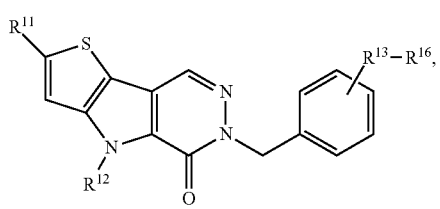

(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl.

In accordance with a further embodiment, the invention provides a compound represented by Formula Id:

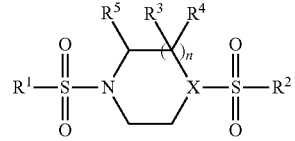

(Id)

wherein n=1 to 3, $R^1$ and $R^2$ are phenyl substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, nitro, boronic acid, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, taken together, form C=O, $R^5$ is H, $C_1$-$C_{10}$ alkyl, or F, $R^6$ is $C_1$-$C_{10}$ alkyl or $C_3$-$C_{10}$ cycloalkyl, and X is CH or N, or a pharmaceutically acceptable salt thereof, with the provisos that (1) when X is N, n=1, and $R^3$, $R^4$, and $R^5$ are H or when X is N, n=1, and one of $R^3$, $R^4$, and $R^5$ is alkyl, $R^1$ is not dimethoxyphenyl and (2) that $R^1$ and $R^2$ are not both 4-methylphenyl.

In certain embodiments of formula (Id), $R^1$ and $R^2$ are phenyl substituted with one or more substituents selected from the group consisting of $C_1$-$C_{10}$ alkyl, $C_1$-$C_{10}$ trihaloalkyl, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, and halogen, wherein $R^3$ and $R^4$ are independently selected from the group consisting of H, $C_1$-$C_{10}$ alkyl, and F, or, taken together, form C=O, and $R^5$ is H, $C_1$-$C_{10}$ alkyl, or F.

In any of the embodiments of formula (Id), $R^1$ and $R^2$ are phenyl substituted with one or more substituents selected from the group consisting of $C_1$-$C_{10}$ alkyl, $C_1$-$C_{10}$ trihaloalkyl, alkylenedioxy, and halogen, and $R^3$, $R^4$, and $R^5$ are H.

In certain embodiments of formula (Id), X is N and n is 1-3. In accordance with a preferred embodiment, n is 1. In a preferred embodiment, $R^1$ is selected from the group consisting of 4-methylphenyl, 2-methylphenyl, 2-fluorophenyl, 3-fluorophenyl, 4,2-difluorophenyl, 2,6-difluorophenyl, 2,4,5-trifluorophenyl, 4-chloro-2-fluorophenyl, 3-chloro-2-fluorophenyl, 4-trifluoromethylphenyl, 2,6-difluoro-4-trifluoromethylphenyl, 4-bromo-2-fluorophenyl, 4-methoxyphenyl, 2-nitrophenyl, 2-(boronic acid)phenyl, 3-(boronic acid)phenyl, and 4-(boronic acid)phenyl. More preferably, $R^1$ is selected from the group consisting of 2,6-difluoro-4-trifluoromethylphenyl, 2,6-difluorophenyl, and 4-methoxyphenyl.

In a preferred embodiment of formula (Id), $R^2$ is 3,4-ethylenedioxyphenyl.

In certain preferred embodiments of the compounds of formula (Id), the invention provides a compound selected from the group consisting of 1-(2,3-dihydrobenzo[b][1,4]dioxin-6-ylsulfonyl)-4-(4-methylphenylphenylsulfonyl)piperazine, 1-(2,3-dihydrobenzo[b][1,4]dioxin-6-ylsulfonyl)-4-(2-methylphenylsulfonyl)piperazine, dihydrobenzo[b][1,4]dioxin-6-ylsulfonyl)-4-(2-fluorophenylsulfonyl)piperazine, 1-(2,3-dihydrobenzo[b][1,4]dioxin-6-ylsulfonyl)-4-(3-fluorophenylsulfonyl)piperazine, 1-(2,3-dihydrobenzo[b][1,4]dioxin-6-ylsulfonyl)-4-(2,4-difluorophenylsulfonyl)piperazine, 1-(2,3-dihydrobenzo[b][1,4]dioxin-6-ylsulfonyl)-4-(2,6-difluorophenylsulfonyl)piperazine, 1-(2,3-dihydrobenzo[b][1,4]dioxin-6-ylsulfonyl)-4-(2,4,5-trifluorophenylsulfonyl)piperazine, 1-(2,3-dihydrobenzo[b][1,4]dioxin-6-ylsulfonyl)-4-(4-chloro-2-fluorophenylsulfonyl)piperazine, 1-(2,3-dihydrobenzo[b][1,4]dioxin-6-ylsulfonyl)-4-(3-chloro-2-fluorophenylsulfonyl)piperazine, 1-(2,3-dihydrobenzo[b][1,4]dioxin-6-ylsulfonyl)-4-(4-trifluoromethylphenylsulfonyl)piperazine, 1-(2,3-dihydrobenzo[b][1,4]dioxin-6-ylsulfonyl)-4-(2,6-difluoro-4-trifluoromethylphenylsulfonyl)piperazine, 1-(2,3-dihydrobenzo[b][1,4]dioxin-6-ylsulfonyl)-4-(4-bromo-2-fluorophenylsulfonyl)piperazine, 1-(2,3-dihydrobenzo[b][1,4]dioxin-6-ylsulfonyl)-4-(4-methoxyphenylsulfonyl)piperazine, 1-(2,3-dihydrobenzo[b][1,4]dioxin-6-ylsulfonyl)-4-(2-nitrophenylsulfonyl)piperazine, 1-(2,3-dihydrobenzo[b][1,4]dioxin-6-ylsulfonyl)-4-(2-(boronic acid)phenylsulfonyl)piperazine, 1-(2,3-dihydrobenzo[b][1,4]dioxin-6-ylsulfonyl)-4-(3-(boronic acid)phenylsulfonyl)piperazine, and 1-(2,3-dihydrobenzo[b][1,4]dioxin-6-ylsulfonyl)-4-(4-(boronic acid)phenylsulfonyl)piperazine.

It will be understood that the terms 2-(boronic acid)phenyl, 3-(boronic acid)phenyl, and 4-(boronic acid)phenyl refer to a group of the formula:

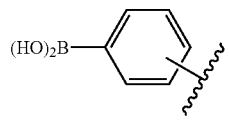

wherein the phenyl group is attached to the sulfonyl group at the 2-, 3-, or 4-position of the phenyl ring.

In certain embodiments of formula (Id), one of $R^3$, $R^4$, or $R^5$ is $C_1$-$C_{10}$ alkyl and two of $R^3$, $R^4$, and $R^5$ are H. In certain preferred embodiments, the invention provides a compound selected from the group consisting of 1-(2,6-difluorophenylsulfonyl)-4-(2,3-dihydrobenzo[b]dioxin-6-ylsulfonyl)-2-methylpiperazine or 1-(2,6-difluorophenylsulfonyl)-4-(2,3-dihydrobenzo[b]dioxin-6-ylsulfonyl)-3-methylpiperazine. It will be recognized that when one of $R^3$, $R^4$, or $R^5$ is $C_1$-$C_{10}$ alkyl, the carbon to which $R^3$, $R^4$, or $R^5$ is $C_1$-$C_{10}$ alkyl is attached is a chiral carbon center.

The invention contemplates embodiments in which a compound having a chiral center is a substantially pure enantiomer thereof, a racemic mixture thereof, or a mixture containing any proportion of the two enantiomers thereof.

In certain embodiments of formula (Id), one of $R^3$, $R^4$, or $R^5$ is F. In accordance with these embodiments, two of $R^3$, $R^4$, or $R^5$ are independently H or $C_1$-$C_{10}$ alkyl, or when $R^5$ is F, $R^3$ and $R^4$, taken together, can be C=O.

In certain embodiments of formula (Id), $R^3$ and $R^4$, taken together, can be C=O. In these embodiments, $R^5$ is H, F, or $C_1$-$C_{10}$ alkyl. In a specific embodiment, the invention provides a compound that is 1-(2,6-difluorophenylsulfonyl)-4-(2,3-dihydrobenzo[b]dioxin-6-ylsulfonyl)-3-oxopiperazine.

In certain embodiments of formula (Id), $R^1$ is selected from the group consisting of 2-pyridyl, 2-pyridyl-N-oxide, 3-pyridyl, 3-pyridyl-N-oxide, 4-pyridyl, 4-pyridyl-N-oxide, 2-pyrimidinyl, 2-pyrimidinyl-N-oxide, 4-pyrimidinyl-N-oxide, 5-pyrimidinyl, 5-pyrimidinyl-N-oxide, 2-pyrazinyl, and 2-pyrazinyl-N-oxide. In a preferred embodiment, $R^1$ is selected from the group consisting of 2-pyridyl, 3-pyridyl, and 4-pyridyl. In a more preferred embodiment, $R^1$ is selected from the group consisting of 2-pyridyl-N-oxide, 3-pyridyl-N-oxide, and 4-pyridyl-N-oxide. In these embodiments, preferably $R^2$ is 3,4-ethylenedioxyphenyl.

In certain embodiments of formula (Id), X is CH and n is 1-3. In accordance with a preferred embodiment, n is 1. In these embodiments, $R^1$, $R^2$, $R^3$, $R^4$, and $R^5$ are as defined previously herein. In a specific embodiment, the invention provides a compound that is 1-(2,6-difluorophenylsulfonyl)-4-(2,3-dihydrobenzo[b]dioxin-6-ylsulfonyl)-piperidine.

In accordance with another embodiment, the invention provides a compound represented by Formula IIa:

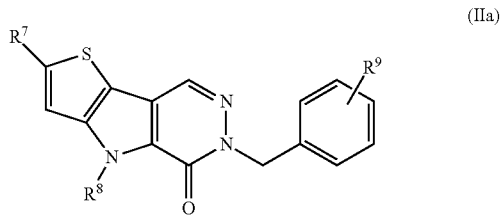

(IIa)

wherein:

$R^7$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{10}$, $SR^{10}$, $SOR^{10}$, $SO_2R^{10}$, $NR^{10}R^{11}$, $NCOR^{10}$, $SCOR^{10}$, $OCOR^{10}$, $B(OH)_2$, and halogen, $R^8$ is selected from the group consisting of $C_1$-$C_{10}$ alkyl, $C_3$-$C_{10}$ cycloalkyl, $NCOR^{10}$, and $SO_2R^{10}$, $R^9$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{10}$, $SR^{10}$, $NR^{10}R^{11}$, $NCOR^{10}$, $OCOR^{10}$, $SCOR^{10}$, $SOR^{10}$, $SO_2R^{10}$, $SO_2NR^{10}R^{11}$, $CF_3$, and halogen, and $R^{10}$ and $R^{11}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof, with the proviso that when $R^7$ is methyl and $R^8$ is methyl or allyl, $R^9$ is not methoxy or fluoro.

In certain embodiments of formula (IIa), $R^7$ is selected from the group consisting of H, $C_1$-$C_{10}$ alkyl, $OR^{10}$, $SR^{10}$, $SOR^{10}$, $SO_2R^{10}$, $NR^{10}R^{11}$, $NCOR^{10}$, $SCOR^{10}$, $OCOR^{10}$, $B(OH)_2$, and halogen, $R^8$ is selected from the group consisting of $C_1$-$C_{10}$ alkyl, $NCOR^{10}$, and $SO_2R^{10}$, $R^9$ is selected from the group consisting of $C_1$-$C_{10}$ alkyl, $OR^{10}$, $SR^{10}$, $NR^{10}R^{11}$, $NCOR^{10}$, $OCOR^{10}$, $SCOR^{10}$, $SOR^{10}$, $SO_2R^{10}$, $SO_2NR^{10}R^{11}$, $CF_3$, and halogen, and $R^{10}$ and $R^{11}$ are independently selected from the group consisting of H and $C_1$-$C_{10}$ alkyl. In preferred embodiments, $R^7$ is selected from the group consisting of H, $C_1$-$C_{10}$ alkyl, or halogen, $R^8$ is $C_1$-$C_{10}$ alkyl, and $R^9$ is selected from the group consisting of $C_1$-$C_{10}$ alkyl, $CF_3$, and halogen.

In certain embodiments of formula (IIa), $R^9$ is 2-fluoro. In accordance with these embodiments, $R^7$ is selected from the group consisting of H, Br, ethenyl, ethyl, propenyl, and propyl, and $R^8$ is methyl. In specific embodiments, the invention provides a compound selected from the group consisting of 4-methyl-4H-thieno[3,2-b]pyrrol-2-(2-fluorobenzyl)pyridazin-3(2H)one, 2-bromo-4-methyl-4H-thieno[3,2-b]pyrrole-2-(2-fluorobenzyl)pyridazin-3(2H)one, 4-methyl-2-vinyl-4H-thieno[3,2-b]pyrrole-2-(2-fluorobenzyl)pyridazin-3(2H)one, 2-ethyl-4-methyl-4H-thieno[3,2-b]pyrrole-2-(2-fluorobenzyl)pyridazin-3(2H)one, 4-methyl-(2-(prop-1-en-2-yl)-4H-thieno[3,2-b]pyrrole-2-(2-fluorobenzyl)pyridazin- 3(2H)one, and 2-isopropyl-4-methyl-4H-thieno[3,2-b]pyrrole-2-(2-fluorobenzyl)pyridazin-3(2H)one.

The present invention further provides a compound or a pharmaceutically acceptable salt thereof in the manufacture of a medicament for treating a disease responsive to activation of human PK-M2 of a patient, wherein the compound is of formula I:

$$R^1-\underset{\underset{O}{\|}}{\overset{\overset{O}{\|}}{S}}-L-\underset{\underset{O}{\|}}{\overset{\overset{O}{\|}}{S}}-R^2, \quad (I)$$

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

a compound of formula Ia:

$$R^1-\underset{\underset{O}{\|}}{\overset{\overset{O}{\|}}{S}}-\underset{R^7}{\overset{R^5}{\underset{|}{\overset{|}{N}}}}\underset{R^8}{\overset{R^6}{\underset{|}{\overset{|}{\phantom{C}}}}}\underset{R^9}{\overset{R^4}{\underset{|}{\overset{|}{\phantom{C}}}}}X-\underset{\underset{O}{\|}}{\overset{\overset{O}{\|}}{S}}-R^2, \quad (Ia)$$

wherein n=1 to 3, $R^1$ and $R^2$ are aryl, phenyl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N; or a compound of formula II:

$$\text{(II)}$$

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl.

The present invention further provides a compound of formula III:

$$R^{21}-\underset{\underset{O}{\|}}{\overset{\overset{O}{\|}}{S}}-R^{22}, \quad (III)$$

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, cycloalkenyl, $C_6$-$C_{10}$ aryl, heterocyclyl, heteroaryl, heteroaryloxide, alkylenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently H, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$, or a pharmaceutically acceptable salt thereof.

In accordance with an embodiment of formula III, the invention provides the following compound or salt thereof:

The present invention further provides a pharmaceutical composition comprising a pharmaceutically acceptable carrier and a compound or salt as above described.

The present invention further provides a method of treating a disease responsive to activation of human PKM2 comprising administering to a patient in need thereof a therapeutically effective amount of a compound or salt as above described.

The present invention further provides for the use of a compound or salt as above described in the manufacture of a medicament for treating a disease responsive to activation of the human PKM2.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a pyridyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, intraperitoneal, intrathecal, rectal, and vaginal administration are merely exemplary and are in no way limiting.

The pharmaceutical composition can be administered parenterally, e.g., intravenously, subcutaneously, intradermally, or intramuscularly. Thus, the invention provides compositions for parenteral administration that comprise a solution of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice,* J. B. Lippincott Company, Philadelphia, pp. 238-250 (1982), and Toissel, *ASHP Handbook on Injectable Drugs,* 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., Ann. Rev. Biophys. Bioeng., 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the individual.

The invention further provides a method for treating a disease responsive to activation of PK-M2 in a mammal comprising administering an effective amount of the compound of the invention to a mammal afflicted therewith. In accordance with an embodiment, the invention provides a method of treating a disease responsive to activation of PK-M2 comprising administering to a patient in need thereof a therapeutically effective amount of a compound represented by Formula Ia:

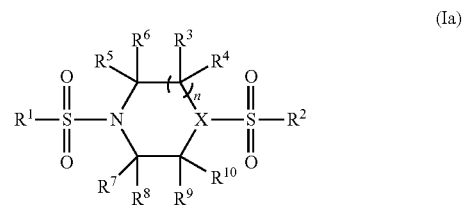

(Ia)

wherein n=1 to 3, $R^1$ and $R^2$ are aryl, phenyl, or heteroaryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, nitro, boronic acid, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, taken together, form C=O, $R^5$ is H, $C_1$-$C_{10}$ alkyl, or F, $R^6$ to $R^{10}$ are H, and X is CH or N, or a pharmaceutically acceptable salt thereof.

In accordance with another embodiment, the invention provides a method of treating a disease responsive to activation of PK-M2 comprising administering to a patient in need thereof a therapeutically effective amount of a compound represented by Formula II:

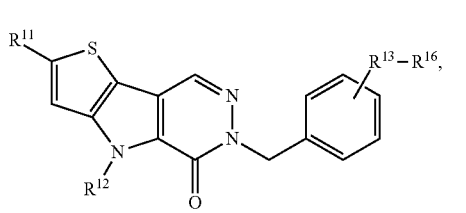

(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $OCOR^{17}$, $B(OH)_2$, and halogen, $R^{12}$ is selected from the group consisting of $C_1$-$C_{10}$ alkyl, $C_3$-$C_{10}$ cycloalkyl, $NCOR^{17}$, and $SO_2R^{17}$, $R^{13}$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof.

The disease responsive to activation of PK-M2 can be cancer or anemia. The cancer can be any suitable cancer, for example, renal cancer, ovarian cancer, breast cancer, CNS cancer, leukemia, prostate cancer, non-small cell lung cancer, colon cancer, or melanoma, particularly renal cancer, CNS cancer, breast cancer, and ovarian cancer. The anemia can be any suitable anemia, for example hemolytic anemia such as human erythrocyte R-type pyruvate kinase deficiency.

The invention further provides a use of a compound or salt of the invention in the manufacture of a medicament for treating disease responsive to activation of PK-M2. The medicament typically is a pharmaceutical composition as described herein.

One skilled in the art will appreciate that suitable methods of utilizing a compound and administering it to a human for the treatment of disease states, in particular, diseases responsive to activation of PK-M2, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a human in accordance with the present invention should be sufficient to effect the desired response. Such responses include reversal or prevention of the bad effects of the disease responsive to activation of PK-M2 for which treatment is desired or to elicit the desired benefit. One skilled in the art will recognize that dosage will depend upon a variety of factors, including the age, condition, and body weight of the human, as well as the source, particular type of the cancer, and extent of cancer in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

The compounds of the invention can prepared by any suitable method. For example, the N,N'-diarylsulfonamides were prepared by a sequence of coupling reaction, deprotection and a second coupling reaction as detailed in Scheme 1. Specifically, mono-boc protected piperazine in methylene chloride at 0° C. in the presence of triethylamine was coupled to numerous aryl sulfonyl chlorides to provide the needed boc-protected N-arylsulfonamides. These intermediates were deprotected with TFA in methylene chloride at 0° C. and subsequently coupled to a second aryl sulfonyl chloride to provide the N,N'-diarylsulfonamide analogues. All final compounds were purified by preparative scale HPLC and the yields for these procedures were typically high. The same procedure was utilized to explore alternate ligations between each aryl-sulfonamide moiety including cyclic diamines of different ring size (analogue 31), linear diamines (analogue 32-36), ring systems with an internal secondary amine and an exocyclic amine (analogues 37-44), and analogues with variously substituted piperazines (analogues 45-47) (scheme not shown). Several of the related sulfone derivatives akin to the lead structure were made according to Scheme 2. To synthesize these derivatives N-boc-4-bromopiperidine was treated with various aryl sulfides in basic DMF to afford the appropriately substituted thiol ethers. Oxidation to the sulfone was accomplished by reaction with mCPBA in methylene chloride at 0° C. Following boc deprotection the secondary amine was coupled to various aryl sulfonyl chlorides to provide the 4-(arylsulfonyl)-1-(arylsulfonyl)piperidine analogues (represented by analogues 20 and 30). N,N'-diarylsulfonamide analogues having the piperazin-2-one core were prepared according to Scheme 3. These derivatives were accessed through treatment of piperazin-2-one with 1 equivalent of various aryl sulfonyl chlorides which preferentially coupled to the free amine moiety. The resulting intermediate was converted to the 1,4-bis(arylsulfonyl)piperazin-2-ones by deprotonation of the amide with LHMDS in THF at −78° C. followed by addition of various aryl sulfonyl chlorides to generate the desired products in good yields (represented by analogues 49 and 50).

Scheme 1

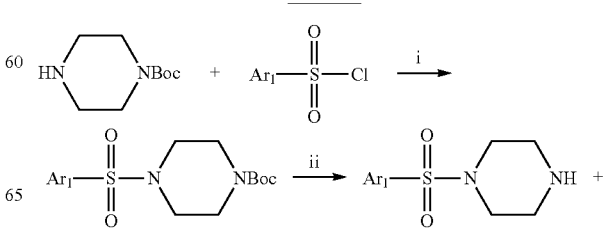

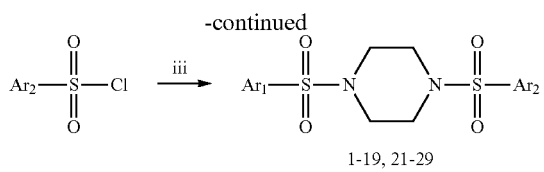

Conditions and reagents: (i) TEA, CH$_2$Cl$_2$, 0° C.; (ii) TFA, CH$_2$Cl$_2$, 0° C.; (iii) TEA, CH$_2$Cl$_2$, 0° C..

Scheme 2

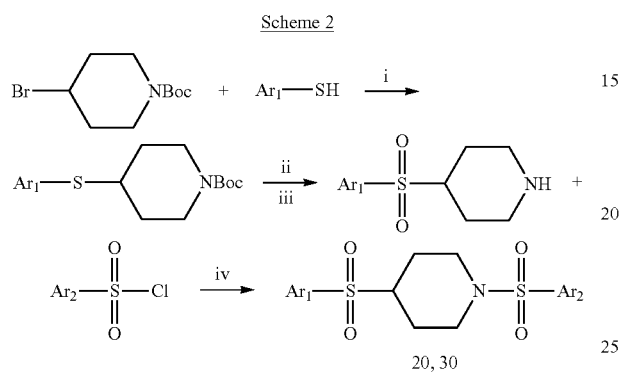

Conditions and reagents: (i) K$_2$CO$_3$, DMF; (ii) MCPBA, CH$_2$Cl$_2$, 0° C.; (iii) TFA, CH$_2$Cl$_2$, 0° C.; (iv) TEA, CH$_2$Cl$_2$, 0° C.;

Scheme 3

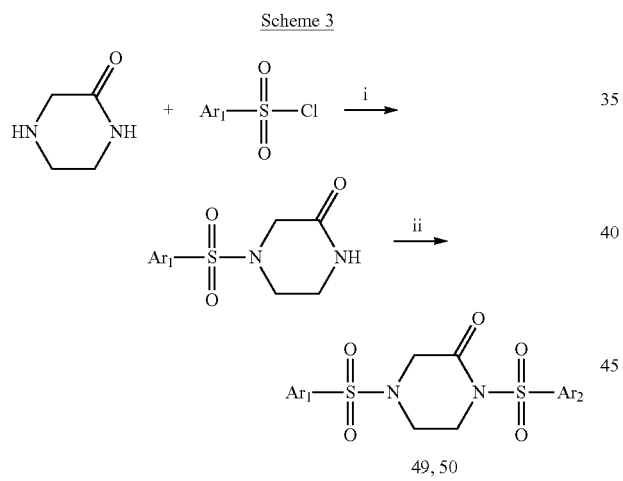

Conditions and reagents: (i) TEA, CH$_2$Cl, 0° C,; (ii) LHMDS, THF, -78° C. - then Ar$_2$SO$_2$Cl.

Compounds of formula II, i.e., the thieno[3,2-b]pyrrole[3,2-d]pyridazinones and analogues were prepared as follows. The sequence required for the chemical synthesis of NCGC00031955 66 was according to Scheme 4. Several commercially available thiophene-2-carbaldehydes were reacted with ethyl 2-azidoacetate in sodium ethoxide at 0° C. to provide the corresponding 2-azido-3-(thiophen-2-yl)acrylates. Refluxing this intermediate in o-xylene provided the core thienopyrroles in good yields. Vilsmeier-Haack reaction was used to form the substituted ethyl 6-formyl-4H-thieno[3,2-b]pyrrole-5-carboxylates. There was no indication of alternate regiochemical acyl insertion. Through a series of experiments, it was necessary to alkylate the pyrrole nitrogen before proceeding with the synthesis. This was accomplished via treatment with alkyl iodides in basic DMF. The remainder of the synthesis involved the formation of the pyridazinone via treatment with hydrazine in refluxing 2-ethoxyethanol and alkylation of the amide nitrogen with various alkyl and benzyl bromides in basic DMF. Arylation of the amide nitrogen was also explored through a copper catalyzed process developed by Buchwald and coworkers (*J. Am. Chem. Soc.*, 123, 7727-7729).

Scheme 4

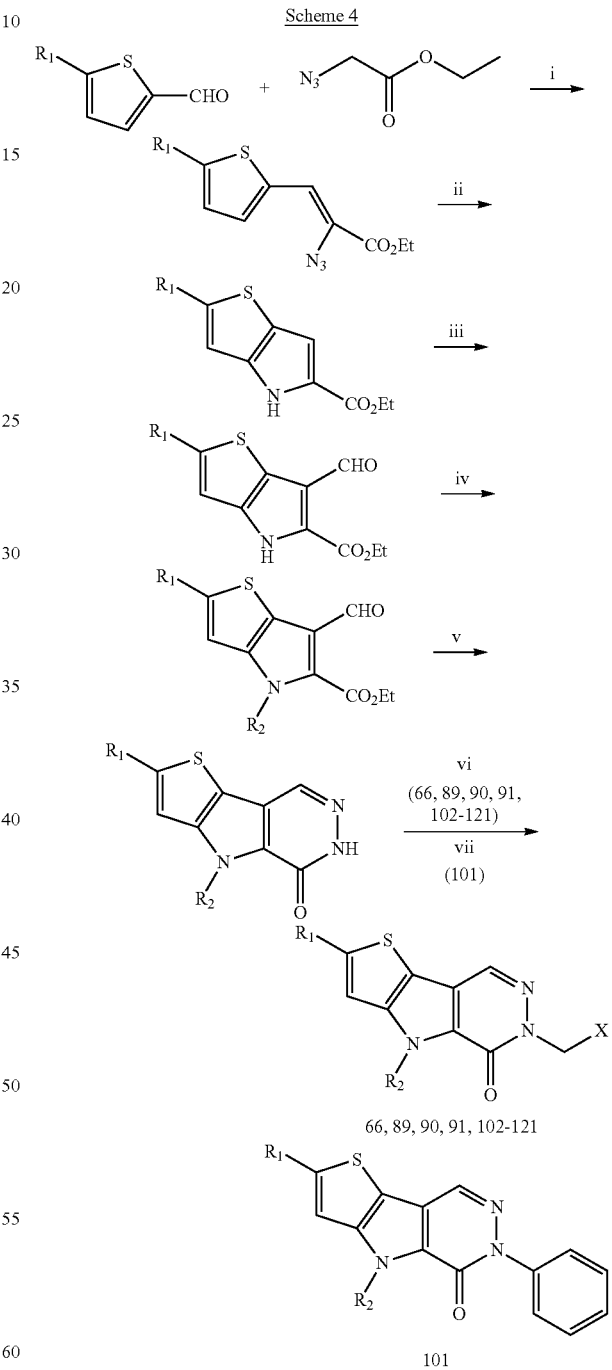

Conditions and reagents: (i) Na, EtOH, 0° C.; (ii) o-Xylene, reflux; (iii) POCl$_3$, DMF, 60° C.; (iv) R$_2$I, K$_2$CO$_3$, DMF, r.t.; (v) 2-Ethoxyethanol, hydrazine, reflux; (vi) Benzyl bromide or alkyl bromide, KOtert-Bu, DMF, r.t.; (vii) iodobenzene, CuI, trans-cyclohexane-1,2-diamine, 1,4-diaxane, reflux.

The utility of 5-bromothiophene-2-carbaldehyde as a starting reagent in this sequence was a key to the synthetic elaboration of numerous analogues (Scheme 5). From the 2-bromo final product we conducted numerous transformations. Treatment with sodium methoxide in refluxing 1,4-dioxane in the presence of copper iodide provided the 2-methoxy derivative 71 in good yield. Copper catalysis was again used for the insertion of acetamide to provide direct access to the NHAc derivative 84. The nitrile analogue 82 was achieved through treatment of the bromide with CuCN in DMF at elevated temperatures. Palladium (0) catalysis, carbon monoxide and triethylamine in a MeOH/DMSO solution proved to be a successful strategy to insert the methyl ester moiety of 83. To obtain compounds having various substituents at the 5-position of the thiophene in the final product, either vinyl or isopropenylboronic acids pinacol esters were entered into traditional Suzuki-Miyaura couplings to provide derivatives that, upon reduction, yielded the ethyl or isopropyl derivatives 68 and 69. Using the identical reductive conditions of the starting bromide provided analogue 70 for study. Creation of the Grignard reagent was accomplished through metal-halogen exchange and exposure of this intermediate to trimethyl borate at 0° C. followed by work-up in 0.1 N aqueous HCl provided the boronic acid analogue 86. Alternatively, quenching of the Grignard reagent with formaldehyde provided the secondary alcohol 88 which was further oxidized to the ketone 87 with IBX in DMSO. Treatment of the bromide with sodium methanethiolate with copper(I) bromide in DMF at 140° C. provided the thiol ether 72 and mCPBA oxidation yielded the sulfoxide 73 and sulfone 74 which were separable through chromatographic methods.

Nitration following insertion of the aldehyde moiety at the 6-position provided nitration to the appropriate 2-position of the heterocycle (Scheme 6). The formation of the pyridazinone ring was more facile proceeding in ethanol at room temperature.

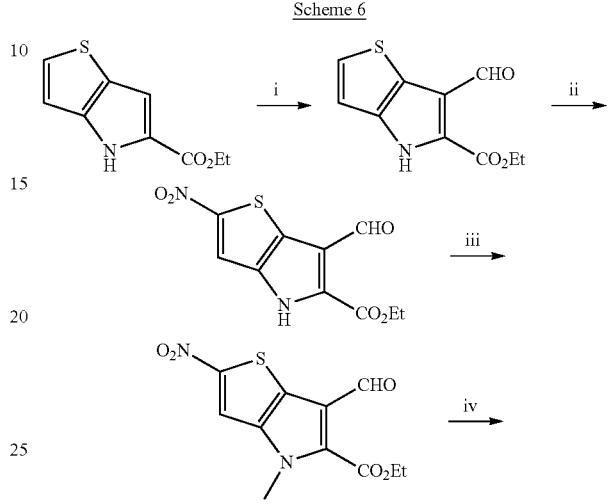

Scheme 6

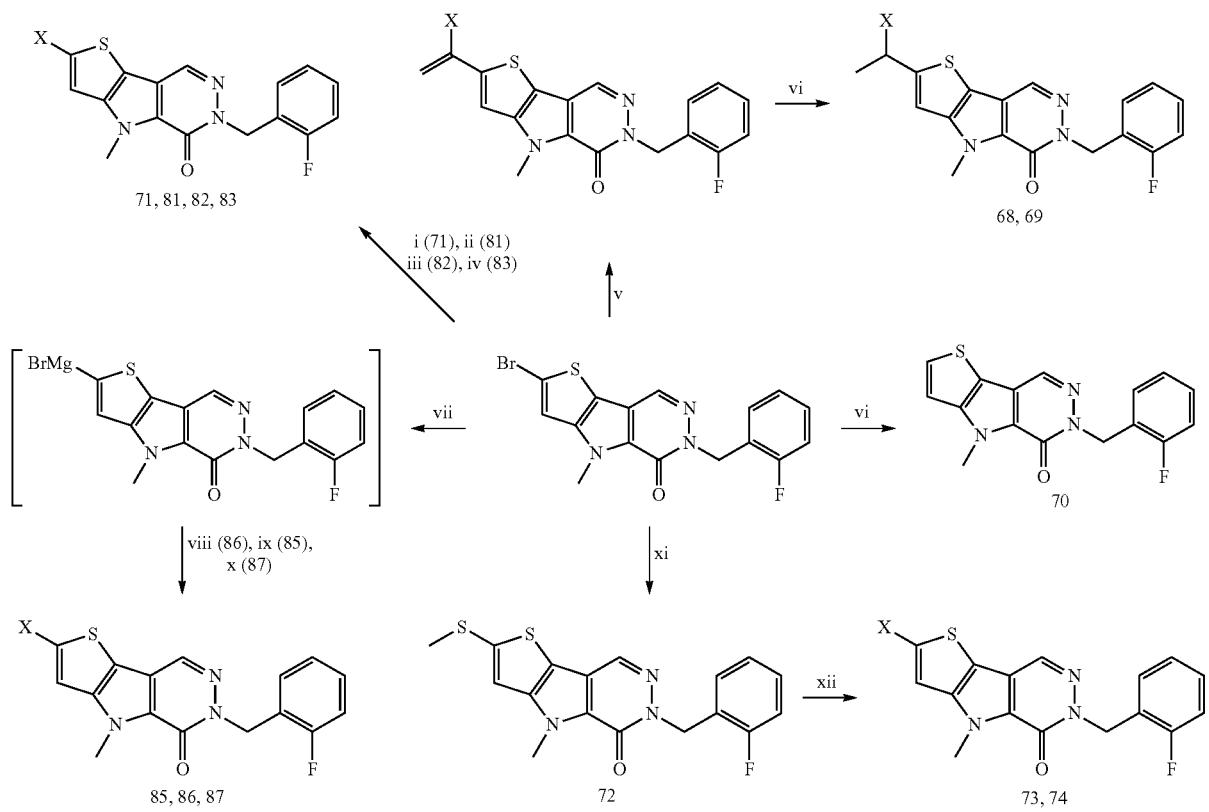

Scheme 5

Conditions and reagents: (i) Na, MeOH, CuI, 1,4-dioxane, reflux; (ii) Acetamide, CuI, trans-cyclohexane-1,2-diamine, dioxane, reflux; (iii) CuCN, DMF, 140° C.; (iv) CO (1 atm), Pd(OAc)$_2$, 1,3-bis(diphenylphosphine)propane, Et$_3$N, MeOH, DMSO, 65° C.. (v) vinyl or isopropenyboronic acid pinacol ester, Pd(PPh$_3$)$_2$Cl$_2$, 1M Na$_2$CO$_3$/CH$_3$CN, 120° C., microwave; (vi) Pd/C, H$_2$ (1 atm), MeOH, r.t.; (vii) $^i$PrMgBr, tetramethylethylenediamine, THF, 15° C., 20 min, then starting material, r.t., 25 min; (viii) B(OMe)$_3$, 0° C., then 0.1N HCl; (ix) CH$_3$CHO, 0° C.; (x) procedure ix followed by IBX, DMSO, r.t.; (xi) NaSMe, CuBr, DMF, 140° C.; (xii) mCPBA (1.5 eq.), CH$_2$Cl$_2$, r.t.;

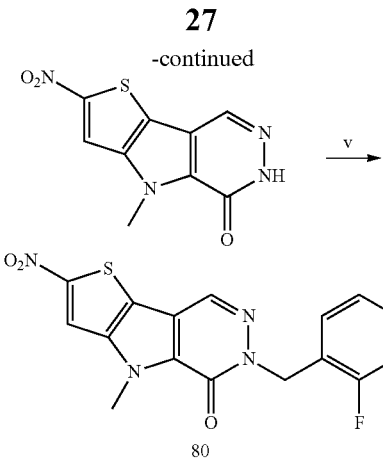

role-5-carboxylate intermediate occurred on the 6 position of the pyrrole ring. Reduction of the nitro group was achieved via treatment with tin (II) chloride in acidic EtOH/H$_2$O and the pyrimidinone ring was formed upon condensation with ammonia formate and formamide at elevated temperatures. The benzylation of the amide nitrogen occurred under similar conditions.

Scheme 8

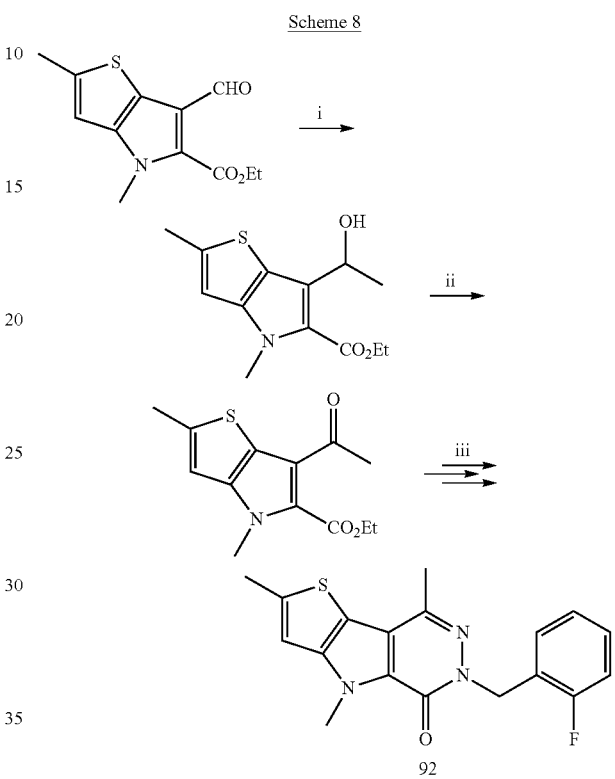

Conditions and reagents: (i) MeMgCl, THF, -78° C.; (ii) IBX, DMSO, r.t.. (iii) steps iv through vi (scheme 1).

Conditions and reagents: (i) POCl$_3$, DMF, 60° C.; (ii) Cu(NO$_3$)$_2$, Ac$_2$O, 0° C. to r.t.; (iii) MeI, K$_2$CO$_3$, DMF; (iv) hydrazine, EtOH, r.t.; (v) 2-fluororobenyl bromide, K$_2$CO$_3$, DMF, r.t..

To insert hydrogen bond donors into the core structure, the un-substituted derivative 71 was entered into a second Vilsmeier-Haack reaction at the 2-position of the thiophene ring to produce the aldehyde 84 (Scheme 7). Reduction of this agent with sodium borohydride in methanol provided the alcohol 88 for examination.

Scheme 7

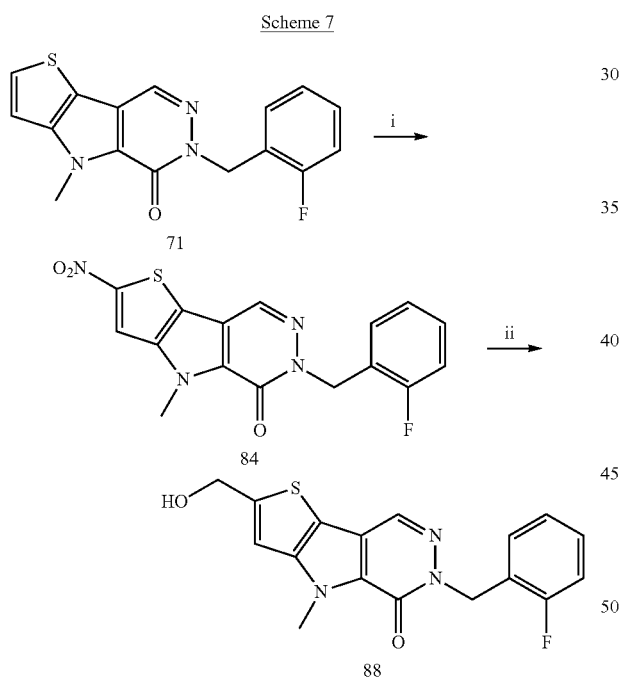

Conditions and reagents: (i) POCl$_3$, DMF, ClCH$_2$CH$_2$Cl, reflux; (ii) NaBH$_4$, MeOH.

Changes were also made directly on or to the pyridazinone ring. The six position of this ring system was the only position open for modification. To examine if substituents could be added at the lone un-substituted carbon the aldehyde was converted to the methyl ketone through addition of a methyl Grignard reagent and IBX oxidation of the resulting secondary alcohol (Scheme 8). From this intermediate, steps iv through vi of Scheme 1 were used to produce the 6-methyl version of our lead compound. A second consideration was changing from a pyridazinone to a pyrimidinone ring system (Scheme 9). To accomplish this, we took advantage of our observation that nitration of the ethyl 4H-thieno[3,2-b]pyr- Scheme 9

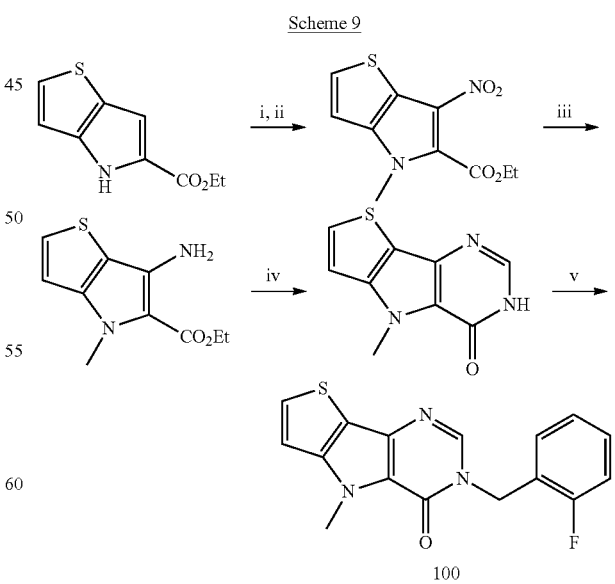

Conditions and reagents: (i) Cu(NO$_3$)$_2$, Ac$_2$O, 0° C. to r.t.; (ii) MeI, K$_2$CO$_3$, DMF; (iii) SnCl$_2$, HCl, EtOH/H$_2$O, 35° C.; (iv) NH$_2$CHO, ammonium formate, 120° C.; (v) 2-fluorobenzyl bromide, K$_2$CO$_3$, EtOH, reflux.

The following examples further illustrate the invention but, of course, should not be construed as in any way limiting its scope.

Unless otherwise noted, all reactions were carried out under an atmosphere of dry argon or nitrogen in dried glassware. Indicated reaction temperatures refer to those of the reaction bath, while room temperature (RT) is noted as 25° C. All solvents were of anhydrous quality purchased form Aldrich Chemical Co. and used as received. Commercially available starting materials and reagents were purchased form Aldrich, TCI and Acros and were used as received.

Example 1

This example illustrates general methods in preparing compounds of the invention in accordance with an embodiment.

All air or moisture sensitive reactions were performed under positive pressure of nitrogen with oven-dried glassware. Anhydrous solvents such as tetrahydrofuran (THF), toluene, dichloromethane, N,N-dimethylforamide (DMF), acetonitrile, methanol and triethylamine were obtained by purchasing from Sigma-Aldrich. Preparative purification was performed on a Waters semi-preparative HPLC. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif.). Method 1: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C. Method 2: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C. Purity determination was performed using an Agilent Diode Array Detector. Mass determination was performed using an Agilent 6130 mass spectrometer with electrospray ionization in the positive mode. $^1$H NMR spectra were recorded on Varian 400 MHz spectrometers. Chemical Shifts are reported in ppm with tetramethylsilane (TMS) as internal standard (0 ppm) for CDCl$_3$ solutions or undeuterated solvent (DMSO-h6 at 2.49 ppm) for DMSO-d6 solutions. All of the analogs for assay have purity greater than 95% based on both analytical methods. High resolution mass spectrometry was recorded on Agilent 6210 Time-of-Flight LC/MS system. Confirmation of molecular formula was accomplished using electrospray ionization in the positive mode with the Agilent Masshunter software (version B.02).

Most bis-sulfonamides were synthesized by a three-step, two-pot procedure (Method A and Method B) exemplified by the synthesis of 1, shown in Schemes 1-3.

Method A:

1-Boc-piperazine (250 mg, 1.34 mmol, 1 equiv.) was dissolved in dichloromethane (2.5 mL) and cooled in an ice bath under nitrogen atmosphere. Triethylamine (375 µl, 2.68 mmol, 2.0 equiv.) was added followed by portionwise addition of 2,3-dihydrobenzo[b][1,4]dioxine-6-sulfonyl chloride (346 mg, 1.48 mmol, 1.1 equiv.). The reaction was stirred in the ice bath for one hour, then quenched with saturated aqueous ammonium chloride (~3 mL). The organic layer was washed twice with saturated ammonium chloride, once with brine, dried over sodium sulfate and concentrated in vacuo and then purified on silica gel chromatography using a 95/5-5/95, hexane/EtOAc (v/v) gradient to give 1-boc-4-(2,3-dihydrobenzo[b][1,4]dioxin-6-ylsulfonyl)piperazine as a white powder (516 mg, 89% yield).

Method B:

1-Boc-4-(2,3-dihydrobenzo[b][1,4]dioxine-6-sulfonyl) piperazine (400 mg, 1.04 mmol) was dissolved in dichloromethane (1 mL) and cooled in an ice bath. Trifluoroacetic acid (1 mL) was then added and the solution was stirred in the ice bath. The reaction was monitored by TLC and showed completion after one hour. The solution was removed from the ice bath and the solvents removed on in vacuo to yield the TFA salt of 1-(2,3-dihydrobenzo[b][1,4]dioxin-6-ylsulfonyl) piperazine, which was carried onto the next step without purification. The oily residue was dissolved in dichloromethane (2 mL) and cooled in an ice bath. Triethylamine (580 µl, 4.16 mmol, 4 equiv.) was added followed by portionwise addition of 4-methoxybenzene-1-sulfonyl chloride (236 mg, 1.14 mmol, 1.1 equiv.). The progress was monitored by TLC and showed completion after 1 hour. The reaction was quenched with saturated aqueous ammonium chloride (~3 mL). The organic layer was washed twice with saturated ammonium chloride, once with brine, dried over sodium sulfate and concentrated in vacuo and then dissolved in DMSO and purified by reverse phase HPLC.

Synthesis of Sulfone 30

4-bromo-1-boc piperidine (500 mg, 1.89 mmol, 1 equiv.) and 2,3-dihydrobenzo[b][1,4]dioxine-6-thiol (318 mg, 1.89 mmol, 1 equiv.) were dissolved in DMF (4 mL). Potassium carbonate (392 mg, 2.84 mmol, 1.5 equiv.) was then added and the solution was stirred at 80° C. for 5 hours. The reaction was cooled to room temperature, diluted with ethyl acetate (~10 mL) and water (~10 mL). The organic layer was washed with saturated aqueous sodium bicarbonate, brine, dried over sodium sulfate and the solvents removed. The crude sulfide was dissolved in dichloromethane (6 mL) and cooled to 0° C. Solid m-CPBA (720 mg, 4.16 mmol, 2.2 equiv. based on initial thiol) was then added and the suspension stirred at 0° C. for 2 hours. The suspension was then filtered and the filtrate was washed with 10% aqueous sodium thiosulfate, aqueous sodium bicarbonate, brine and dried over sodium sulfate. The solvent was removed and the residue was purified by silica gel chromatography using a 95/5-5/95, hexane/EtOAc (v/v) gradient to give the desired sulfone. Method B (see above) was then used to cleave the boc-group and introduce the sulfonamide moiety (by using 2,6-difluorobenzenesulfonyl chloride) to give product 30 which was dissolved in DMSO and purified by reverse phase HPLC.

1-(2,3-dihydrobenzo[b][1,4]dioxin-6-ylsulfonyl)-4-(4-methoxyphenylsulfonyl)piperazine (1)

$^1$H NMR (400 MHz, DMSO-d$_6$) δ: 7.67-7.57 (m, 2H), 7.19-7.08 (m, 4H), 7.08-7.01 (m, 1H), 4.45-4.23 (m, 4H), 3.86 (s, 3H), 2.94 (m, 8H). LC/MS: Method 1, retention time: 5.744 min; Method 2, retention time: 3.889 min. HRMS: m/z (M+)=454.0872 (Calculated for C$_{19}$H$_{22}$N$_2$O$_7$S$_2$=454.0868).

1,4-bis(2,3-dihydrobenzo[b][1,4]dioxin-6-ylsulfonyl) piperazine (2)

$^1$H NMR (400 MHz, DMSO-d$_6$) δ: 7.70-7.61 (m, 2H), 7.61-7.52 (m, 1H), 7.22-7.12 (m, 2H), 7.12-7.05 (m, 1H), 4.35 (m, 8H), 3.44-3.36 (m, 4H), 3.00-2.88 (m, 4H). LC/MS:

Method 1, retention time: 6.114 min; Method 2, retention time: 3.961 min. HRMS: m/z (M+)=482.0816 (Calculated for $C_{20}H_{22}N_2O_8S_2$ 482.0818).

1,4-bis(4-methoxyphenylsulfonyl)piperazine (3)

$^1$H NMR (400 MHz, DMSO-$d_6$) δ: 7.58 (d, 4H, J=6.9 Hz), 7.08 (d, 4H, J=8.4 Hz), 3.82 (s, 6H), 2.91 (s, 8H). LC/MS: Method 1, retention time: 5.828 min; Method 2, retention time: 3.895 min.

4-(4-(2,3-dihydrobenzo[b][1,4]dioxin-6-ylsulfonyl)piperazin-1-ylsulfonyl)benzonitrile (4)

$^1$H NMR (400 MHz, DMSO-$d_6$) δ: 8.07 (d, 2H, J=8.4 Hz), 7.84 (d, 2H, J=8.4 Hz), 7.10 (m, 2H), 7.00 (m, 1H), 4.31 (m, 4H), 3.03-2.91 (m, 8H). LC/MS: Method 1, retention time: 5.671 min; Method 2, retention time: 3.879 min. HRMS: m/z (M+)=449.0716 (Calculated for $C_{19}H_{19}N_3O_6S_2$=449.0715).

1-(4-chlorophenylsulfonyl)-4-(2,3-dihydrobenzo[b][1,4]dioxin-6-ylsulfonyl)piperazine (5)

$^1$H NMR (400 MHz, DMSO-$d_6$) δ: 7.67 (b, 4H), 7.12 (m, 2H), 7.03 (m, 1H), 4.32 (m, 4H), 2.95 (m, 8H). LC/MS: Method 1, retention time: 6.114 min; Method 2, retention time: 3.959 min. HRMS: m/z (M+)=458.0380 (Calculated for $C_{18}H_{19}ClN_2O_6S_2$=458.0373).

1-(2,3-dihydrobenzo[b][1,4]dioxin-6-ylsulfonyl)-4-(4-fluorophenylsulfonyl)piperazine (6)

$^1$H NMR (400 MHz, DMSO-$d_6$) δ: 7.72 (m, 2H), 7.43 (m, 2H), 7.18-7.09 (m, 2H), 7.09-7.01 (m, 1H), 4.32 (m, 4H), 2.93 (m, 8H). LC/MS: Method 1, retention time: 5.813 min; Method 2, retention time: 3.893 min. HRMS: m/z (M+)=442.0677 (Calculated for $C_{18}H_{19}FN_2O_6S_2$=442.0669).

1-(2,3-dihydrobenzo[b][1,4]dioxin-6-ylsulfonyl)-4-(3-fluorophenylsulfonyl)piperazine (7)

$^1$H NMR (400 MHz, DMSO-$d_6$) δ: 7.75-7.64 (m, 1H), 7.64-7.49 (m, 3H), 7.18-7.09 (m, 2H), 7.09-7.01 (m, 1H), 4.43-4.25 (m, 4H), 3.12-3.00 (m, 4H), 2.99-2.82 (m, 4H). LC/MS: Method 1, retention time: 5.853 min; Method 2, retention time: 3.911 min. HRMS; m/z (M+)=442.0662 (Calculated for $C_{18}H_{19}FN_2O_6S_2$=442.0669).

1-(2,3-dihydrobenzo[b][1,4]dioxin-6-ylsulfonyl)-4-(2-fluorophenylsulfonyl)piperazine (8)

$^1$H NMR (400 MHz, DMSO-$d_6$) δ: 7.84-7.68 (m, 2H), 7.52-7.36 (m, 2H), 7.21-7.11 (m, 2H), 7.10-7.02 (m, 1H), 4.44-4.25 (m, 4H), 3.23-3.07 (m, 4H), 3.04-2.87 (m, 4H), LC/MS: Method 1, retention time: 5.775 min; Method 2, retention time: 3.891 min. HRMS; m/z (M+)=442.0664 (Calculated for $C_{18}H_{19}FN_2O_6S_2$=442.0669).

1-(2,6-difluorophenylsulfonyl)-4-(2,3-dihydrobenzo[b][1,4]dioxin-6-ylsulfonyl)piperazine (9)

$^1$H NMR (400 MHz, CDCl$_3$) δ: 7.55 (m, 1H), 7.24 (m, 2H), 7.00 (m, 3H), 4.33 (m, 4H), 3.38 (m, 4H), 3.13 (m, 4H). LC/MS: Method 1, retention time: 5.781 min; Method 2, retention time: 3.889 min. HRMS: m/z (M+)=460.0570 (Calculated for $C_{18}H_{18}F_2N_2O_6S_2$=460.0574).

1-(2,3-dihydrobenzo[b][1,4]dioxin-6-ylsulfonyl)-4-(2,4,5-trifluorophenyl)sulfonyl)piperazine (10)

$^1$H NMR (400 MHz, DMSO-$d_6$) δ: 8.00-7.76 (m, 2H), 7.22-7.12 (m, 2H), 7.11-7.04 (m, 1H), 4.34 (dd, 4H, J=12.13, 5.09 Hz), 3.24-3.14 (m, 4H), 3.04-2.87 (m, 4H). LC/MS: Method 1, retention time: 6.076 min; Method 2, retention time: 3.936 min. HRMS; m/z (M+)=478.0495 (Calculated for $C_{18}H_{17}F_3N_2O_6S_2$=478.0480).

1-(2,6-difluoro-4-methoxyphenylsulfonyl)-4-(2,3-dihydrobenzo[b][1,4]dioxin-6-ylsulfonyl)piperazine (11)

$^1$H NMR (400 MHz, CDCl$_3$) δ: 7.22 (m, 2H), 6.97 (m, 1H), 6.53 (d, 2H, J=10.56 Hz), 4.26 (m, 4H), 3.87 (s, 3H), 3.31 (m, 4H), 3.11 (m, 4H). LC/MS: Method 1, retention time: 5.922 min; Method 2, retention time: 3.911 min. HRMS; m/z (M+)=490.0698 (Calculated for $C_{19}H_{20}F_2N_2O_7S_2$=490.0680).

1-(2,5-difluoro-4-propylphenylsulfonyl)-4-(2,3-dihydrobenzo[b][1,4]dioxin-6-ylsulfonyl)piperazine (12)

$^1$H NMR (400 MHz, CDCl$_3$) δ: 7.44 (dd, 1H, J=8.41, 5.67 Hz), 7.23 (m, 2H), 7.06 (dd, 1H, J=10.17, 5.48 Hz), 6.98 (d, 1H, J=8.22 Hz), 4.32 (m, 4H), 3.30 (m, 4H), 3.11 (m, 4H), 2.66 (t, 2H, J=7.43 Hz), 1.66 (m, 2H), 0.98 (t, 3H, J=7.43 Hz). LC/MS: Method 1, retention time: 6.737 min; Method 2, retention time: 4.055 min. HRMS: m/z (M+)=502.1057 (Calculated for $C_{21}H_{24}F_2N_2O_6S_2$=502.1044).

3-(4-(2,3-dihydrobenzo[b][1,4]dioxin-6-ylsulfonyl)piperazin-1-ylsulfonyl)-2,4-difluorophenol (13)

$^1$H NMR (400 MHz, CDCl$_3$) δ: 7.25 (m, 3H), 7.05 (m, 2H), 4.33 (m, 4H), 3.37 (m, 4H), 3.13 (m, 4H), 1.84 (b, 1H). LC/MS: Method 1, retention time: 5.783 min; Method 2, retention time: 3.888 min. HRMS: m/z (M+)=476.0542 (Calculated for $C_{18}H_{18}F_2N_2O_7S_2$=476.0523).

1-(2,4-difluorophenylsulfonyl)-4-(2,3-dihydrobenzo[b][1,4]dioxin-6-ylsulfonyl)piperazine (14)

$^1$H NMR (400 MHz, DMSO-$d_6$) δ: 7.81 (m, 1H), 7.57 (ddd, 1H, J=10.96, 9.00, 2.35 Hz) 7.32 (td, 1H, J=8.51, 2.15 Hz), 7.23-7.11 (m, 2H), 7.11-7.01 (m, 1H), 4.40-4.27 (m, 4H), 3.22-3.08 (m, 4H), 3.03-2.80 (m, 4H), LC/MS: Method 1, retention time: 5.910 min; Method 2, retention time: 3.910 min. HRMS: m/z (M+)=460.0585 (Calculated for $C_{18}H_{18}F_2N_2O_6S_2$=460.0574).

1-(2,3-dihydrobenzo[b][1,4]dioxin-6-ylsulfonyl)-4-(phenylsulfonyl)piperazine (15)

$^1$H NMR (400 MHz, DMSO-$d_6$) δ: 7.73-7.64 (m, 3H), 7.59 (m, 2H), 7.13-7.07 (m, 2H), 7.01 (m, 1H) 4.30 (m, 4H), 2.98-2.88 (m, 8H). LC/MS: Method 1, retention time: 5.706 min; Method 2, retention time: 3.883 min. HRMS: m/z (M+)=424.0769 (Calculated for $C_{18}H_{20}N_2O_6S_2$=424.0763).

1-(2,3-dihydrobenzo[b][1,4]dioxin-6-ylsulfonyl)-4-(3-(trifluoromethyl)phenylsulfonyl)piperazine (16)

$^1$H NMR (400 MHz, CDCl$_3$) δ: 7.96 (s, 1H), 7.89 (m, 2H), 7.70 (m, 1H), 7.20 (m, 2H), 6.96 (d, 1H, J=8.61 Hz), 4.31 (m,

4H), 3.11 (m, 8H). LC/MS: Method 1, retention time: 6.249 min; Method 2, retention time: 3.920 min. HRMS: m/z (M+)=492.0654 (Calculated for $C_{19}H_{19}F_3N_2O_6S_2$=492.0637).

1-(2,3-dihydrobenzo[b][1,4]dioxin-6-ylsulfonyl)-4-(3-methoxyphenylsulfonyl)piperazine (17)

$^1$H NMR (400 MHz, DMSO-d$_6$) δ: 7.50 (m, 1H), 7.24 (m, 2H), 7.09 (m, 3H), 7.01 (m, 1H) 4.31 (m, 4H), 3.80 (s, 3H), 2.99 (m, 4H), 2.89 (m, 4H). LC/MS: Method 1, retention time: 5.819 min; Method 2, retention time: 3.902 min. HRMS: m/z (M+)=454.0878 (Calculated for $C_{19}H_{22}N_2O_7S_2$=454.0868).

1-(2,3-dihydrobenzo[b][1,4]dioxin-6-ylsulfonyl)-4-(pyridin-2-ylsulfonyl)piperazine (18)

$^1$H NMR (400 MHz, CDCl$_3$) δ: 8.68 (d, 1H, J=4.7 Hz), 7.92 (m, 2H), 7.51 (m, 1H), 7.24 (m, 2H), 6.99 (d, 1H, J=8.61 Hz), 4.33 (m, 4H), 3.44 (m, 4H), 3.09 (m, 4H). LC/MS: Method 1, retention time: 5.205 min; Method 2, retention time: 3.772 min. HRMS: m/z (M+)=425.0720 (Calculated for $C_{17}H_{19}N_3O_6S_2$=425.0715).

2-(4-(2,3-dihydrobenzo[b][1,4]dioxin-6-ylsulfonyl)piperazin-1-ylsulfonyl)pyridine 1-oxide (19)

$^1$H NMR (400 MHz, DMSO-d$_6$) δ: 8.27 (m, 1H), 7.90 (m, 1H), 7.57 (m, 1H), 7.41 (m, 1H), 7.06 (m, 3H), 4.30 (m, 4H), 3.40 (m, 4H), 2.87 (m, 4H). LC/MS: Method 1, retention time: 4.618 min; Method 2, retention time: 3.630 min. HRMS: m/z (M+)=441.0669 (Calculated for $C_{17}H_{19}N_3O_7S_2$=441.0664).

4-(2,6-difluorophenylsulfonyl)-1-(2,3-dihydrobenzo[b][1,4]dioxin-6-ylsulfonyl)piperidine (20)

$^1$H NMR (400 MHz, CDCl$_3$) δ: 7.63 (m, 1H), 7.24 (m, 2H), 7.06 (t, 2H, J=8.61 Hz), 6.96 (d, 1H, J=8.61 Hz), 4.31 (m, 4H), 3.88 (d, 2H, J=12.1 Hz), 3.08 (m, 1H), 2.40 (td, 2H, J=11.93, 2.35 Hz), 2.14 (m, 2H), 1.96 (m, 2H). LC/MS: Method 1, retention time: 5.561 min; Method 2, retention time: 3.847 min. HRMS: m/z (M+)=459.0634 (Calculated for $C_{19}H_{19}F_2NO_6S_2$=459.0622).

1-(2,6-difluorophenylsulfonyl)-4-(4-methoxyphenylsulfonyl)piperazine (21)

$^1$H NMR (400 MHz, CDCl$_3$) δ: 7.66 (m, 2H), 7.54 (m, 2H), 7.02 (m, 3H), 3.88 (s, 3H), 3.35 (m, 4H), 3.09 (m, 4H). LC/MS: Method 1, retention time: 5.829 min; Method 2, retention time: 3.904 min. HRMS: m/z (M+)=432.0633 (Calculated for $C_{17}H_{18}F_2N_2O_5S_2$=432.0625).

1,4-bis(2,6-difluorophenylsulfonyl)piperazine (22)

$^1$H NMR (400 MHz, CDCl$_3$) δ: 7.54 (m, 2H), 7.04 (t, 4H, J=12 Hz), 3.40 (s, 8H). LC/MS: Method 1, retention time: 5.851 min; Method 2, retention time: 3.911 min. HRMS: m/z (M+)=438.0331 (Calculated for $C_{16}H_{14}F_4N_2O_4S_2$=438.034).

1-(2,6-difluorophenylsulfonyl)-4-(3,4-dihydro-2H-benzo[b][1,4]dioxepin-7-ylsulfonyl)piperazine (23)

$^1$H NMR (400 MHz, DMSO-d$_6$) δ: 7.72 (m, 1H), 7.31-7.18 (m, 4H), 7.11 (d, 1H, J=8.4 Hz), 4.22 (dt, 8H, J=17.8 Hz, 4 Hz), 3.18 (m, 4H), 2.98 (m, 4H), 2.14 (m, 2H). LC/MS: Method 1, retention time: 5.973 min; Method 2, retention time: 3.925 min. HRMS: m/z (M+)=474.0747 (Calculated for $C_{19}H_{20}F_2N_2O_6S_2$=474.0731).

1-(benzo[d][1,3]dioxol-5-ylsulfonyl)-4-(2,6-difluorophenylsulfonyl)piperazine (24)

$^1$H NMR (400 MHz, DMSO-d$_6$) δ: 7.75 (m, 1H), 7.29 (m, 2H), 7.22 (m, 1H), 7.16 (m, 1H), 7.07 (d, 1H, J=8.2 Hz), 6.17 (s, 2H), 3.17 (m, 4H), 2.99 (m, 4H). LC/MS: Method 1, retention time: 5.741 min; Method 2, retention time: 3.879 min. HRMS: m/z (M+)=446.0427 (Calculated for $C_{17}H_{16}F_2N_2O_6S_2$=446.0418).

6-(4-(2,6-difluorophenylsulfonyl)piperazin-1-ylsulfonyl)-4-methyl-3,4-dihydro-2H-benzo[b][1,4]oxazine (25)

$^1$H NMR (400 MHz, DMSO-d$_6$) δ: 7.74 (m, 1H), 7.29 (m, 2H), 6.89-6.76 (m, 3H), 4.27 (m, 2H), 3.28 (m, 2H), 3.17 (m, 4H), 2.96 (m, 4H), 2.84 (s, 3H). LC/MS: Method 1, retention time: 5.514 min; Method 2, retention time: 3.813 min. HRMS: m/z (M+)=473.0897 (Calculated for $C_{19}H_{21}F_2N_3O_5S_2$=473.0891).

1-(2,6-difluorophenylsulfonyl)-4-(naphthalen-2-ylsulfonyl)piperazine (26)

$^1$H NMR (400 MHz, DMSO-d$_6$) δ: 8.39 (s, 1H), 8.18-8.03 (m, 3H), 7.76-7.56 (m, 4H), 7.14 (m, 2H), 3.20-3.17 (m, 8H). LC/MS: Method 1, retention time: 5.532 min; Method 2, retention time: 3.814 min. HRMS: m/z (M+)=452.0673 (Calculated for $C_{20}H_{18}F_2N_2O_4S_2$=452.0676).

1-(2,6-difluorophenylsulfonyl)-4-(2,2-dimethylchroman-6-ylsulfonyl)piperazine (27)

$^1$H NMR (400 MHz, CDCl$_3$) δ: 7.54 (m, 1H), 7.43 (m, 2H), 7.03 (m, 2H), 6.5 (d, 1H, J=8.4 Hz), 3.36 (m, 4H), 3.11 (m, 4H), 2.81 (m, 2H), 1.84 (m, 2H), 1.36 (s, 6H). LC/MS: Method 1, retention time: 5.514 min; Method 2, retention time: 3.811 min. HRMS: m/z (M+)=486.1100 (Calculated for $C_{21}H_{24}F_2N_2O_5S_2$=486.1095).

5-(4-(2,6-difluorophenylsulfonyl)piperazin-1-ylsulfonyl)-1-methyl-1H-indole (28)

$^1$H NMR (400 MHz, DMSO-d$_6$) δ: 7.94 (s, 1H), 7.62 (m, 2H), 7.54 (d, 1H, J=3.1 Hz), 7.42 (m, 1H), 7.19 (t, 2H, J=9.0 Hz), 6.63 (d, 1H, J=2.9 Hz), 3.85 (s, 3H), 3.15 (m, 4H), 2.95 (m, 4H). LC/MS: Method 1, retention time: 5.893 min; Method 2, retention time: 3.914 min. HRMS: m/z (M+)=455.0793 (Calculated for $C_{19}H_{19}F_2N_3O_4S_2$=455.0785).

5-(4-(2,6-difluorophenylsulfonyl)piperazin-1-ylsulfonyl)-2-methylbenzo[d]thiazole (29)

$^1$H NMR (400 MHz, DMSO-d$_6$) δ: 8.51 (s, 1H), 8.07 (m, 1H), 7.73 (m, 1H), 7.64 (m, 1H), 7.20 (m, 2H), 3.09 (m, 8H), 2.86 (s, 3H). LC/MS: Method 1, retention time: 5.729 min; Method 2, retention time: 3.882 min. HRMS: m/z (M+)=473.0353 (Calculated for $C_{18}H_{17}F_2N_3O_4S_3$=473.0349).

1-(2,6-difluorophenylsulfonyl)-4-(2,3-dihydrobenzo[b][1,4]dioxin-6-ylsulfonyl)piperidine (30)

$^1$H NMR (400 MHz, CDCl$_3$) δ: 7.52 (m, 1H), 7.35-7.26 (m, 2H), 7.07-6.97 (m, 3H), 4.40-4.28 (m, 4H), 4.08-4.00 (m, 2H), 2.92 (m, 1H), 2.66 (t, 2H, J=11.93 Hz), 2.17-2.08 (m, 2H), 1.80-1.67 (m, 2H). LC/MS: Method 1, retention time: 5.584 min; Method 2, retention time: 3.853 min; HRMS: m/z (M+)=459.0631 (Calculated for C$_{19}$H$_{19}$F$_2$NO$_6$S$_2$=459.0622).

1-(2,6-difluorophenylsulfonyl)-4-(2,3-dihydrobenzo[b][1,4]dioxin-6-ylsulfonyl)-1,4-diazepane (31)

$^1$H NMR (400 MHz, CDCl$_3$) δ: 7.50 (m, 1H), 7.28 (m, 2H), 7.02 (m, 2H), 6.96 (d, 1H, J=8.6 Hz), 4.32 (m, 4H), 3.56 (m, 4H), 3.41 (m, 4H), 2.05 (m, 2H). LC/MS: Method 1, retention time: 5.812 min; Method 2, retention time: 3.891 min. HRMS: m/z (M+)=474.0731 (Calculated for C$_{19}$H$_{20}$F$_2$N$_2$O$_6$S$_2$=474.0731).

N-(2-(2,6-difluorophenylsulfonamido)ethyl)-2,3-dihydrobenzo[b][1,4]dioxine-6-sulfonamide (32)

$^1$H NMR (400 MHz, CDCl$_3$) δ: 7.54 (m, 1H), 7.35 (m, 2H), 7.06 (m, 2H), 6.96 (d, 1H, J=8.2 Hz), 5.37 (b, 1H), 4.73 (b, 1H), 4.31 (m, 4H), 3.25 (m, 2H), 3.14 (m, 2H). LC/MS: Method 1, retention time: 4.986 min; Method 2, retention time: 3.711 min. HRMS: m/z (M+)=434.0434 (Calculated for C$_{16}$H$_{16}$F$_2$N$_2$O$_6$S$_2$=434.0418).

N-(3-(2,6-difluorophenylsulfonamido)propyl)-2,3-dihydrobenzo[b][1,4]dioxine-6-sulfonamide (33)

$^1$H NMR (400 MHz, CDCl$_3$) δ: 7.52 (m, 1H), 7.34 (m, 2H), 7.04 (m, 2H), 6.96 (d, 1H, J=8.22 Hz), 5.43 (t, 1H, J=6.46 Hz), 4.85 (b, 1H), 4.31 (m, 4H), 3.21 (q, 2H, J=6.26 Hz), 3.05 (t, 2H, J=6.06 Hz), 1.74 (m, 2H). LC/MS: Method 1, retention time: 5.115 min; Method 2, retention time: 3.730 min. HRMS: m/z (M+)=448.0571 (Calculated for C$_{17}$H$_{18}$F$_2$N$_2$O$_6$S$_2$=448.0574).

N-(4-(2,6-difluorophenylsulfonamido)butyl)-2,3-dihydrobenzo[b][1,4]dioxine-6-sulfonamide (34)

$^1$H NMR (400 MHz, CDCl$_3$) δ: 7.49 (m, 1H), 7.31 (m, 2H), 7.02 (m, 2H), 6.91 (d, 1H, J=8.22 Hz), 5.03 (m, 1H), 4.47 (m, 1H), 4.28 (m, 4H), 3.06 (m, 2H), 2.89 (m, 2H), 1.54 (m, 4H). LC/MS: Method 1, retention time: 5.238 min; Method 2, retention time: 3.757 min. HRMS: m/z (M+)=462.0739 (Calculated for C$_{18}$H$_{20}$F$_2$N$_2$O$_6$S$_2$=462.0731).

N-(5-(2,6-difluorophenylsulfonamido)pentyl)-2,3-dihydrobenzo[b][1,4]dioxine-6-sulfonamide (35)

$^1$H NMR (400 MHz, CDCl$_3$) δ: 7.52 (m, 1H), 7.35 (m, 2H), 7.04 (m, 2H), 6.96 (d, 1H, J=8.61 Hz), 5.00 (b, 1H), 4.32 (m, 4H), 3.07 (q, 1H, J=6.65 Hz), 2.91 (t, 1H, J=6.85 Hz), 2.70 (b, 1H), 1.50 (m, 4H), 1.32 (m, 2H). LC/MS: Method 1, retention time: 5.450 min; Method 2, retention time: 3.798 min. HRMS: m/z (M+)=476.0899 (Calculated for C$_{19}$H$_{22}$F$_2$N$_2$O$_6$S$_2$=476.0877).

N-(6-(2,6-difluorophenylsulfonamido)hexyl)-2,3-dihydrobenzo[b][1,4]dioxine-6-sulfonamide (36)

$^1$H NMR (400 MHz, CDCl$_3$) δ: 7.52 (m, 1H), 7.36 (m, 2H), 7.04 (m, 2H), 6.96 (d, 1H, J=8.61 Hz), 4.99 (m, 4H), 3.08 (m, 2H), 2.91 (m, 2H), 1.72 (b, 1H), 1.47 (m, 4H), 1.27 (m, 4H). LC/MS: Method 1, retention time: 5.629 min; Method 2, retention time: 3.836 min. HRMS: m/z (M+)=490.1056 (Calculated for C$_{20}$H$_{24}$F$_2$N$_2$O$_6$S$_2$=490.1044).

N-((trans)-4-(2,6-difluorophenylsulfonamido)cyclohexyl)-2,3-dihydrobenzo[b][1,4]dioxine-6-sulfonamide (37)

$^1$H NMR (400 MHz, CDCl$_3$) δ: 7.49 (m, 1H), 7.30 (m, 2H), 7.00 (m, 2H), 6.91 (d, 1H, J=8.61 Hz), 4.95 (m, 1H), 4.47 (m, 1H), 4.28 (m, 4H), 3.25 (b, 1H), 3.00 (b, 1H), 1.84 (m, 4H), 1.24 (m, 4H). LC/MS: Method 1, retention time: 5.290 min; Method 2, retention time: 3.760 min. HRMS: m/z (M+)=488.0895 (Calculated for C$_{20}$H$_{22}$F$_2$N$_2$O$_6$S$_2$=488.0887).

N-((cis)-4-(2,6-difluorophenylsulfonamido)cyclohexyl)-2,3-dihydrobenzo[b][1,4]dioxine-6-sulfonamide (38)

$^1$H NMR (400 MHz, CDCl$_3$) δ: 7.49 (m, 1H), 7.35 (m, 2H), 7.00 (m, 2H), 6.90 (d, 1H, J=8.61 Hz), 5.21 (m, 1H), 4.85 (m, 1H), 4.29 (m, 4H), 3.42 (b, 1H), 3.20 (b, 1H), 1.45-1.65 (m, 8H). LC/MS: Method 1, retention time: 5.507 min; Method 2, retention time: 3.803 min. HRMS: m/z (M+)=488.0885 (Calculated for C$_{20}$H$_{22}$F$_2$N$_2$O$_6$S$_2$=488.0887).

N-(1-(2,6-difluorophenylsulfonyl)piperidin-4-yl)-2,3-dihydrobenzo[b][1,4]dioxine-6-sulfonamide (39)

$^1$H NMR (CDCl$_3$) δ: 7.50 (m, 1H), 7.33 (m, 2H), 7.00 (m, 2H), 6.93 (d, 1H, J=8.61 Hz), 4.86 (d, 1H, J=6.65 Hz), 4.30 (m, 4H), 3.67 (m, 2H), 3.22 (m, 1H), 2.83 (t, 2H, J=10.37 Hz), 1.86 (m, 2H), 1.56 (m, 2H). LC/MS: Method 1, retention time: 5.514 min; Method 2, retention time: 3.825 min. HRMS: m/z (M+)=474.0744 (Calculated for C$_{19}$H$_{20}$F$_2$N$_2$O$_6$S$_2$=474.0731)

N-(1-(2,3-dihydrobenzo[b][1,4]dioxin-6-ylsulfonyl)piperidin-4-yl)-2,6-difluorobenzenesulfonamide (40)

$^1$H NMR (400 MHz, CDCl$_3$) δ: 7.50 (m, 1H), 7.31 (m, 2H), 7.01 (m, 2H), 6.96 (d, 1H, J=8.6 Hz), 4.96 (d, 1H, J=6.65 Hz), 4.37 (m, 4H), 3.64 (m, 2H), 3.20 (m, 1H), 2.80 (t, 2H, J=10.4 Hz), 1.89 (m, 2H), 1.55 (m, 2H). LC/MS: Method 1, retention time: 5.511 min; Method 2, retention time: 3.825 min. HRMS: m/z (M+)=474.0733 (Calculated for C$_{19}$H$_{20}$F$_2$N$_2$O$_6$S$_2$=474.0731).

N-(1-(2,6-difluorophenylsulfonyl)pyrrolidin-3-yl)-2,3-dihydrobenzo[b][1,4]dioxine-6-sulfonamide (41)

$^1$H NMR (400 MHz, CDCl$_3$) δ: 7.52 (m, 1H), 7.33 (m, 2H), 7.03 (m, 2H), 6.96 (d, 1H, J=8.6 Hz), 4.85 (b, 1H), 4.32 (m, 4H), 3.84 (m, 1H), 3.53 (m, 2H), 3.42 (m, 1H), 3.19 (q, 1H, J=4.7 Hz), 2.11 (m, 1H), 1.87 (m, 1H). LC/MS: Method 1, retention time: 5.339 min; Method 2, retention time: 3.789 min. HRMS: m/z (M+)=460.0578 (Calculated for C$_{18}$H$_{18}$F$_2$N$_2$O$_6$S$_2$=460.0574).

N-(1-(2,3-dihydrobenzo[b][1,4]dioxin-6-ylsulfonyl)pyrrolidin-3-yl)-2,6-difluorobenzenesulfonamide (42)

$^1$H NMR (400 MHz, CDCl$_3$) δ: 7.51 (m, 1H), 7.33 (m, 2H), 7.03 (m, 2H), 6.95 (d, 1H, J=8.6 Hz), 5.02 (b, 1H), 4.31 (m,

4H), 3.88 (m, 1H), 3.59 (m, 2H), 3.44 (m, 1H), 3.16 (q, 1H, J=4.7 Hz), 2.08 (m, 1H), 1.88 (m, 1H). LC/MS: Method 1, retention time: 5.339 min; Method 2, retention time: 3.792 min. HRMS: m/z (M+)=460.0587 (Calculated for $C_{18}H_{18}F_2N_2O_6S_2$=460.0574).

N-((1-(2,6-difluorophenylsulfonyl)azetidin-3-yl)methyl)-2,3-dihydrobenzo[b][1,4]dioxine-6-sulfonamide (43)

$^1$H NMR (400 MHz, CDCl$_3$) δ: 7.53 (m, 1H), 7.30 (m, 2H), 7.05 (m, 2H), 6.94 (d, 1H, J=8.6 Hz), 4.40 (m, 1H) 4.30 (m, 4H), 4.04 (t, 2H, J=8.2 Hz), 3.66 (dd, 2H, J=8.4, 5.65 Hz), 3.08 (t, 2H, J=6.7 Hz), 2.69 (m, 1H). LC/MS: Method 1, retention time: 5.295 min; Method 2, retention time: 3.780 min. HRMS: m/z (M+)=460.0582 (Calculated for $C_{18}H_{18}F_2N_2O_6S_2$=460.0574).

N-((1-(2,3-dihydrobenzo[b][1,4]dioxin-6-ylsulfonyl)azetidin-3-yl)methyl)-2,6-difluorobenzenesulfonamide (44)

$^1$H NMR (400 MHz, CDCl$_3$) δ: 7.51 (m, 1H), 7.27 (m, 2H), 7.00 (m, 3H), 5.23 (t, 1H, J=6.06 Hz), 4.31 (m, 4H), 3.78 (t, 2H, J=8.22 Hz), 3.47 (dd, 2H, J=8.41, 5.67 Hz), 3.10 (t, 2H, J=6.7 Hz), 2.62 (m, 1H). LC/MS: Method 1, retention time: 5.234 min; Method 2, retention time: 3.767 min. HRMS: m/z (M+)=460.0583 (Calculated for $C_{18}H_{18}F_2N_2O_6S_2$=460.0574).

(S)-4-(2,6-difluorophenylsulfonyl)-1-(2,3-dihydrobenzo[b][1,4]dioxin-6-ylsulfonyl)-2-methylpiperazine (45)

$^1$H NMR (400 Hz, CDCl$_3$) δ: 7.55 (m, 1H), 7.26 (m, 2H), 7.04 (m, 2H), 6.92 (m, 1H), 4.30 (m, 4H), 4.21 (m, 1H), 3.84 (d, 1H, J=12.1 Hz), 3.72 (d, 1H, J=12.9 Hz), 3.61 (d, 1H, J=12.1 Hz), 3.24 (td, 1H, J=12.5, 3.13 Hz), 2.86 (dd, 1H, J=12.1, 2.74 Hz), 2.72 (td, 1H, J=11.9, 3.1 Hz), 1.13 (d, 3H, J=6.7 Hz). LC/MS: Method 1, retention time: 5.873 min; Method 2, retention time: 3.905 min. HRMS: m/z (M+)=474.0736 (Calculated for $C_{19}H_{20}F_2N_2O_6S_2$=474.0731).

(R)-4-(2,6-difluorophenylsulfonyl)-1-(2,3-dihydrobenzo[b][1,4]dioxin-6-ylsulfonyl)-2-methylpiperazine (46)

$^1$H NMR (400 MHz, CDCl$_3$) δ: 7.55 (m, 1H), 7.26 (m, 2H), 7.04 (m, 2H), 6.92 (m, 1H), 4.30 (m, 4H), 4.21 (m, 1H), 3.84 (d, 1H, J=12.1 Hz), 3.72 (d, 1H, J=12.9 Hz), 3.61 (d, 1H, J=12.1 Hz), 3.24 (td, 1H, J=12.5, 3.1 Hz), 2.86 (dd, 1H, J$_1$=12.1, 2.7 Hz), 2.72 (td, 1H, J=11.9, 13.0 Hz), 1.13 (d, 3H, J=6.7 Hz). LC/MS: Method 1, retention time: 5.872 min; Method 2, retention time: 3.905 min. HRMS: m/z (M+)=474.0736 (Calculated for $C_{19}H_{20}F_2N_2O_6S_2$=474.0731).

(S)-1-(2,6-difluorophenylsulfonyl)-4-(2,3-dihydrobenzo[b][1,4]dioxin-6-ylsulfonyl)-2-methylpiperazine (48)

$^1$H NMR (400 MHz, CDCl$_3$) δ: 7.50 (m, 1H), 7.22 (m, 2H), 7.00 (m, 3H), 4.33 (m, 5H), 3.92 (d, 1H, J=13.7 Hz), 3.70 (d, 1H, J=11.4 Hz), 3.50 (d, 1H, J=11.4 Hz), 3.38 (m, 1H), 2.53 (dd, 1H, J=11.4, 3.5 Hz), 2.39 (td, 1H, J=11.8, 3.3 Hz), 1.22 (d, 3H, J=7.0 Hz). LC/MS: Method 1, retention time: 5.912 min; Method 2, retention time: 3.910 min. HRMS: m/z (M+)=474.0726 (Calculated for $C_{19}H_{20}F_2N_2O_6S_2$=474.0731).

(R)-1-(2,6-difluorophenylsulfonyl)-4-(2,3-dihydrobenzo[b][1,4]dioxin-6-ylsulfonyl)-2-methylpiperazine (47)

$^1$H NMR (400 MHz, CDCl$_3$) δ: 7.50 (m, 1H), 7.22 (m, 2H), 7.00 (m, 3H), 4.33 (m, 5H), 3.92 (d, 1H, J=13.7 Hz), 3.70 (d, 1H, J=11.4 Hz), 3.50 (d, 1H, J=11.4 Hz), 3.38 (m, 1H), 2.53 (dd, 1H, J=11.4, 3.5 Hz), 2.39 (td, 1H, J=11.8, 3.3 Hz), 1.22 (d, 3H, J=7.0 Hz). LC/MS: Method 1, retention time: 5.910 min; Method 2, retention time: 3.912 min. HRMS: m/z (M+)=474.0727 (Calculated for $C_{19}H_{20}F_2N_2O_6S_2$=474.0731).

Synthesis of oxo-piperazine Derivatives 49 and 50
Exemplified by 49

Method A was used to introduce the 2,6-difluorosulfonyl group.

4-(2,6-difluorophenylsulfonyl)piperazin-2-one (500 mg, 1.81 mmol, 1 equiv.) was dissolved in THF (5 mL) and cooled to −78° C. LHMDS (1.85 mL of 1.0 M THF solution, 1.9 mmol, 1.05 equiv.) was then added dropwise and the solution stirred at −78° C. for 1 h. A solution of 2,3-dihydrobenzo[b][1,4]dioxine-6-sulfonyl chloride (510 mg, 2.17 mmol, 1.2 equiv.) in THF (2 mL) was then added drop-wise to the cold solution. The reaction was stirred at −78° C. for 15 minutes then allowed to warm to room temperature and stirred an additional 1 h. The reaction was carefully quenched with saturated aqueous ammonium chloride (~5 mL), and diluted with ethyl acetate (~15 mL). The organic layer was washed twice with saturated aqueous ammonium chloride, once with brine, dried over sodium sulfate and concentrated. The residue was dissolved in DMSO and purified by reverse phase HPLC.

4-(2,6-difluorophenylsulfonyl)-1-(2,3-dihydrobenzo[b][1,4]dioxin-6-ylsulfonyl)piperazin-2-one (49)

$^1$H NMR (400 Hz, CDCl$_3$) δ: 7.58 (m, 1H), 7.29 (m, 3H), 7.03 (m, 2H), 4.31 (m, 4H), 4.07 (m, 2H), 3.81 (s, 2H), 3.47 (m, 2H). LC/MS: Method 1, retention time: 5.631 min; Method 2, retention time: 3.858 min. HRMS: m/z (M+)=474.0372 (Calculated for $C_{18}H_{16}F_2N_2O_7S_2$=474.0367).

1-(2,6-difluorophenylsulfonyl)-4-(2,3-dihydrobenzo[b][1,4]dioxin-6-ylsulfonyl)piperazin-2-one (50)

$^1$H NMR (400 MHz, CDCl$_3$) δ: 7.58 (m, 1H), 7.29 (m, 3H), 7.03 (m, 2H), 4.33 (m, 4H), 4.07 (m, 2H), 3.78 (s, 2H), 3.44 (m, 2H). LC/MS: Method 1, retention time: 5.612 min; Method 2, retention time: 3.849 min. HRMS: m/z (M+)=474.0366 (Calculated for $C_{18}H_{16}F_2N_2O_7S_2$=474.0367).

Compounds of formula II were prepared as follows:

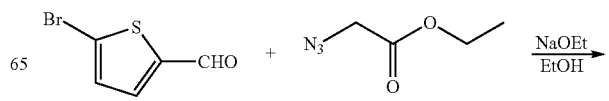

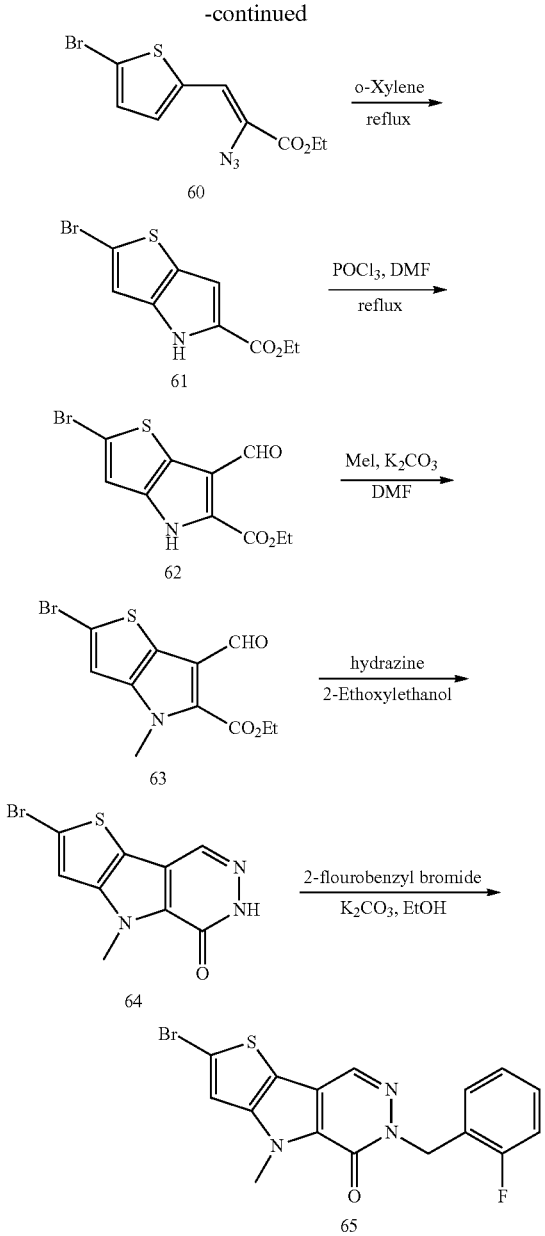

Ethyl 2-azido-3-(5-bromothiophen-2-yl)acrylate (60)

A solution of sodium (2.76 g, 120 mmol) in absolute EtOH (120 mL) was cooled in an ice-bath and a mixture of 5-bromo-2-formylthiophene (5.73 g, 30 mmol) and ethyl azidoacetate (15.49 g, 120 mmol) was added dropwise during 30 min period. The bath was removed and the reaction mixture was stirred at room temperature for another 30 min. A cold solution of saturated aqueous NH₄Cl solution (100 mL) was added and the resulting solution was extracted with diethyl ether (3×100 mL) and the combined organic layers were washed with brine (200 mL), dried over Na₂SO₄. After removing diethyl ether under reduced pressure, the crude product was purified by column chromatography (EtOAc/Hexane: 1/50) to give acrylate 60 (3.81 g, 42%) as a light yellow solid.

Ethyl 2-bromo-4H-thieno[3,2-b]pyrrole-5-carboxylate (61)

Acrylate 60 (3.81 g, 12.6 mmol) in o-xylene was refluxed for 20 min. After removing the o-xylene, the crude product was purified by column chromatography (EtOAc/Hexane: 1/10) to give carboxylate 61 (2.83 g, 82%) as a white solid.

Ethyl 2-bromo-6-formyl-4H-thieno[3,2-b]pyrrole-5-carboxylate (62)

To DMF (2.05 mL) cooled by ice/water was added POCl₃ dropwise and the mixture was stirred for 30 min. A solution of carboxylate 61 (1.96 g, 7.15 mmol) in DMF (2.5 mL) was added at this temperature and the mixture was allowed to warm to room temperature then heated to 60° C. After 16 h, the reaction mixture was cooled to room temperature. and poured into ice/water. The mixture was extracted with EtOAc (3×20 mL) and the combined organic layers were washed with aqueous saturated NaHCO₃ and brine, dried over Na₂SO₄. After removed the organic solvent, the residue was purified by column chromatography (EtOAc/Hexane: 1/4) to give the desired aldehyde 62 (1.62 g, 75%) as a white solid.

Ethyl 2-bromo-6-formyl-4-methyl-4H-thieno[3,2-b] pyrrole-5-carboxylate (63)

To a solution of aldehyde 62 (515 mg, 1.70 mmol) in DMF (5 mL) was added potassium carbonate (707 mg, 5.12 mmol) and iodomethane (0.27 mL, 3.40 mmol) and the resulting mixture was stirred at room temperature for 2 hr. To the mixture was added H₂O (30 mL) and EtOAc (50 mL) and the organic layer was separated and washed with brine and dried over Na₂SO₄. After removing the organic solvent under reduced pressure, the residue was purified by column chromatography (EtOAc/Hexane: 1/8) to give the desired N-methylated product 63 (440 mg, 82%) as a white solid.

2-Bromo-4-methyl-4H-thieno[3,2-b]pyrrole[3,2-d] pyridazinone (64)

The N-methylated product 63 (420 mg, 1.33 mmol) was dissolved in warm 2-ethoxyethanol (26 mL). To a refluxed solution of hydrazine monohydrate (1 mL, 31.9 mmol) and 2-ethoxyethanol (5 mL) under nitrogen was added prepared N-methylated product 62 solution dropwise over a 2 hr period and the solution continued to reflux for additional 1 hr. After cooling to room temperature, about half of the 2-ethoxyethanol was removed under reduced pressure and the remaining solution was refrigerated at −20° C. overnight. The precipitate was filtered and washed with 2-ethoxyethanol to give desired pyridazinone 64 (354 mg, 94%) as a white solid.

2-Bromo-4-methyl-6-[(2-fluorophenyl)methyl]-4H-thieno[3,2-b]pyrrole[3,2-d]pyridazinone (65)

To a solution of pyridazinone 63 (354 mg, 1.25 mmol) in EtOH (5 mL) was added potassium carbonate (1.02 g, 7.35 mmol) and 2-fluorobenzyl bromide (0.94, 4.98) and the resulting mixture was heated at 60° C. for 2 hr. After cooling to room temperature, to the mixture H₂O (20 mL) and EtOAc (50 mL) was added and the organic layer was separated and washed with brine and dried over Na₂SO₄. After removing the solvent under reduced pressure, the residue was purified by column chromatography (EtOAc/Hexane: 1/4) to give desired pyridazinone 65 (371 mg, 76%) as a white solid. This compound was used as a versatile intermediate underwent a variety of transformations as described below.

The procedure for the synthesis of this lead compound is the same as pyridazinone 65. We also developed a more efficient, generalized procedure for the last step of coupling the pyridazinone 64 with 2-fluorobenzyl bromide. This procedure was adopted for the syntheses of analogue 89-92, 102 and 103-121.

2,4-Methyl-6-[(2-fluorophenyl)methyl]-4H-thieno[3,2-b]pyrrole[3,2-d]pyridazinone (NCGC00031955) (66)

To a solution of 2,4-dimethyl-4H-thieno[3,2-b]pyrrole[3,2-d]pyridazinone (20 mg, 0.086 mmol) in DMF (0.5 mL) was added potassium tert-butoxide (1.5 eq.) and 2-fluorobenzyl bromide (2 eq.) and the mixture was stirred for 1 h at room temperature. The mixture was filtered through a frit attached to a syringe and washed with DMF and the total filtrate was 2 mL. The DMF solution was directly subjected to purification by preparative HPLC to give the desired product as a white solid. For other analogues prepared in this way, the yield ranges from 35% to 90%. $^1$H NMR (400 MHz, CDCl$_3$) δ 8.20 (s, 1H), 7.26-7.19 (m, 2H), 7.09-7.02 (m, 2H), 6.92 (q, 1H, J=1.2 Hz), 5.53 (s, 2H), 4.27 (s, 3H), 2.64 (d, 3H, J=1.2 Hz); LC/MS: Method 1, retention time: 6.313 min; Method 2, retention time: 3.992 min; HRMS: m/z (M+H$^+$)=328.0925 (Calculated for C$_{17}$H$_{15}$FN$_3$OS=328.0920).

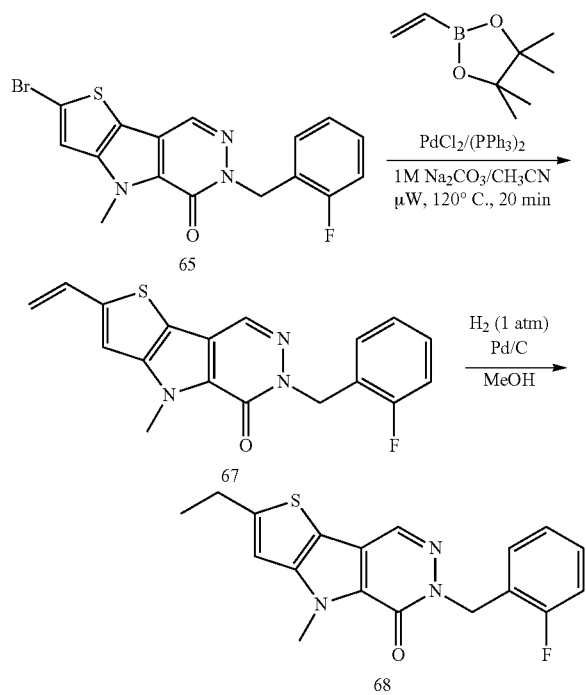

2-Vinyl-4-methyl-6-[(2-fluorophenyl)methyl]-4H-thieno[3,2-b]pyrrole[3,2-d]pyridazinone (67)

To a microwave vessel was added bromide 65 (24 mg, 0.06 mmol), vinyl boronic acid pinacol ester (28 mg, 0.18 mmol), Pd(PPh$_3$)$_2$Cl$_2$ (8.4 mg, 0.012 mmol, 20 mol %), 1M aqueous Na$_2$CO$_3$ solution (0.16 mL) and CH$_3$CN (0.16 mL). The mixture was purged with nitrogen for 1 min and the vessel was capped. The vessel was subjected to be microwaved at 120° C. for 20 min. After cooling down, the cap was removed and the mixture was partitioned in EtOAc (10 mL) and H$_2$O (5 mL). The organic layer was separated, washed with brine and dried (MgSO$_4$). After removing EtOAc under reduced pressure, the crude product was directly purified by preparative TLC (EtOAc/Hexane: 1/4) to give alkene 67 (16 mg, 75%) as a white solid.

2-Ethyl-4-methyl-6-[(2-fluorophenyl)methyl]-4H-thieno[3,2-b]pyrrole[3,2-d]pyridazinone (68)

To a solution of compound 67 (10 mg, 0.32 mmol) in MeOH (1 mL) was added 10 wt % Pd/C (5 mg) and stirred under H$_2$ (1 atm) for 2 h. The catalyst was filtered and MeOH was removed under reduced pressure to give a residue which was purified by column chromatography (EtOAc/Hexane: 1/4) to give the desired product 68 (8 mg, 80%) as a white solid. $^1$H NMR (400 MHz, CDCl$_3$) δ 8.19 (s, 1H), 7.24-7.17 (m, 2H), 7.07-7.00 (m, 2H), 6.80 (t, 1H, J=1.0 Hz), 5.51 (s, 2H), 4.26 (s, 3H), 2.95 (qd, 2H, J=7.8, 1.0 Hz), 1.37 (t, 3H, J=7.8 Hz); LC/MS: Method 1, retention time: 6.658 min; Method 2, retention time: 4.052 min; HRMS: m/z (M+H$^+$)= 342.1073 (Calculated for C$_{18}$H$_{17}$FN$_3$OS=342.1076).

2-Isopropyl-4-methyl-6-[(2-fluorophenyl)methyl]-4H-thieno[3,2-b]pyrrole[3,2-d]pyridazinone (69)

Analogue 69 was prepared in the same procedure as analogue 68. $^1$H NMR (400 MHz, CDCl$_3$) δ 8.19 (s, 1H), 7.28-7.17 (m, 2H), 7.07-7.00 (m, 2H), 6.81 (d, 1H, J=0.8 Hz), 5.51 (s, 2H), 4.26 (s, 3H), 3.28-3.20 (m, 1H), 1.39 (d, 6H, J=6.8 Hz); LC/MS: Method 1, retention time: 6.942 min; Method 2, retention time: 4.106 min; HRMS: m/z (M+H$^+$)=356.1230 (Calculated for C$_{19}$H$_{19}$FN$_3$OS=356.1233).

4-Methyl-6-[(2-fluorophenyl)methyl]-4H-thieno[3,2-b]pyrrole[3,2-d]pyridazinone (70)

To a solution of 65 (20 mg, 0.051 mmol) in MeOH (5 mL) was added 10 wt % Pd/C (10 mg) and stirred under H$_2$ (1 atm) for 1 h. The catalyst was filtered through a pad of Celite™ and MeOH was removed under reduced pressure. The residue was purified by column chromatography (EtOAc/Hexane: 1/4) to give the de-brominated product 70 (13 mg, 81%) as a white solid. $^1$H NMR (400 MHz, CDCl$_3$) δ 8.27 (s, 1H), 7.55 (d, 1H, J=5.2 Hz), 7.27-7.21 (m, 2H), 7.10 (d, 1H, J=5.2 Hz), 7.09-7.04 (m, 2H), 5.54 (s, 2H), 4.34 (s, 3H); LC/MS: Method 1, Retention time: 5.995 min; Method 2, retention time: 3.925 min; HRMS: m/z (M+H$^+$)=314.0760 (Calculated for C$_{16}$H$_{13}$FN$_3$OS=314.0763).

2-Methoxy-4-methyl-6-[(2-fluorophenyl)methyl]-4H-thieno[3,2-b]pyrrole[3,2-d]pyridazinone (71)

To anhydrous MeOH (0.27 mL) was slowly added sodium pieces (16 mg, 0.69 mmol). After ceasing to produce H$_2$, excess MeOH was removed under reduced pressure. To freshly prepared sodium methoxide was added 65 (34 mg, 0.087 mmol), CuI (3.3 mg, 0.017 mmol) and dioxane (0.3 mL) and the mixture was refluxed for 16 h. After cooling to r.t., the mixture was partitioned in water and EtOAc and the aqueous layer was further extracted with EtOAc. The organic layers were washed with brine and dried over Na$_2$SO$_4$. After the removal of organic solvent, the residue was directly purified by preparative HPLC to give desired methoxy substituted analogue 71 (7 mg, 44% based on recovered starting material)

and recovered starting material (16 mg). $^1$H NMR (400 MHz, CDCl$_3$) δ 8.14 (s, 1H), 7.26-7.20 (m, 2H), 7.09-7.03 (m, 2H), 6.27 (s, 1H), 5.53 (s, 2H), 4.25 (s, 3H), 4.01 (s, 3H); LC/MS: Method 1, retention time: 6.169 min; Method 2, retention time: 3.939 min; HRMS: m/z (M+H$^+$)=344.0868 (Calculated for C$_{17}$H$_{15}$FN$_3$O$_2$S=344.0869).

2-Methylthio-4-methyl-6-[(2-fluorophenyl)methyl]-4H-thieno[3,2-b]pyrrole[3,2-d]pyridazinone (72)

To a solution of 65 (50 mg, 0.13 mmol) in DMF (0.5 mL) was added copper (I) bromide (18 mg, 0.13 mmol) and sodium thiomethoxide (27 mg, 0.38 mmol) and the mixture was heated at 140° C. for 2 h. After cooling to room temperature, the mixture was partitioned in EtOAc (10 mL) and water (10 mL) and the organic layer was separated, washed with brine and dried over Na$_2$SO$_4$. After the removal of organic solvent, the residue was purified by preparative HPLC to give the desired thiomethyl analogue 71 (16 mg, 35%) as a white solid. $^1$H NMR (400 MHz, CDCl$_3$) δ 8.18 (s, 1H), 7.25-7.19 (m, 2H), 7.09 (s, 1H), 7.07-7.02 (m, 2H), 5.51 (s, 2H), 4.26 (s, 3H), 2.58 (s, 3H); LC/MS: Method 1, retention time: 6.570 min; Method 2, retention time: 4.063 min; HRMS: m/z (M+H$^+$)=360.0637 (Calculated for C$_{17}$H$_{15}$FN$_3$OS$_2$=360.0641).

2-Methylsulfinyl-4-methyl-6-[(2-fluorophenyl)methyl]-4H-thien o[3,2-b]pyrrole[3,2-d]pyridazinone (73) and 2-Methylsulfonyl-4-methyl-6-[(2-fluorophenyl)methyl]-4H-thieno[3,2-b]pyrrole[3,2-d]pyridazinone (74)

To a solution of 7 (25 mg, 0.069 mmol) in DCM (2 mL) was added mCPBA (1.5 eq.) and the mixture was stirred at room temperature for 2 h. The mixture was diluted with DCM (10 mL) and washed with saturated aqueous NaHCO$_3$ and dried over Na$_2$SO$_4$. After the removal of solvent, the crude product was purified by preparative HPLC to give sulfoxide 73 (10 mg, 40%) and sulfone 74 (9 mg, 36%). 73: $^1$H NMR (400 MHz, CDCl$_3$) δ 8.28 (s, 1H), 7.57 (s, 1H), 7.30-7.22 (m, 2H), 7.10-7.04 (m, 2H), 5.53 (s, 2H), 4.34 (s, 3H), 3.01 (s, 3H); LC/MS: Method 1, retention time: 4.967 min; Method 2, retention time: 3.683 min; HRMS: m/z (M+H$^+$)=376.0587 (Calculated for C$_{17}$H$_{15}$FN$_3$O$_2$S$_2$=376.0590). 74: $^1$H NMR (400 MHz, CDCl$_3$) δ 8.28 (s, 1H), 7.80 (s, 1H), 7.32-7.23 (m, 2H), 7.11-7.04 (m, 2H), 5.53 (s, 2H), 4.36 (s, 3H), 3.26 (s, 3H); LC/MS: Method 1, retention time: 5.621 min; Method 2, retention time: 3.830 min; HRMS: m/z (M+H$^+$) 392.0537 (calculated for C$_{17}$H$_{15}$FN$_3$O$_3$S$_2$$^+$) 392.0539.

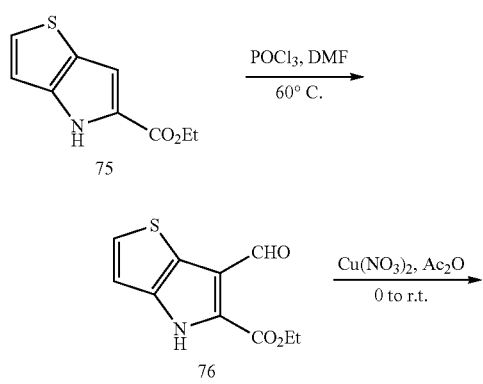

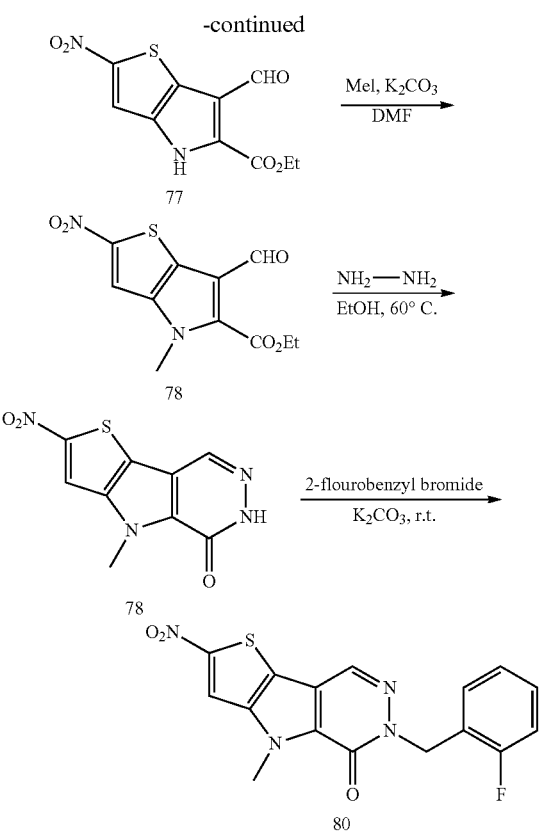

Ethyl 6-formyl-2-nitro-4H-thieno[3,2-b]pyrrole-5-carboxylate (77)

Carboxylate 76 was prepared in the same procedure as 62. Pulverized Cu(NO$_3$)$_2$ hydrate (234 mg, 0.97 mmol) dissolved in acetic anhydride (2 mL) was added dropwise to a solution of 76 (240 mg, 1.08 mmol) dissolved in acetic anhydride (5 mL) cooled by ice/water bath. The addition was completed in 1.5 h and the mixture was then stirred at room temperature for 2 h. The salt was filtered and the filtrate was introduced into ice/water. The mixture was extracted with diethyl ether (3×10 mL) and the combined organic layers were washed with saturated aqueous sodium carbonate solution and dried over MgSO$_4$. After the removal of organic solvent, the residue was purified by column chromatography (EtOAc/Hexane: 1/2) to give the carboxylate 77 (236 mg, 82%) as a light yellow solid.

2-Nitro-4-methyl-6-[(2-fluorophenyl)methyl]-4H-thieno[3,2-b]pyrrole[3,2-d]pyridazinone (80)

Methylated intermediate 78 was prepared as compound 63. To a solution of 77 (150 mg, 0.53 mmol) in EtOH (15 mL) was added hydrazine (0.4 mL, 12.72 mmol) and the solution was stirred for 30 min. Removing the EtOH and excess hydrazine gave the desired pyridazinone 79. To a solution of 79 (133 mg, 0.53 mmol) in DMF (5 mL) was added potassium carbonate (439 mg, 3.18 mmol) and 2-fluorobenzyl bromide (501 mg, 2.65 mmol) and the mixture was stirred at room temperature for 2 h. The mixture was partitioned in EtOAc (30 mL) and water (30 mL) and the organic layer was separated and washed with brine and dried over Na$_2$SO$_4$. After the removal of organic solvent, the residue was directly purified by preparative HPLC to give the nitro substituted analogue 80 (70 mg, 37%) as a light yellow solid. $^1$H NMR (400 MHz, CDCl$_3$) δ 8.27 (s, 1H), 8.06 (s, 1H), 7.35-7.24 (m, 2H), 7.11-7.05 (m, 2H), 5.52 (s, 2H), 4.37 (s, 3H); LC/MS: Method 1, retention time: 6.185 min; Method 2, retention time: 3.978 min; HRMS: m/z (M+H$^+$)=359.0607 (Calculated for C$_{16}$H$_{12}$FN$_4$O$_3$S=359.0614).

2-Acetylamido-4-methyl-6-[(2-fluorophenyl)methyl]-4H-thieno[3,2-b]pyrrole[3,2-d]-pyridazinone (81)

A mixture of 65 (23 mg, 0.059 mmol), CuI (2.2 mg, 0.012 mmol), K$_3$PO$_4$ (28 mg, 0.12 mmol), acetamide (14 mg, 0.24 mmol), trans-N,N'-dimethylcyclohexane-1,2-diamine (3.4 mg, 0.024 mmol) and dioxane (0.5 mL) was sealed in a tube and stirred and heated in an oil bath at 90° C. for 16 h. The mixture was partitioned between water (5 mL) and DCM (5 mL). The aqueous layer was separated and further extracted with DCM (2×5 mL) and the combined organic layers were washed with brine and dried over Na$_2$SO$_4$. After the removal of organic solvent, the residue was directly purified by preparative HPLC to give 81 (11 mg, 51%) as a white solid. $^1$H NMR (400 MHz, CDCl$_3$) δ 8.21 (s, 1H), 8.01 (br. s, 1H), 7.27-7.20 (m, 2H), 7.09-7.03 (m, 2H), 6.74 (s, 1H), 5.53 (s, 2H), 4.26 (s, 3H), 2.26 (s, 3H); LC/MS: Method 1, retention time: 5.186 min; Method 2, retention time: 3.727 min; HRMS: m/z (M+H$^+$)=371.0974 (Calculated for C$_{18}$H$_{16}$FN$_4$O$_2$S=371.0978).

2-Cyano-4-methyl-6-[(2-fluorophenyl)methyl]-4H-thieno[3,2-b]pyrrole[3,2-d]pyridazinone (82)

To a solution of bromo substituted analogue 65 (20 mg, 0.051 mmol) in DMF (0.3 mL) was added CuCN (9.1 mg, 0.10 mmol, 2 eq.) and the mixture was heated at 140° C. overnight under N$_2$ atmosphere. After cooling to room temperature, the mixture was filtered and washed with EtOAc (10 mL). The filtrate was washed with water, brine and dried over Na$_2$SO$_4$. After the removal of organic solvent, the residue was purified by preparative HPLC to give the desired cyano substituted analogue 82 (7 mg, 40%) as a white solid. $^1$H NMR (400 MHz, CDCl$_3$) δ 8.26 (s, 1H), 7.64 (s, 1H), 7.32-7.23 (m, 2H), 7.10-7.05 (m, 2H), 5.53 (s, 2H), 4.35 (s, 3H); LC/MS: Method 1, retention time: 5.905 min; Method 2, retention time: 3.907 min; HRMS: m/z (M+H$^+$)=339.0712 (Calculated for C$_{17}$H$_{12}$FN$_4$OS=339.0716).

Methyl 4-methyl-6-[(2-fluorophenyl)methyl]-4H-thieno[3,2-b]pyrrole[3,2-d]pyridazinone-2-carboxylate (83)

To a solution of 65 (40 mg, 0.10 mmol) in MeOH (0.37 mL) and DMSO (0.37 mL) was added Pd(OAc)$_2$ (5.7 mg, 0.025 mmol), 1,3-bis(diphenylphosphino)propane (dppp) (10.5 mg, 0.025 mmol) and triethyl-amine (16 µl, 0.11 mmol) and the mixture was exchanged to carbon monoxide (1 atm) atmosphere and heated at 65° C. overnight. After cooling to room temperature, the mixture was taken into EtOAc (10 mL) and washed with water and brine. The organic layer was dried over Na$_2$SO$_4$. After the removal of organic solvent, the residue was purified by preparative HPLC to give the carboxylate 83 (17 mg, 46%) as a white solid. $^1$H NMR (400 MHz, CDCl$_3$) δ 8.28 (s, 1H), 7.84 (s, 1H), 7.30-7.23 (m, 2H), 7.11-7.04 (m, 2H), 5.54 (s, 2H), 4.34 (s, 3H), 3.96 (s, 3H); LC/MS: Method 1, retention time: 6.170 min; Method 2, retention time: 3.949 min; HRMS: m/z (M+H$^+$)=372.0816 (Calculated for C$_{18}$H$_{15}$FN$_3$O$_3$S=372.0818).

2-Formyl-4-methyl-6-[(2-fluorophenyl)methyl]-4H-thieno[3,2-b]pyrrole[3,2-d]pyridazinone (84)

To DMF (52 µl, 0.67 mmol) in DCE (1 mL) cooled by ice/water was added POCl$_3$ (42 µl, 0.46 mmol) and the mixture was stirred at room temperature for 30 min. Analogue 70 (70 mg, 0.22 mmol) in DCE (1.2 mL) was added and the mixture was refluxed for 24 h. After cooling, the mixture was pour into ice/water and extracted with EtOAc (3×10 mL). The combined organic layers were washed with saturated aqueous NaHCO$_3$ and dried over Na$_2$SO$_4$. After the removal of organic solvent, the residue was purified by column chromatography (EtOAc/Hexane: 1/3) to give 84 (19 mg, 25%) as a white solid. $^1$H NMR (400 MHz, CDCl$_3$) δ 10.00 (s, 1H), 8.31 (s, 1H), 7.78 (s, 1H), 7.32-7.23 (m, 2H), 7.10-7.05 (m, 2H), 5.54 (s, 2H), 4.37 (s, 3H); LC/MS: Method 1, retention time: 5.734 min; Method 2, retention time: 3.878 min; HRMS: m/z (M+H$^+$)=342.0708 (Calculated for C$_{17}$H$_{13}$FN$_3$O$_2$S=342.0713).

2-Hydroxylmethyl-4-methyl-6-[(2-fluorophenyl)methyl]-4H-thieno[3,2-b]pyrrole[3,2-d]pyridazinone (85)

The analogue was prepared by reducing the corresponding aldehyde 84 with sodium borohydride in MeOH. The crude product was purified by column chromatography (MeOH/DCM 1/10) to give 85 (10 mg, 99%) as a white solid. $^1$H NMR (400 MHz, CDCl$_3$) δ 8.20 (s, 1H), 7.30-7.22 (m, 2H), 7.10-7.02 (m, 2H), 6.98 (s, 1H), 5.53 (s, 2H), 4.89 (s, 2H), 4.25 (s, 3H), 2.50 (br.s, 1H); LC/MS: Method 1, retention time: 5.143 min; Method 2, retention time: 3.682 min; HRMS: m/z (M+H$^+$)=344.0868 (Calculated for C$_{17}$H$_{15}$FN$_3$O$_2$S=344.0869).

4-Methyl-6-[(2-fluorophenyl)methyl]-4H-thieno[3,2-b]pyrrole[3,2-d]pyridazinone, 2-ylboronic acid (86)

To a solution of tetramethylethylenediamine (36 mg, 0.31 mmol) in THF (1.3 mL) at 15° C. was added isopropylmagnesium chloride (0.16 mL, 2M in THF) and the mixture was stirred for 30 min. Analogue 65 (100 mg, 0.26 mmol) was added as a solid to this mixture and stirred at room temperature for 15 min then cooled to 0° C. To the mixture was added trimethylboronate (57 µl, 0.51 mmol) and the mixture was stirred at 0° C. for another 10 min. The mixture was quenched with 0.1N HCl and extracted with EtOAc (3×5 mL). The combined organic layers were dried over MgSO$_4$. The organic solvent was removed and the residue was directly purified by preparative HPLC to give the boronic acid 86 (39 mg, 43%) as a white solid. $^1$H NMR (400 MHz, CDCl$_3$) δ 8.32 (s, 1H), 7.58 (s, 1H), 7.28-7.20 (m, 2H), 7.12-7.04 (m, 2H), 5.54 (s, 2H), 4.31 (s, 3H), 3.25 (s, 2H); Method 1, retention time: 5.112 min; Method 2, retention time: 3.715 min; HRMS: m/z (M+H$^+$)=358.0833 (Calculated for C$_{16}$H$_{14}$BFN$_3$O$_3$S=358.0833).

2-Acetyl-4-methyl-6-[(2-fluorophenyl)methyl]-4H-thieno[3,2-b]pyrrole[3,2-d]pyridazinone (87)

To a solution of alcohol 88 (10 mg, 0.028 mmol) in DMSO (0.3 mL) was added IBX (24 mg, 0.084 mmol) and the mixture was stirred at room temperature for 2 h. The mixture was partitioned between EtOAc (10 mL) and saturated aqueous NaHCO$_3$ (5 mL). The organic layer was separated and washed with brine and dried over MgSO$_4$. After the removal of organic solvent, the residue was purified by preparative HPLC to give desired ketone (9 mg, 90%) as a white solid. $^1$H NMR (400 MHz, CDCl$_3$) δ 8.28 (s, 1H), 7.71 (s, 1H), 7.31-7.22 (m, 2H), 7.10-7.04 (m, 2H), 5.53 (s, 2H), 4.36 (s, 3H), 2.65 (s, 3H); LC/MS: Method 1, retention time: 5.383 min; Method 2, retention time: 3.888 min; HRMS: m/z (M+H$^+$)= 356.0868 (Calculated for C$_{18}$H$_{15}$FN$_3$O$_2$S=356.0869).

2-(2-hydroxylpropyl)-4-methyl-6-[(2-fluorophenyl)methyl]-4H-thieno[3,2-b]pyrrole-[3,2-d]pyridazinone (88)

To a solution of tetramethylethylenediamine (12 mg, 0.10 mmol) in THF (0.4 mL) at 15° C. was added isopropylmagnesium chloride (0.05 mL, 2M in THF, 0.10 mmol) and the mixture was stirred for 30 min. Bromo substituted analogue 65 (30 mg, 0.076 mmol) was added as a solid at this temperature and the mixture was further stirred at r.t. for 15 min then cooled to 0° C. The Grignard reagent intermediated was treated with excess cold acetaldehyde and the mixture was stirred at 0° C. for 10 min. After quenching the reaction with saturated aqueous NH$_4$Cl, the mixture was partitioned between water (5 mL) and EtOAc (5 mL) and the aqueous layer was extracted with EtOAc (2×5 mL) and the combined organic layer were washed with brine and dried over Na$_2$SO$_4$. After the removal of organic solvent, the residue was purified by preparative HPLC to give 88 (6.8 mg, 23%) as a white solid. $^1$H NMR (400 MHz, CDCl$_3$) δ 8.18 (s, 1H), 7.29-7.21 (m, 2H), 7.10-7.03 (m, 2H), 6.92 (s, 1H), 5.53 (s, 2H), 5.15-5.08 (m, 1H), 4.21 (s, 3H), 2.63 (d, 1H, J=6.4 Hz), 1.65 (d, 3H J=6.4 Hz); LC/MS: Method 1, retention time: 5.381 min; Method 2, retention time: 3.769 min; HRMS: m/z (M+H$^+$)= 358.1024 (Calculated for C$_{18}$H$_{17}$FN$_3$O$_2$S=358.1026).

Analogues 89-91 were prepared in the same procedure as 66. For analogue 89, the nitrogen on the pyrrole ring was protected with Boc, which was removed under acidic condition.

2-Methyl-6-[(2-fluorophenyl)methyl]-4H-thieno[3,2-b]pyrrole[3,2-d]pyridazinone (89)

$^1$H NMR (400 MHz, CDCl$_3$) δ 11.52 (br.s, 1H), 8.31 (s, 1H), 7.28-7.20 (m, 2H), 7.14-7.02 (m, 2H), 6.74 (q, 1H, J=0.8 Hz), 5.65 (s, 2H), 2.62 (d, 3H, J=0.8 Hz); LC/MS: Method 1, retention time: 5.540 min; Method 2, retention time: 3.806 min; HRMS: m/z (M+H$^+$)=314.0761 (Calculated for C$_{16}$H$_{13}$FN$_3$OS=314.0763)

2-Methyl-4-ethyl-6-[(2-fluorophenyl)methyl]-4H-thieno[3,2-b]pyrrole[3,2-d]pyridazinone (90)

$^1$H NMR (400 MHz, CDCl$_3$) δ 8.24 (s, 1H), 7.26-7.20 (m, 2H), 7.09-7.02 (m, 2H), 6.82 (q, 1H, J=0.8 Hz), 5.53 (s, 2H), 4.75 (q, 2H, J=7.2 Hz), 2.65 (d, 3H, 0.8 Hz), 1.48 (t, 3H, J=7.2 Hz); LC/MS: Method 1, retention time: 6.630 min; Method 2, retention time: 4.052 min; HRMS: m/z (M+H$^+$)=342.1075 (Calculated for C$_{18}$H$_{17}$FN$_3$OS$_2$=342.1076).

2-Methyl-4-isopropyl-6-[(2-fluorophenyl)methyl]-4H-thieno[3,2-b]pyrrole[3,2-d]pyridazinone (91)

$^1$H NMR (400 MHz, CDCl$_3$) δ 8.22 (s, 1H), 7.26-7.19 (m, 2H), 7.08-7.02 (m, 2H), 6.93 (q, 1H, J=1.0 Hz), 6.25-6.14 (m, 1H), 5.53 (s, 2H), 2.65 (d, 3H, J=1.0 Hz), 1.58 (d, 6H, J=7.2 Hz); LC/MS: Method 1, retention time: 6.897 min; Method 2, retention time: 4.100 min; HRMS: m/z (M+H$^+$)=356.1232 (Calculated for C$_{19}$H$_{19}$FN$_3$OS$_2$=356.1233).

2,4,8-Methyl-6-[(2-fluorophenyl)methyl]-4H-thieno[3,2-b]pyrrole[3,2-d]-pyridazinone (92)

To a solution of carboxylate 79 (251 mg, 1.00 mmol) in THF (5 mL) cooled to −78° C. was added 3M MeMgCl solution in THF (0.33 mL, 1 mmol). After work-up, the crude product was purified by column chromatography (EtOAc/Hexane: 1/2) to give the desired secondary alcohol 93 (135 mg, 54%) as a white solid. The secondary alcohol was oxidized using IBX to the methyl ketone 94 (95%) in the same procedure as preparing analogue 87. Following the same procedure for preparing 66, analogue 92 was obtained. $^1$H NMR (400 MHz, CDCl$_3$) δ 7.26-7.16 (m, 2H), 7.08-7.01 (m, 2H), 6.82 (q, 1H, J=1.0 Hz), 5.49 (s, 2H), 4.27 (s, 3H), 2.65 (d, 3H, J=1.0 Hz), 2.56 (s, 3H); LC/MS: Method 1, retention time: 6.659 min; Method 2, retention time: 3.762 min; HRMS: m/z (M+H$^+$)=342.1077 (Calculated for C$_{18}$H$_{17}$FN$_3$OS=342.1076).

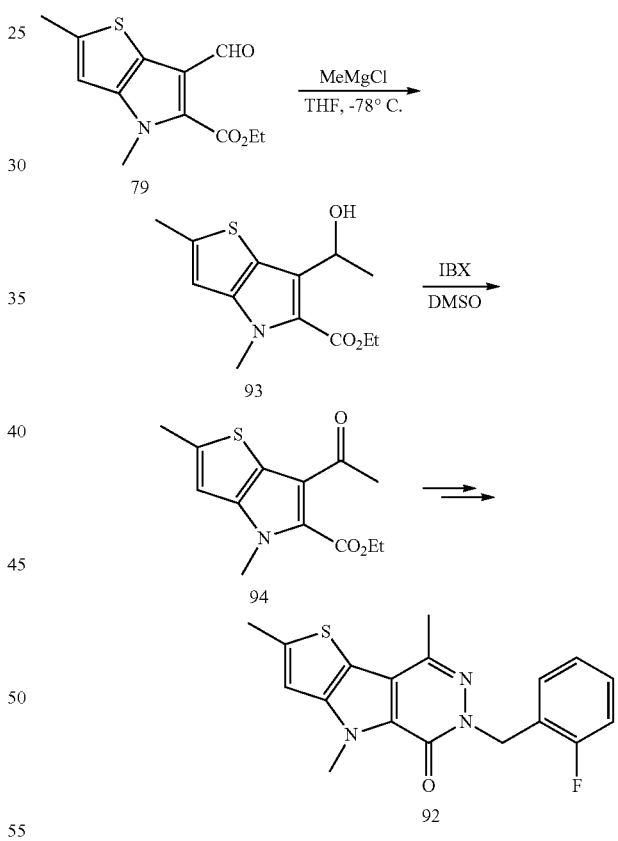

Ethyl-6-nitro-4H-thieno[3,2-b]pyrrole-5-carboxylate (95)

Pulverized Cu(NO$_3$)$_2$ hydrate (953 mg, 4.10 mmol) dissolved in acetic anhydride (8.2 mL) was added dropwise to a solution of carboxylate 96 dissolved in acetic anhydride (10 mL) at 0° C. The addition was completed in 1.5 h and the mixture was then stirred at r.t. for 2 h. After filtration the organic layer was poured over ice and extracted with diethyl ether (3×30 mL). The combined organic layers were washed with saturated aqueous sodium carbonate solution and dried over MgSO$_4$. After the removal of organic solvent, the residue was purified by column chromatography (EtOAc/Hexane: 1/6) to give the desired nitration product 94 (148 mg, 12%) as a light yellow solid along with another nitration product 95 (300 mg, 25%).

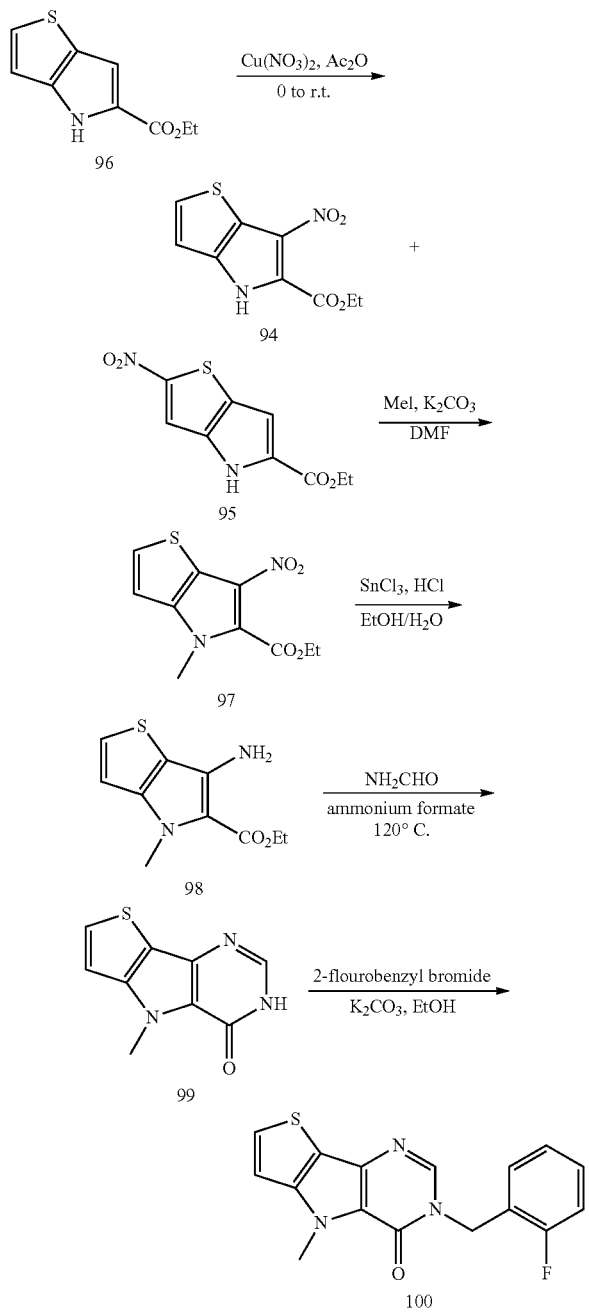

Ethyl-6-amino-4-methyl-4H-thieno[3,2-b]pyrrole-5-carboxylate (98)

Compound 94 was treated with iodomethane and potassium carbonate to give the N-methylated product 97. To 97 (60 mg, 0.24 mmol) in EtOH (1.3 mL) was added tin(II) chloride (358 mg, 1.89 mmol). Concentrated HCl (1.3 mL) was added dropwise at 0° C. and the mixture was heated at 35° C. for 2 h. LC/MS found the reaction was completed and formed the desired amine. After the mixture was cooled to room temperature, neutralized the mixture to pH=9 with 1N aqueous NaOH solution and extracted with EtOAc. The combined extracts were washed with brine and dried over Na$_2$SO$_4$. After the removal of organic solvent, the crude product of amine 98 (49 mg) was directly used for the next step.

4-Methyl-4H-thieno[3,2-b]pyrrole[3,2-d]pyrimidinone (99)

To amine 98 (49 mg, 0.22 mmol) was added ammonium formate (22 mg, 0.35 mmol) and formamide (0.3 mL) and the mixture was heated at 120° C. in sealed tube for 16 h. After cooling to room temperature, the mixture was poured into ice/water and extracted with EtOAc (3×10 mL) and the combined organic layers were washed with brine and dried over Na$_2$SO$_4$. Removing the solvent afforded the crude product pyrimidinone 99 (40 mg) which was directly used for the next step.

4-Methyl-6-[(2-fluorophenyl)methyl]-4H-thieno[3,2-b]pyrrole[3,2-d]pyrimidinone (100)

To pyrimidinone 99 (40 mg, 0.20 mmol) in EtOH (2 mL) was added potassium carbonate (38 mg, 0.27 mmol) and 2-fluorobenzyl bromide (44 mg, 0.24 mmol) and the mixture was refluxed for 1 h. After cooling, the mixture was partitioned between water (10 mL) and EtOAc (10 mL). The aqueous layer was further extracted with EtOAc (2×10 mL) and the combined organic layers were washed with brine and dried over Na$_2$SO$_4$. After the removal of organic solvent, the crude product was purified by column chromatography (EtOAc/Hexane: 1/2) to give 100 (25 mg, 41%) as a white solid. $^1$H NMR (400 MHz, CDCl$_3$) δ 8.07 (d, 1H, J=1.6 Hz), 7.54 (d, 1H, J=5.2 Hz), 7.44 (td, 1H, J=8.4, 1.6 Hz), 7.33-7.23 (m, 1H), 7.16-7.06 (m, 2H), 7.04 (d, 1H, J=5.2 Hz), 5.28 (s, 2H), 4.23 (s, 3H); LC/MS: Method 1, retention time: 5.429 min; Method 2, retention time: 3.819 min; HRMS: m/z (M+H$^+$)=314.0761 (Calculated for C$_{16}$H$_{13}$FN$_3$OS=314.0763).

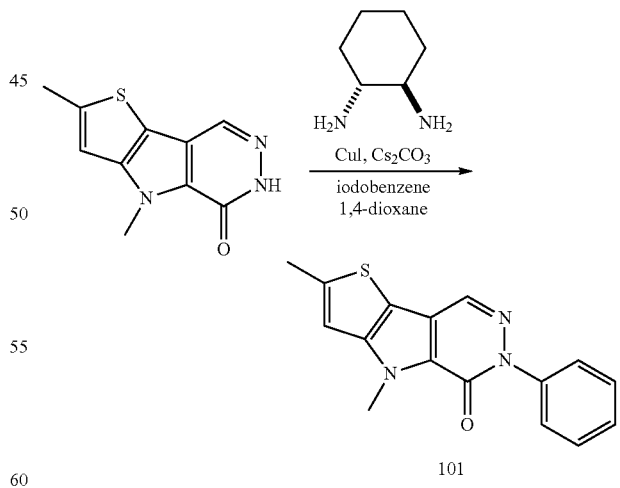

2,4-Methyl-6-[(2-fluorophenyl)methyl]-4H-thieno[3,2-b]pyrrole[3,2-d]pyridazinone (101)

Analogue 101 was prepared in a similar procedure as analogue 81. Under N$_2$ atmosphere, to a sealed tube was added unsubstituted pyridazinone (50 mg, 0.23 mmol), CuI (4.3 mg, 0.023 mmol), trans-cyclohexane-1,2-diamine (17.2 mg, 0.15 mmol), cesium carbonate (156 mg, 0.48 mmol), iodobenzene (51 μl, 0.46 mmol) and 1,4-dioxane. The tube was sealed and the mixture was refluxed overnight. After cooling to room temperature, the mixture was partitioned between water (5 mL) and DCM (5 mL). The aqueous layer was separated and further extracted with DCM (2×5 mL) and the combined organic layers were washed with brine and dried over $Na_2SO_4$. After the removal of organic solvent, the residue was directly purified by preparative HPLC to give desired coupling product 101 (17 mg, 25%) as a white solid. $^1$H NMR (400 MHz, $CDCl_3$) δ 8.30 (s, 1H), 7.64-7.59 (m, 2H), 7.52-7.46 (m, 2H), 7.41-7.36 (m, 1H), 6.83 (q, 1H, J=1.2 Hz), 4.29 (s, 3H), 2.66 (d, 3H, J=1.2 Hz); LC/MS: Method 1, retention time: 5.951 min; Method 2, retention time: 3.915 min; HRMS: m/z (M+H$^+$)=296.0860 (Calculated for $C_{16}H_{14}N_3OS$=296.0858).

2,4-Methyl-6-pentyl-4H-thieno[3,2-b]pyrrole[3,2-d]pyridazinone (102)

$^1$H NMR (400 MHz, $CDCl_3$) δ 8.23 (s, 1H), 6.81 (q, 1H, J=1.0 Hz), 5.30 (s, 2H), 4.28 (t, 2H, J=5.6 Hz), 4.27 (s, 3H), 2.64 (d, 3H, J=1.0 Hz), 1.90-1.80 (m, 2H), 1.42-1.35 (m, 4H), 0.90 (t, 3H, J=5.6 Hz); LC/MS: Method 1, retention time: 6.704; Method 2, retention time: 4.060 min; HRMS: m/z (MAI)=290.1326 (Calculated for $C_{15}H_{20}N_3OS$=290.1327).

2,4-Methyl-6-phenylmethyl-4H-thieno[3,2-b]pyrrole[3,2-d]pyridazinone (103)

$^1$H NMR (400 MHz, $CDCl_3$) δ 8.20 (s, 1H), 7.44-7.40 (m, 2H), 7.34-7.29 (m, 2H), 7.27-7.20 (m, 1H), 6.78 (q, 1H, J=1.0 Hz), 5.45 (s, 2H), 4.26 (s, 3H), 2.63 (d, 3H, J=1.0 Hz); LC/MS: Method 1, retention time: 6.254 min; Method 2, retention time: 3.992 min; HRMS: m/z (M+H$^+$)=310.1011 (Calculated for $C_{17}H_{16}N_3OS$=310.1014).

2,4-Methyl-6-[(3-fluorophenyl)methyl]-4H-thieno[3,2-b]pyrrole[3,2-d]pyridazinone (104)

$^1$H NMR (400 MHz, $CDCl_3$) δ 8.20 (s, 1H), 7.31-7.24 (m, 1H), 7.21-7.17 (m, 1H), 7.10 (dt, 1H, J=10.0, 2.0 Hz), 6.94 (tdd, 1H, J=8.4, 2.8, 0.8 Hz), 6.79 (q, 1H, J=1.2 Hz), 5.43 (s, 2H), 4.27 (s, 3H), 2.64 (d, 3H, J=1.2 Hz); LC/MS: Method 1, retention time: 6.369 min; Method 2, retention time: 4.007 min; HRMS: m/z (M+H$^+$)=328.0918 (Calculated for $C_{17}H_{15}FN_3OS$=328.0920).

2,4-Methyl-6-[(4-fluorophenyl)methyl]-4H-thieno[3,2-b]pyrrole[3,2-d]pyridazinone (105)

$^1$H NMR (400 MHz, $CDCl_3$) δ 8.23 (s, 1H), 7.45-7.39 (m, 2H), 7.02-6.97 (m, 2H), 6.80 (q, 1H, J=1.2 Hz), 5.42 (s, 2H), 4.26 (s, 3H), 2.64 (d, 3H, J=1.2 Hz); LC/MS: Method 1, retention time: 6.346 min; Method 2, retention time: 4.000 min; HRMS: m/z (M+H$^+$)=328.0919 (Calculated for $C_{17}H_{15}FN_3OS$=328.0920).

2,4-Methyl-6-[(2-chlorophenyl)methyl]-4H-thieno[3,2-b]pyrrole[3,2-d]pyridazinone (106)

$^1$H NMR (400 MHz, $CDCl_3$) δ 8.23 (s, 1H), 7.39 (dd, 1H, J=7.2, 1.6 Hz), 7.20-7.12 (m, 2H), 6.97 (ddd, 1H, J=6.8, 1.6, 0.8 Hz), 6.82 (q, 1H, J=1.2 Hz), 5.59 (s, 2H), 4.28 (s, 3H), 2.65 (d, 3H, J=1.2 Hz); LC/MS: Method 1, retention time: 6.646 min; Method 2, retention time: 4.064 min; HRMS: m/z (M+H$^+$)=344.0624 (Calculated for $C_{17}H_{15}ClN_3OS$=344.0624).

2,4-Methyl-6-[(3-chlorophenyl)methyl]-4H-thieno[3,2-b]pyrrole[3,2-d]pyridazinone (107)

$^1$H NMR (400 MHz, $CDCl_3$) δ 8.23 (s, 1H), 7.40-7.37 (m, 1H), 7.31-7.27 (m, 1H), 7.27-7.22 (m, 2H), 6.80 (q, 1H, J=1.2 Hz), 5.42 (s, 2H), 4.27 (s, 3H), 2.65 (d, 3H, J=1.2 Hz); LC/MS: Method 1, retention time: 6.704 min; Method 2, retention time: 4.081 min; HRMS: m/z (M+H$^+$)=344.0623 (Calculated for $C_{17}H_{15}ClN_3OS$=344.0624).

2,4-Methyl-6-[(4-chlorophenyl)methyl]-4H-thieno[3,2-b]pyrrole[3,2-d]pyridazinone (108)

$^1$H NMR (400 MHz, $CDCl_3$) δ 8.18 (s, 1H), 7.37 (d, 2H, J=8.4 Hz), 7.27 (d, 2H, J=8.4 Hz), 6.79 (q, 1H, J=1.2 Hz), 5.39 (s, 2H), 4.26 (s, 3H), 2.63 (d, 3H, J=1.2 Hz); LC/MS: Method 1, retention time: 6.697 min; Method 2, retention time: 4.079 min; HRMS: m/z (M+H$^+$)=344.0621 (Calculated for $C_{17}H_{15}ClN_3OS$=344.0624).

2,4-Methyl-6-[(4-methylphenyl)methyl]-4H-thieno[3,2-b]pyrrole[3,2-d]pyridazinone (109)

$^1$H NMR (400 MHz, $CDCl_3$) δ 8.17 (s, 1H), 7.33 (d, 2H, J=8.0 Hz), 7.12 (d, 2H, J=8.0 Hz), 6.78 (q, 1H, J=1.2 Hz), 5.40 (s, 2H), 4.26 (s, 3H), 2.63 (d, 3H, J=1.2 Hz), 2.30 (s, 3H); LC/MS: Method 1, retention time: 6.563 min; Method 2, retention time: 4.044 min; HRMS: m/z (M+H$^+$)=324.1170 (Calculated for $C_{18}H_{18}N_3OS$=324.1171).

2,4-Methyl-6-[(4-trifluoromethylphenyl)methyl]-4H-thieno[3,2-b]pyrrole[3,2-d]pyridazinone (110)

$^1$H NMR (400 MHz, $CDCl_3$) δ 8.20 (s, 1H), 7.58 (d, 2H, J=8.4 Hz), 7.51 (d, 2H, J=8.4 Hz), 6.79 (q, 1H, J=1.0 Hz), 5.48 (s, 2H), 4.26 (s, 3H), 2.64 (d, 3H, J=1.0 Hz); LC/MS: Method 1, retention time: 6.819 min; Method 2, retention time: 4.082 min; HRMS: m/z (M+H$^+$)=378.0886 (Calculated for $C_{18}H_{15}F_3N_3OS$=378.0888).

2,4-Methyl-6-[(4-methoxyphenyl)methyl]-4H-thieno[3,2-b]pyrrole[3,2-d]pyridazinone (111)

$^1$H NMR (400 MHz, $CDCl_3$) δ 8.19 (s, 1H), 7.39 (d, 2H, J=8.8 Hz), 6.84 (d, 2H, J=8.8 Hz), 6.78 (q, 1H, J=1.0 Hz), 5.38 (s, 2H), 4.26 (s, 3H), 3.77 (s, 3H), 2.63 (d, 3H, J=1.0 Hz); LC/MS: Method 1, retention time: 6.193 min; Method 2, retention time: 3.974 min; HRMS: m/z (M+H$^+$)=340.1114 (Calculated for $C_{18}H_{18}N_3O_2S$=340.1120).

2,4-Methyl-6-[(2,4-difluorophenyl)methyl]-4H-thieno[3,2-b]pyrrole[3,2-d]pyridazinone (112)

$^1$H NMR (400 MHz, $CDCl_3$) δ 8.19 (s, 1H), 7.32-7.24 (m, 1H), 6.85-6.76 (m, 3H), 5.47 (s, 2H), 4.27 (s, 3H), 2.64 (d, 3H, J=1.2 Hz); LC/MS: Method 1, retention time: 6.445 min; Method 2, retention time: 4.012 min; HRMS: m/z (M+H$^+$)=346.0825 (Calculated for $C_{17}H_{14}F_2N_3OS$=346.0826).

2,4-Methyl-6-[(2,6-difluorophenyl)methyl]-4H-thieno[3,2-b]pyrrole[3,2-d]pyridazinone (113)

$^1$H NMR (400 MHz, $CDCl_3$) δ 8.13 (s, 1H), 7.28-7.20 (m, 1H), 6.94-6.87 (m, 2H), 6.79 (q, 1H, J=1.2 Hz), 5.55 (s, 2H), 4.28 (s, 3H), 2.63 (d, 3H, J=1.2 Hz); LC/MS: Method 1, retention time: 6.244 min; Method 2, retention time: 3.974 min; HRMS: m/z (M+H$^+$)=346.0825 (Calculated for C$_{17}$H$_{14}$F$_2$N$_3$OS=346.0826).

2,4-Methyl-6-[(2,3-difluorophenyl)methyl]-4H-thieno[3,2-b]pyrrole[3,2-d]pyridazinone (114)

$^1$H NMR (CDCl$_3$, 400 MHz) δ 8.20 (s, 1H), 7.10-7.00 (m, 1H), 7.01-6.97 (m, 2H), 6.80 (q, 1H, J=1.2 Hz), 5.54 (d, 2H, J=0.8 Hz), 4.28 (s, 3H), 2.65 (d, 3H, J=1.2 Hz); LC/MS: Method 1, retention time: 6.443 min; Method 2, retention time: 4.009 min; HRMS: m/z (M+H$^+$)=346.0822 (Calculated for C$_{17}$H$_{14}$F$_2$N$_3$OS=346.0826).

2,4-Methyl-6-[(2-chloro-6-fluorophenyl)methyl]-4H-thieno[3,2-b]pyrrole[3,2-d]pyridazinone (115)

$^1$H NMR (CDCl$_3$, 400 MHz) δ 8.10 (s, 1H), 7.27-7.19 (m, 2H), 7.04-6.99 (m, 1H), 6.80 (m, 1H), 5.62 (d, 2H, J=1.2 Hz), 4.29 (d, 3H, J=0.8 Hz), 2.63 (d, 3H, J=1.2 Hz); LC/MS: Method 1, retention time: 6.504 min; Method 2, retention time: 4.040 min; HRMS: m/z (M+H$^+$)=362.0528 (calculated for C$_{17}$H$_{14}$ClFN$_3$OS=362.0530).

2,4-Methyl-6-[(2,3,4-trifluorophenyl)methyl]-4H-thieno[3,2-b]pyrrole[3,2-d]pyridazinone (116)

$^1$H NMR (400 MHz, CDCl$_3$) δ 8.20 (s, 1H), 7.06-6.99 (m, 1H), 6.92-6.84 (m, 1H), 6.80 (q, 1H, J=1.2 Hz), 5.48 (s, 2H), 4.27 (s, 3H), 2.65 (d, 3H, J=1.2 Hz); LC/MS: Method 1, retention time: 6.617 min; Method 2, retention time: 4.044 min; HRMS: m/z (M+H$^+$)=364.0727 (Calculated for C$_{17}$H$_{13}$F$_3$N$_3$OS=364.0731).

2,4-Methyl-6-[(2,3,5,6-tetrafluorophenyl)methyl]-4H-thieno[3,2-b]pyrrole[3,2-d]pyridazinone (117)

$^1$H NMR (400 MHz, CDCl$_3$) δ 8.14 (s, 1H), 7.07-6.88 (m, 1H), 6.80 (q, 1H, J=1.2 Hz), 5.58 (t, 2H, J=1.2 Hz), 4.27 (s, 3H), 2.65 (d, 3H, J=1.2 Hz); LC/MS: Method 1, retention time: 6.557 min; Method 2, retention time: 4.034 min; HRMS: m/z (M+H$^+$)=382.0637 (Calculated for C$_{17}$H$_{12}$F$_4$N$_3$OS=382.0637).

2,4-Methyl-6-[(3-methyl-2-fluorophenyl)methyl]-4H-thieno[3,2-b]pyrrole[3,2-d]pyridazinone (118)

$^1$H NMR (400 MHz, CDCl$_3$) δ 8.20 (s, 1H), 7.11-7.02 (m, 2H), 6.96-6.92 (m, 1H), 6.80 (q, 1H, J=1.0 Hz), 5.52 (s, 2H), 4.28 (s, 3H), 2.64 (d, 3H, J=1.0 Hz), 2.28 (s, 3H); LC/MS: Method 1, retention time: 6.641 min; Method 2, retention time: 4.055 min; HRMS: m/z (M+H$^+$)=342.1076 (Calculated for C$_{18}$H$_{17}$FN$_3$OS=342.1076).

2,4-Methyl-6-[(4-methyl-2,3-fluorophenyl)methyl]-4H-thieno[3,2-b]pyrrole[3,2-d]pyridazinone (119)

$^1$H NMR (400 MHz, CDCl$_3$) δ 8.19 (s, 1H), 6.92-6.80 (m, 2H), 6.80 (q, 1H, J=1.2 Hz), 5.49 (s, 2H), 4.27 (s, 3H), 2.64 (d, 3H, J=1.2 Hz), 2.56 (d, 3H, J=2.0 Hz); LC/MS: Method 1, retention time: 6.753 min; Method 2, retention time: 4.077 min; HRMS: m/z (M+H$^+$)=360.0983 (Calculated for C$_{18}$H$_{16}$F$_2$N$_3$OS=360.0982).

2,4-Methyl-6-[(2-fluoro-4-trifluoromethylphenyl)methyl]-4H-thieno[3,2-b]pyrrole[3,2-d]pyridazinone (120)

$^1$H NMR (400 MHz, CDCl$_3$) δ 8.21 (s, 1H), 7.36-7.32 (m, 3H), 6.81 (q, 1H, J=1.2 Hz), 5.56 (s, 2H), 4.27 (s, 3H), 2.65 (d, 3H, J=1.2 Hz); LC/MS: Method 1, retention time: 6.920 min; Method 2, retention time: 4.095 min; (TOFMS) m/z (M+H$^+$)=396.0797 (Calculated for C$_{18}$H$_{14}$F$_4$N$_3$OS=396.0794).

2,4-Methyl-6-[(3-fluoro-4-methoxyphenyl)methyl]-4H-thieno[3,2-b]pyrrole[3,2-d]pyridazinone (121)

$^1$H NMR (400 MHz, CDCl$_3$) δ 8.19 (s, 1H), 7.21-7.16 (m, 1H), 7.12-7.02 (m, 1H), 6.87-6.96 (m, 1H), 6.79 (q, 1H, J=1.2 Hz), 5.35 (s, 2H), 4.26 (s, 3H), 3.85 (s, 3H), 2.65 (d, 3H, J=1.2 Hz); LC/MS: Method 1, retention time: 6.620 min; Method 2, retention time: 3.982 min; HRMS: m/z (M+H$^+$)=358.1023 (Calculated for C$_{18}$H$_{17}$FN$_3$O$_2$S=358.1026).

Example 2

This example illustrates additional embodiments of the compounds of Formula Ia:

Compound 122: $^1$H NMR (400 MHz, DMSO-d$_6$) 8 ppm 10.35 (s, 1H), 7.76 (d, J=8.80 Hz, 3H), 7.60 (d, J=8.80 Hz, 2H), 7.18-7.30 (m, 2H), 3.14-3.20 (m, 4H), 2.91-3.01 (m, 4H), 2.08 (s, 3H).

Compound 123: $^1$H NMR (400 MHz, DMSO-d$_6$) 8 ppm 7.75 (s, 1H), 7.19-7.37 (m, 4H), 6.60 (d, J=8.80 Hz, 2H), 3.16 (d, J=4.50 Hz, 4H), 2.79-2.95 (m, 4H); LC/MS: Method 1, retention time, 5.128 min; Method 2, retention time 3.748 min; HRMS: m/z (M+H$^+$)=417.0634 (Calculated for C$_{16}$H$_{17}$N$_3$O$_4$S$_2$=417.0629).

Compound 124: $^1$H NMR (400 MHz, DMSO-d$_6$) 8 ppm 7.18 (m, 3H), 6.98-7.09 (m, 2H), 6.81-6.97 (m, 2H), 4.18-4.36 (m, 4H), 3.08-3.21 (m, 8H), 1.66-1.83 (m, 2H); LC/MS: Method 1, retention time, 5.017 min; Method 2, retention time 3.704 min; HRMS: m/z (M+H$^+$)=453.1035 (Calculated for C$_{19}$H$_{23}$N$_3$O$_6$S$_2$=453.1028).

Compound 125: $^1$H NMR (400 MHz, DMSO-d$_6$) 8 ppm 7.30-7.40 (m, 2H), 7.13-7.23 (m, 2H), 6.95-7.09 (m, 1H), 6.52-6.65 (m, 2H), 4.19-4.36 (m, 4H), 3.20-3.28 (m, 2H), 3.15 (m, 4H), 3.02-3.12 (m, 2H), 1.62-1.79 (m, 2H). Method 1, retention time, 5.100 min; Method 2, retention time 3.741 min; HRMS: m/z (M+H$^+$)=453.1036 (Calculated for C$_{17}$H$_{15}$FN$_3$OS=453.1028).

Compound 126: $^1$H NMR (400 MHz, DMSO-d$_6$) δ ppm 10.16-10.29 (m, 1H), 7.99-8.15 (m, 1H), 7.76 (dd, J=8.12, 0.88 Hz, 1H), 7.50 (t, J=8.02 Hz, 1H), 7.39 (d, J=8.02 Hz, 1H), 6.81-6.99 (m, 2H), 3.75 (s, 3H), 3.35-3.44 (m, 2H), 3.30 (m, 4H), 3.23 (t, J=5.77 Hz, 2H), 2.04 (s, 3H), 1.69-1.89 (m, 2H); LC/MS: Method 1, retention time, 5.349 min; Method 2, retention time 3.907 min; HRMS: m/z (M+H$^+$)=503.1004 (Calculated for C$_{20}$H$_{23}$N$_3$O$_6$S$_2$=503.0996).

Compound 127: $^1$H NMR (400 MHz, DMSO-d$_6$) δ ppm 10.31 (s, 1H), 7.71 (m, 4H), 6.76-7.00 (m, 2H), 3.82 (s, 3H), 3.16-3.32 (m, 8H), 2.05 (s, 3H), 1.78 (m, 2H).

Compound 128: $^1$H NMR (400 MHz, DMSO-d$_6$) 5 ppm 7.16-7.30 (m, 2H), 6.99-7.10 (m, 1H), 6.85-6.96 (m, 2H), 4.29 (q, J=5.09 Hz, 4H), 3.82 (s, 3H), 3.30-3.49 (m, 4H), 3.14-3.25 (m, 4H), 1.75 (m, 2H). LC/MS: Method 1, retention time, 5.897 min; Method 2, retention time 3.782 min; HRMS: m/z (M+H$^+$)=504.0851 (Calculated for C$_{20}$H$_{22}$N$_2$O$_7$F$_2$S$_2$=504.0836).

Compound 129: $^1$H NMR (400 MHz, DMSO-d$_6$) δ ppm 10.17-10.35 (s, 1H), 7.92-8.09 (m, 1H), 7.71-7.85 (m, 1H), 7.44-7.57 (m, 1H), 7.24-7.39 (m, 1H), 6.95-7.17 (m, 3H), 4.15-4.41 (m, 4H), 2.82-3.03 (m, 8H), 2.04 (s, 3H).

Compound 130: $^1$H NMR (400 MHz, DMSO-d$_6$) δ ppm 10.35 (s, 1H), 7.76 (d, J=8.80 Hz, 2H), 7.58 (d, J=8.80 Hz, 2H), 7.08 (dd, J=4.30, 2.35 Hz, 2H), 6.98 (d, J=9.00 Hz, 1H), 4.29 (d, J=3.72 Hz, 4H), 2.91 (m, 8H), 2.07 (s, 3H).

Compound 131: $^1$H NMR (400 MHz, DMSO-d$_6$) 5 ppm 10.24 (s, 1H), 7.98-8.13 (m, 1H), 7.72-7.79 (m, 1H), 7.49 (s, 1H), 7.34-7.40 (m, 1H), 7.18 (m, 2H), 6.96-7.03 (m, 1H), 4.20-4.35 (m, 4H), 3.37-3.45 (m, 4H), 3.09-3.22 (m, 4H), 2.04 (s, 3H), 1.70-1.82 (m, 2H); LC/MS: Method 1, retention time, 5.131 min; Method 2, retention time 3.744 min; HRMS: m/z (M+H$^+$)=495.1133 (Calculated for C$_{21}$H$_{25}$N$_3$O$_7$S$_2$=495.1134).

Compound 132: $^1$H NMR (400 MHz, DMSO-d$_6$) δ ppm 10.25-10.36 (m, 1H), 7.73 (m, 2H), 7.67 (m, 2H), 7.17 (m, 2H), 7.01 (m, 1H), 4.28 (d, J=4.11 Hz, 4H), 3.16 (m, 8H), 2.05 (s, 3H), 1.74 (m, 2H).

Compound 133: $^1$H NMR (400 MHz, DMSO-d$_6$) δ ppm 10.27 (s, 1H), 7.94-8.08 (m, 1H), 7.73-7.88 (m, 1H), 7.51 (t, J=8.02 Hz, 1H), 7.32 (d, J=8.02 Hz, 1H), 6.89 (d, J=11.54 Hz, 2H), 3.84 (s, 3H), 2.88-3.21 (m, 8H), 2.04 (s, 3H); LC/MS: Method 1, retention time, 5.296 min; Method 2, retention time 3.773 min; HRMS: m/z (M+H$^+$)=489.0845 (Calculated for C$_{19}$H$_{21}$N$_3$O$_6$F$_2$S$_2$=489.0840).

122
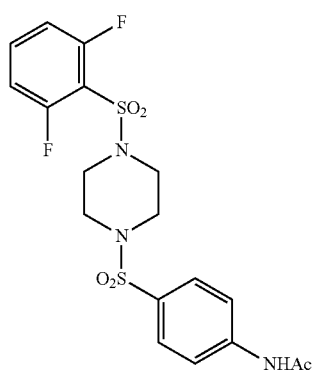

123
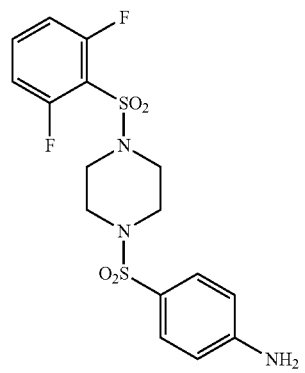

124
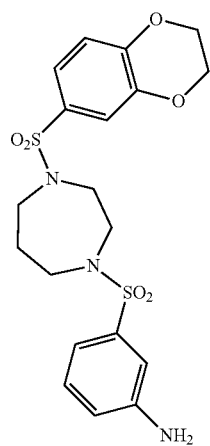

-continued

125
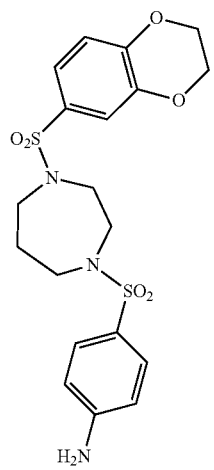

126
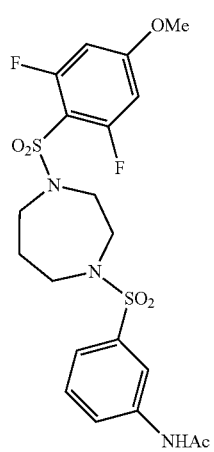

127
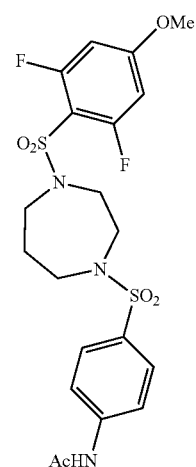

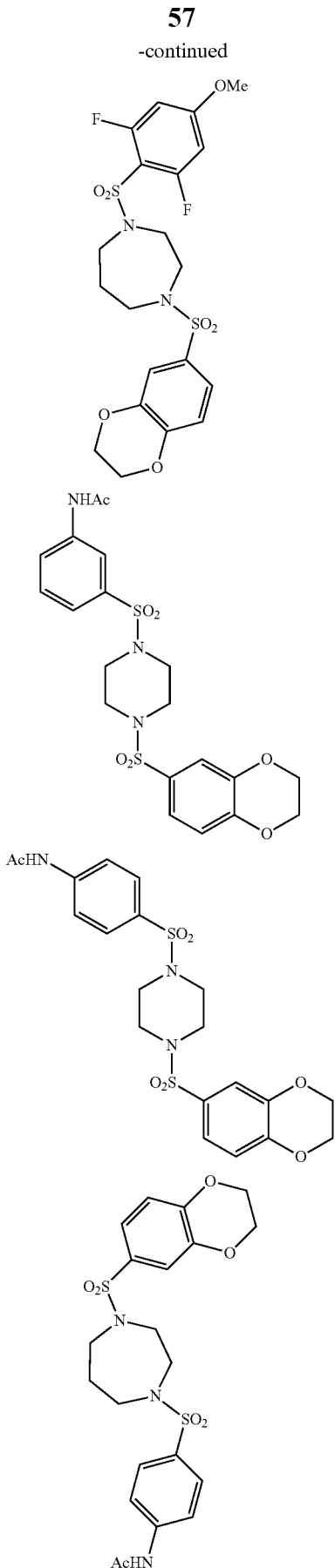

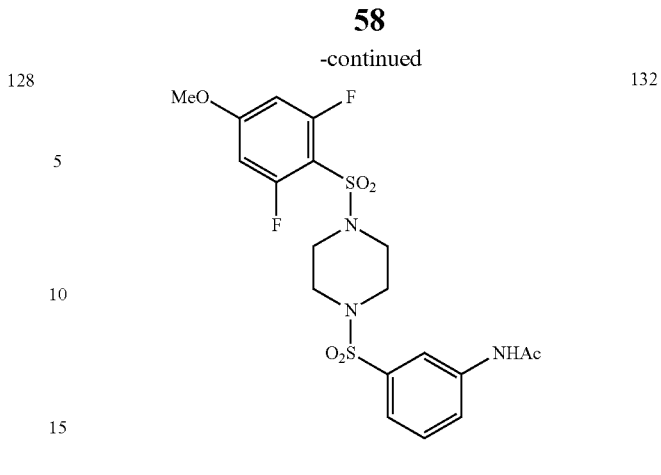

Example 3

This example illustrates some of the properties of the compounds of the invention.

Reagents:

Kinase-Glo was obtained from Promega (Madison, Wis.). ATP, PEP, LDH and NADH were from Sigma. Reagents and solvents were purchased from Sigma, Alfa Aesar, Acros, Enamine, Oakwood Products, Matrix Scientific or Chem-Impex International.

Luminescent Pyruvate Kinase-Luciferase Coupled Assay.

Production of a luminescent signal based on the generation of ATP by pyruvate kinase was determined by using the ATP-dependent enzyme firefly luciferase. Three μL of substrate mix (at r.t.) in assay buffer (50 mM imidazole pH 7.2, 50 mM KCl, 7 mM $MgCl_2$, 0.01% tween 20, 0.05% BSA) was dispensed into Kalypsys white solid bottom 1,536 well microtiter plates using a bottle-valve solenoid-based dispenser (Kalypsys). The final concentrations of substrates in the assay were 0.1 mM ADP and 0.5 mM PEP. Twenty-three nL of compound were delivered with a 1,536-pin array tool and 1 μl of enzyme mix in assay buffer (final concentration, 0.1 nM pyruvate kinase, 50 mM imidazole pH 7.2, 0.05% BSA, 4° C.) was added. Microtiter plates were incubated at r.t. for 1 hour and 2 uL of luciferase detection mix (Kinase-Glo, Promega at 4° C. protected from light) was added and luminescence was read with a ViewLux (Perkin Elmer) using a 5 second exposure/plate. Data was normalized for AC50 values to control columns containing uninhibited enzyme (n), and $AC_{100}$ inhibition (i) according the following equation: Activation (%)=[(c−n)/(n−i)]*100 where c=compound, n=DMSO neutral, i=no enzyme control. A % activity of 100% is approximately a 2-fold increase over basel assay signal (% Activation by FBP was variable but averaged 100%). Monitoring of activation was accomplished using enzyme at 3× the final concentration. The primary qHTS data and confirmatory data are available in PubChem (AIDS: 1631, 1634, and 1751). Follow-up of synthesized analogs was determined using the same protocol with the exception that the enzyme concentrations for isoforms PKM1, L and R were 1 nM, 0.1 nM, and 0.1 nM respectively (PubChem AIDs for M1, L and R bioluminescent assays are 1780, 1781, and 1782).

Fluorescent Pyruvate Kinase-Lactate Dehydrogenase Coupled Secondary Assay.

All compounds were also tested in a kinetic mode by coupling the generation of pyruvate by pyruvate kinase to the depletion of NADH through lactate dehydrogenase. For PKM2, 3 μL of substrate mix (final concentration, 50 mM Tris-Cl pH 8.0, 200 mM KCl, 15 mM $MgCl_2$, 0.1 mM PEP, 4.0 mM ADP, and 0.2 mM NADH) was dispensed into Kalypsys black-solid 1,536 well plates using the Aurora Discovery BioRAPTR Flying Reagent Dispenser (FRD; Beckton-Dickenson, Franklin Lakes, N.J.) and 23 nL of compounds were delivered a Kalypsys pin tool and then 1 µL of enzyme mix (final concentrations, 10 nM hPK-M2 and 1 µM of LDH) was added. Plates were immediately placed in ViewLux (Perkin Elmer) and NADH fluorescence was determined at 30 second exposure intervals for between 3 and 6 minutes. Data were normalized to the uninhibited and $EC_{100}$ activation using known activators such as fructose-1,6-bis-phosphate. The data has been deposited in PubChem (AID: 1540). Follow-up of synthesized analogs was determined using the same protocol (PubChem AIDs for L, M1 and R bioluminescent assays are 1541, 1542, and 1543). This assay was also used to determine the $K_M$'s for PEP and ADP in the presence and absence of activator. Conversion of fluorescent units to pmols of NADH was performed using a standard curve of known NADH concentrations. Data was collected on the Perkin Elmer Viewlux.

Mode of Action.

Figure 1B:
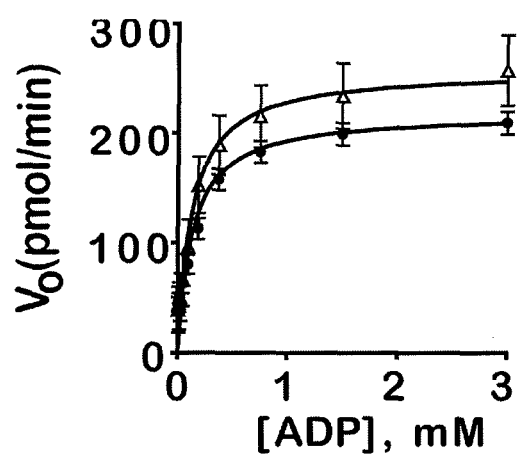
FIG. 1B illustrates the reduced effect of compound 1 on ADP kinetics.

The mode of action was examined for each of these lead chemotypes through analysis of the activators on the kinetics of PEP and ADP utilization by the enzyme. As discussed, FBP is known to allosterically activate PKM2 through induction of an enzyme state with a high affinity for PEP. In the absence of activator, hPK shows low affinity for PEP ($K_M$ ~1.5 mM). In the presence of 1 or FBP the $K_M$ for PEP decreased to 0.26±0.08 mM or 0.1±0.02 mM, respectively. Comparison of the ADP titration in the presence and absence of activators shows that these kinetics are not significantly affected ($K_M$ for ADP ~0.1 mM in either condition; $V_{max}$ values within 20% of each other). Thus, the primary lead NCGC00030335 (the substituted N,N'-diarylsulfonamide 1) increased the affinity of PKM2 for PEP (FIG. 1A) while having less affect on ADP kinetics (FIG. 1B).

Identification of NCGC00030355 (1):

Following the qHTS the CRC data was subjected to a classification scheme to rank the quality of the CRCs as described by Inglese and co-workers (*Proc. Natl. Acad. Sci. USA* 2006, 103, 11473-11478) (see FIG. 3). Agents, including NCGC00030335 (1), were chosen for follow-up based upon their curve class ranking. Briefly, CRCs are placed into four classes. Class 1 contains complete CRCs showing both upper and lower asymptotes and $r^2$ values >0.9. Class 2 contains incomplete CRCs lacking the lower asymptote and shows $r^2$ values greater than 0.9. Class 3 curves are of the lowest confidence because they are defined by a single concentration point where the minimal acceptable activity is set at 3 SD of the mean activity calculated from the lowest tested concentration. Finally, class 4 contains compounds that do not show any CRCs and are therefore classified as inactive.

Figure 3:
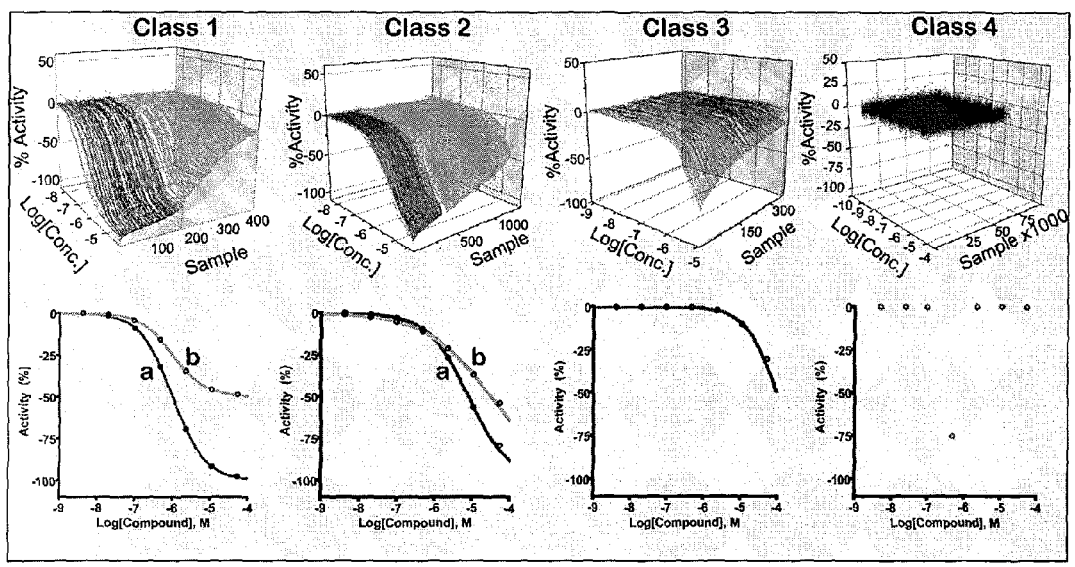
FIG. 3 illustrates qHTS data and its classification scheme ranking criteria followed in this application.

FIG. 3 shows an example qHTS data and classification scheme for assignment of resulting curve-fit data into classes. Top, qHTS curve-fit data from AID 361 binned into curve classifications 1-4 based classification criteria. Below, Examples of curves fitting the following classification criteria: Class 1 curves display two asymptotes, an inflection point, and r2≥0.9; subclasses 1a (blue) vs. 1b (orange) are differentiated by full (>80%) vs. partial (≤80%) response. Class 2 curves display a single left-hand asymptote and inflection point; subclasses 2a (blue) and 2b (orange) are differentiated by a max response and r2, >80% and >0.9 or <80% and <0.9, respectively. Class 3 curves have a single left-hand asymptote, no inflection point, and a response >3SD the mean activity of the sample field. Class 4 defines those samples showing no activity across the concentration range.

SAR of Substituted N,N'-diarylsulfonamides and Selected Analogues.

The lead structure 1 identified from the primary screen was found to possess $AC_{50}$ values versus PKM2 of 0.063±0.02 µM and 0.111±0.03 µM and maximum responses versus PKM2 (relative to activation by FBP) of 122.1% and 92.2%, respectively (Table 1). In the LDH assay, that used high saturating ADP levels and low (0.1 mM) levels of PEP, average greater efficacy but lower potency was found for compound 1 showing $AC_{50}$ value of 0.3±0.1 µM but with maximum response of 224%. The initial focus involved symmetric versions of the N,N'-diarylsulfonamides. As such, symmetry was examined utilizing the 6-(2,3-dihydrobenzo[b][1,4]dioxine) heterocycle (analogue 2) and the 4-methoxybenzene ring (analogue 3). Each analogue had slightly diminished $AC_{50}$ values (270 nM and 171 nM, respectively). From here, one aryl sulfonamide unit was held constant while exploring the SAR of the other aryl sulfonamide. Compounds 6-18 are representative examples from this strategy whereby the 6-(2,3-dihydrobenzo[b][1,4]dioxine) heterocycle remained constant and the 4-methoxybenzene ring was changed utilizing standard phenyl ring analogues. While there were selective tendencies associated with electron withdrawing and electron donating substituents, as a whole there was no discernable trend associated with either strategy. Substitutions of small and modest size were accepted at the ortho, meta and para positions. Moderate to large substitutions, however, were not tolerated at the para position. This is demonstrated by comparison of analogues 11 and 12 in which replacing the para-methoxy substituent in 11 with the para-n-propyl group in 12 shows diminished activity (this general trend was seen with numerous analogues; data not shown). The most effective substitutions involved electron withdrawing groups in the 2- and 6-positions of the phenyl ring [for instance 2,6-difluorobenzene (analogue 9, $AC_{50}$=65±25 nM, maximum response=94.4%), 2,6-difluoro-4-methoxybenzene (analogue 11, $AC_{50}$=28±9 nM, maximum response=91.8%) and 2,6-difluoro-3-phenol (analogue 13, $AC_{50}$=52±14 nM, maximum response=95.3%)]. In an attempt to place additional electron density in the ortho-position of this phenyl ring a pyridine analogue was synthesized placing the nitrogen at the 2-position of the aromatic ring (analogue 18) and additionally oxidized to the N-oxide 19. This design was not successful as 19 displayed both reduced potency and maximum response ($AC_{50}$>10 µM in both assays). Given the established advantage of the di-fluoro analogues, we next chose to hold the 2,6-difluorobenzene ring constant and vary the opposite side with both substituted phenyl rings and various heterocycles. Numerous analogues of this class were synthesized and tested and compounds 21-29 are good representations of these analogues' SAR. The various substituted phenyl rings generally resulted in active compounds as represented by 21 ($AC_{50}$=90±16 nM, maximum response=102.0%) and 22 ($AC_{50}$=66±nM, maximum response=74.3%). Both compound 21 and 22 showed comparable activity in the LDH coupled assay with $AC_{50}$'s=211±50 nM (maximum response=124±30) and 172±29 nM (maximum response=85±8%), respectively. However, none provided significant improvements in potency or maximum response. Altering the heterocycle from the 6-(2,3-dihydrobenzo[b][1,4]dioxine) moiety had varying consequences. Several heterocycles were tolerated including the 7-(3,4-dihydro-2H-benzo[b][1,4]dioxepine) moiety (analogue 23, $AC_{50}$=103±30 nM, maximum response=100.4%) and the 6-(2-methylbenzo[d]thiazole) moiety (analogue 29, $AC_{50}$=86±6 nM, maximum response=103.6%). As well, in the LDH assay 23 and 29 showed potencies of ~0.5 μM with maximum responses of 109±11% and 156±11%. The 2-napthyl and 6-(2,2-dimethylchroman) derivatives provided significant enhancement in terms of maximum response (analogues 26 and 27, $AC_{50}$=66±4 nM and 93±12 nM, maximum response=138.0% and 119.3%, respectively). Compound 26 also showed good response in the LDH assay with an $AC_{50}$=220±53 nM and a maximum response of 161±29%. The sulfone derivatives that were explored showed loss of potency. Interestingly, this loss was more severe when the sulfone moiety bridged the piperidine ring system to the 6-(2,3-dihydrobenzo[b][1,4]dioxine) system relative to substituted phenyl rings (i.e. 2,6-difluorophenyl) as illustrated by analogues 19 and 30 ($AC_{50}$=254±47 nM and 863±56 nM, maximum response=104.3% and 110.0%, respectively, similar values were also observed in the LDH assay).

TABLE 1

(Ia)

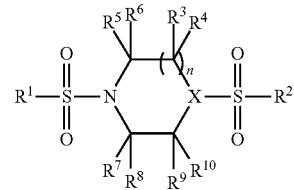

where n = 1 for compounds 1-30; n = 2 for compound 31;
$R^3$-$R^{10}$ = H for compounds 1-31.

| Compound No. | X | $R^1$ | $R^2$ | hPK, M2 $AC_{50}(\mu M)^a$ | hPK, M2 Max. Res.[b] |
|---|---|---|---|---|---|
| 1 | N | 4-methoxyphenyl | 6-(2,3-dihydro-benzo[b][1,4]dioxinyl) | 0.111 ± 0.03 | 92.2 ± 12.0 |
| 2 | N | 6-(2,3-dihydro-benzo[b][1,4]dioxinyl) | 6-(2,3-dihydro-benzo[b][1,4]dioxinyl) | 0.270 ± 0.08 | 89.7 ± 2.2 |
| 3 | N | 4-methoxyphenyl | 4-methoxyphenyl | 0.171 ± 0.01 | 87.6 ± 16.2 |
| 4 | N | 4-cyanophenyl | 6-(2,3-dihydro-benzo[b][1,4]dioxinyl) | 0.029 ± 0.02 | 44.1 ± 6.1 |
| 5 | N | 4-chlorophenyl | 6-(2,3-dihydro-benzo[b][1,4]dioxinyl) | 0.154 ± 0.08 | 99.6 ± 2.5 |
| 6 | N | 4-fluorophenyl | 6-(2,3-dihydro-benzo[b][1,4]dioxinyl) | 0.094 ± 0.03 | 99.7 ± 54.2 |
| 7 | N | 3-fluorophenyl | 6-(2,3-dihydro-benzo[b][1,4]dioxinyl) | 0.316 ± 0 | 106.7 ± 8.8 |
| 8 | N | 2-fluorophenyl | 6-(2,3-dihydro-benzo[b][1,4]dioxinyl) | 0.089 ± 0.03 | 114.4 ± 4.0 |
| 9 | N | 2,6-difluorophenyl | 6-(2,3-dihydro-benzo[b][1,4]dioxinyl) | 0.065 ± 0.03 | 94.4 ± 2.8 |
| 10 | N | 2,4,5-trifluorophenyl | 6-(2,3-dihydro-benzo[b][1,4]dioxinyl) | 0.090 ± 0.01 | 104.9 ± 7.6 |
| 11 | N | 2,6-difluoro-4-methoxyphenyl | 6-(2,3-dihydro-benzo[b][1,4]dioxinyl) | 0.028 ± 0.01 | 91.8 ± 9.6 |
| 12 | N | 2,5-difluoro-3-propylphenyl | 6-(2,3-dihydro-benzo[b][1,4]dioxinyl) | 0.757 ± 0.22 | 69.2 ± 10.4 |
| 13 | N | 2,6-difluoro-3-hydroxyphenyl | 6-(2,3-dihydro-benzo[b][1,4]dioxinyl) | 0.052 ± 0.01 | 95.3 ± 8.4 |
| 14 | N | 2,4-difluorophenyl | 6-(2,3-dihydro-benzo[b][1,4]dioxinyl) | 0.124 ± 0.03 | 112.9 ± 6.3 |
| 15 | N | phenyl | 6-(2,3-dihydro-benzo[b][1,4]dioxinyl) | 0.202 ± 0.04 | 108.2 ± 4.3 |
| 16 | N | 3-(trifluoromethyl)phenyl | 6-(2,3-dihydro-benzo[b][1,4]dioxinyl) | 0.209 ± 0.07 | 39.3 ± 6.2 |
| 17 | N | 3-methoxyphenyl | 6-(2,3-dihydro-benzo[b][1,4]dioxinyl) | 0.113 ± 0.04 | 90.0 ± 4.5 |
| 18 | N | 2-pyridyl | 6-(2,3-dihydro-benzo[b][1,4]dioxinyl) | 0.542 ± 0.04 | 103.1 ± 6.6 |
| 19 | N | 2-pyridyl-1-oxide | 6-(2,3-dihydro-benzo[b][1,4]dioxinyl) | >10 | 81.5 ± 3.2 |
| 20 | CH | 2,6-difluorophenyl | 6-(2,3-dihydro-benzo[b][1,4]dioxinyl) | 0.254 ± 0.05 | 104.3 ± 5.1 |
| 21 | N | 4-methoxyphenyl | 6-(2,3-dihydro-benzo[b][1,4]dioxinyl) | 0.090 ± 0.02 | 102.0 ± 9.2 |
| 22 | N | 2,6-difluorophenyl | 2,6-difluorophenyl | 0.066 ± 0.01 | 74.3 ± 9.8 |
| 23 | N | 2,6-difluorophenyl | 7-(3,4-dihydro-2H-benzo[b][1,4]dioxepine) | 0.103 ± 0.03 | 100.4 ± 6.6 |
| 24 | N | 2,6-difluorophenyl | 5-benzo[b][1,3]dioxinyl | 0.191 ± 0.06 | 61.0 ± 1.2 |
| 25' | N | 2,6-difluorophenyl | 7-(4-methyl-3,4-dihydro-2H-pyrido[3,2-b][1,4]oxazine) | 2.71 ± 0.18 | 93.5 ± 5.9 |
| 26 | N | 2,6-difluorophenyl | 2-naphthalenyl | 0.066 ± 0 | 138.0 ± 11.3 |
| 27 | N | 2,6-difluorophenyl | 6-(2,2-dimethylchroman)yl | 0.093 ± 0.01 | 119.3 ± 5.4 |
| 28 | N | 2,6-difluorophenyl | 5-(1-methyl-1H-indolyl) | 0.387 ± 0.07 | 91.1 ± 4.7 |
| 29 | N | 2,6-difluorophenyl | 6-(2-methylbenzo[d]thiazolyl) | 0.086 ± 0.01 | 103.6 ± 5.8 |

TABLE 1-continued

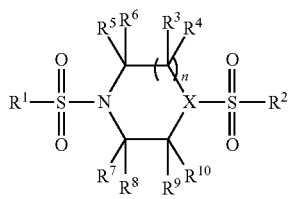

(Ia)

where n = 1 for compounds 1-30; n = 2 for compound 31;
$R^3$-$R^{10}$ = H for compounds 1-31.

| Compound No. | X | $R^1$ | $R^2$ | hPK, M2 $AC_{50}(\mu M)^a$ | hPK, M2 Max. Res.$^b$ |
|---|---|---|---|---|---|
| 30 | CH | 2,6-difluorophenyl | 6-(2,3-dihydrobenzo[b][1,4]dioxinyl) | 0.863 ± 0.12 | 110.0 ± 5.4 |
| 31 | N | 2,6-difluorophenyl | 6-(2,3-dihydrobenzo[b][1,4]dioxinyl) | 0.866 ± 0.15 | 119.9 ± 7.3 |

$^a$AC50 values were determined utilizing the luminescent pyruvate kinase-luciferase coupled assay and the data represents the results from three separate experiments.
$^b$Max. Res. (Maximum Response) is % activity that represents % activation at 57 μM of compound.

Additional compounds of Formula Ia and their properties are set forth in Table 2.

TABLE 2

| | | | | KinaseGlo | | LDH | |
|---|---|---|---|---|---|---|---|
| Compound No. | X | $R^1$ | $R^2$ | hPK, M2 $AC_{50}(\mu M)$ | hPK, M2 Max. Res.$^a$ | hPK, M2 $AC_{50}(\mu M)$ | hPK, M2 Max. Res.$^a$ |
| 122 | N | 2,6-difluorophenyl | p-acetylaminophenyl | | | | |
| 123 | N | 2,6-difluorophenyl | p-aminophenyl | 0.6506 | 82.61 | 0.4105 | 170.98 |
| *124 | N | m-aminophenyl | 6-(2,3-dihydro-benzo[b][1,4]dioxinyl) | 0.0326 | 88.94 | 0.0919 | 169.71 |
| *125 | N | p-aminophenyl | 6-(2,3-dihydro-benzo[b][1,4]dioxinyl) | 0.1031 | 86.64 | 0.1634 | 131.59 |
| *126 | N | m-acetylaminophenyl | 2,6-difluoro-4-methoxyphenyl | 2.9063 | 83.79 | 2.9063 | 114.61 |
| *127 | N | p-acetylaminophenyl | 2,6-difluoro-4-methoxyphenyl | | | | |
| *128 | N | 2,6-difluoro-4-methoxyphenyl | 6-(2,3-dihydro-benzo[b][1,4]dioxinyl) | 0.0366 | 96.67 | 0.058 | 159.85 |
| 129 | N | m-acetylaminophenyl | 6-(2,3-dihydro-benzo[b][1,4]dioxinyl) | | | | |
| 130 | N | p-acetylaminophenyl | 6-(2,3-dihydro-benzo[b][1,4]dioxinyl) | | | | |
| *131 | N | m-acetylaminophenyl | 6-(2,3-dihydro-benzo[b][1,4]dioxinyl) | 0.8191 | 91.11 | 0.8191 | 123.67 |
| *132 | N | p-acetylaminophenyl | 6-(2,3-dihydro-benzo[b][1,4]dioxinyl) | 4.1053 | 81.07 | 2.5902 | 123.97 |
| 133 | N | m-acetylaminophenyl | 2,6-difluoro-4-methoxyphenyl | 1.63 | 60.00 | 1.0312 | 94.88 |
| 134 | N | m-aminophenyl | 2,6-difluoro-4-methoxyphenyl | 0.0231 | 87.00 | 0.073 | 141.67 |
| 135 | N | m-aminophenyl | 6-(2,3-dihydro-benzo[b][1,4]dioxinyl) | 0.0411 | 82.08 | 0.1457 | 98.13 |
| 136 | N | m-(ethylamino)-phenyl | 6-(2,3-dihydro-benzo[b][1,4]dioxinyl) | 0.081 | 63.00 | nd | nd |
| 137 | N | m-aminophenyl | 2,6-difluorophenyl | 0.0919 | 81.51 | 0.2058 | 154.42 |
| 138 | N | m-(N,N-dimethylamino)-phenyl | 6-(2,3-dihydro-benzo[b][1,4]dioxinyl) | 0.092 | 54.00 | nd | nd |

TABLE 2-continued

| Compound No. | X | R[1] | R[2] | KinaseGlo hPK, M2 AC$_{50}$(μM) | KinaseGlo hPK, M2 Max. Res.[a] | LDH hPK, M2 AC$_{50}$(μM) | LDH hPK, M2 Max. Res.[a] |
|---|---|---|---|---|---|---|---|
| 139 | N | p-aminophenyl | 2,6-difluoro-4-methoxyphenyl | 0.1298 | 92.46 | 0.1834 | 166.00 |
| 140 | N | m-hydroxyphenyl | 2,6-difluorophenyl | 0.1834 | 89.61 | 0.1834 | 148.41 |
| *141 | N | m-aminophenyl | 2,6-difluoro-4-methoxyphenyl | 0.2058 | 93.20 | 0.1457 | 157.96 |
| 142 | N | m-(methylamino)-phenyl | 6-(2,3-dihydro-benzo[b][1,4]dioxinyl) | 0.29 | 67.00 | nd | nd |
| *143 | N | p-aminophenyl | 2,6-difluoro-4-methoxyphenyl | 1.2982 | 89.36 | 1.2982 | 150.25 |
| 144 | N | 2,6-difluoro-4-methoxyphenyl | 2-thiophenyl | 0.0366 | 95.08 | 0.0517 | 125.28 |
| 145 | N | 2,6-difluoro-4-methoxyphenyl | 2-furanyl | 0.1834 | 82.49 | 0.1157 | 106.13 |
| 146 | N | 2-amino-4-pyridyl | 6-(2,3-dihydro-benzo[b][1,4]dioxinyl) | 1.6 | 81.00 | nd | nd |
| 151 | N | p-aminophenyl | 6-(2,3-dihydro-benzo[b][1,4]dioxinyl) | 0.4105 | 91.84 | 0.3659 | 174.46 |

*n = 2; others n = 1; $R^3$—$R^{10}$=H.
[a]Max Res. (Maximum Response) is % activity that represents % activation at 57 μM of compound.

Several linear diamines and several alternate diamine core ring systems were examined. For these studies we retained the 2,6-difluorophenyl and 6-(2,3-dihydrobenzo[b][1,4]dioxine) heterocycle as the two aryl substituents to afford comparative uniformity. The results are shown in Table 1 and demonstrate that the piperazine and the related 1,4-diazepane (analogue 31, AC$_{50}$=866 nM, maximum response=119.9%) had clear advantages over other diamine moieties. Ligations with linear diamines ranging from 2- to 6-carbons in length (analogues 32-36) were found to have diminished potencies, as shown in Table 3. Cis and trans versions of the cyclohexane-1,4-diamine ligation conferred similar loss in activation potency. Interestingly, the trans version of this analogue performed significantly better than the cis version (analogues 37 and 38, AC$_{50}$=2.11±0.64 μM and 37.1±5 μM, maximum response of 90.8% and 60.7%, respectively; AC$_{50}$s of 7±1.5 μM and 56±11% for both compounds in the LDH assay). Numerous analogues with one secondary amine contained in 4-, 5- and 6-membered rings and one exocyclic primary amine were examined (analogues 39-44) and found to be less active than the original lead compounds in both assays. In addition to the derivatives shown in Table 3, numerous bicyclic and spirocyclic diamines were examined (for instance 2,6-diazabicyclo[3.2.2]nonane and 2,7-diazaspiro[4.4]nonane) and found to be less active that the corresponding piperazine and 1,4-diazepane analogues (data not shown).

TABLE 3

$$R^1-\underset{\underset{O}{\|}}{\overset{\overset{O}{\|}}{S}}-L-\underset{\underset{O}{\|}}{\overset{\overset{O}{\|}}{S}}-R^2$$

where $R^1$ = 2,6-difluorophenyl;
$R^2$ = 6-(2,3-dihydro-benzo[b][1,4]dioxinyl).

| Compound No. | L | hPK, M2 AC$_{50}$(μM)[a] | hPK, M2 Max. Res.[b] |
|---|---|---|---|
| 32 | N,N'-(ethane-1,2-diyl) | >15 | 60.3 ± 20.6 |
| 33 | N,N'-(propane-1,3-diyl) | 3.85 ± 0.53 | 105.7 ± 5.1 |
| 34 | N,N'-(butane-1,4-diyl) | 7.97 ± 4.05 | 113.0 ± 14.6 |
| 35 | N,N'-(pentane-1,5-diyl) | 2.33 ± 0.16 | 113.9 ± 1.4 |
| 36 | N,N'-(hexane-1,6-diyl) | 4.83 ± 0.31 | 110.4 ± 3.0 |
| 37 | N,N'-((trans)-cyclohexane-1,4-diyl) | 2.11 ± 0.48 | 90.8 ± 12.4 |
| 38 | N,N'-((cis)-cyclohexane-1,4-diyl) | >35 | 60.7 ± 5.6 |
| 39 | 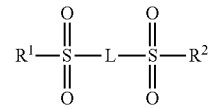 | 3.69 ± 1.26 | 100.9 ± 1.9 |
| 40 | | 9.00 ± 4.5 | 99.6 ± 3.1 |
| 41 | | >15 | 82.4 ± 18 |
| 42 | | >10 | 83.7 ± 24.2 |
| 43 | | 4.47 ± 0 | 93.3 ± 9 |

TABLE 3-continued $$R^1 - \underset{\underset{O}{\|}}{\overset{\overset{O}{\|}}{S}} - L - \underset{\underset{O}{\|}}{\overset{\overset{O}{\|}}{S}} - R^2$$

where $R^1$ = 2,6-difluorophenyl;
$R^2$ = 6-(2,3-dihydro-benzo[b][1,4]dioxinyl).

| Compound No. | L | hPK, M2 AC$_{50}$(μM)[a] | hPK, M2 Max. Res.[b] |
|---|---|---|---|
| 44 | HN–⟨azetidine⟩–N | 3.05 ± 0.2 | 108.3 ± 5.3 |

[a] AC50 values were determined utilizing the luminescent pyruvate kinase-luciferase coupled assay and the data represents the results from three separate experiments.
[b] Max Res. (Maximum Response) is % activity that represents % activation at 57 μM of compound.

Further investigations were made into substitutions directly on the piperazine ring. To this end, several piperazine rings were synthesized and evaluated with a single methyl addition proximal to either the 2,6-difluorophenyl or 6-(2,3-dihydrobenzo[b][1,4]dioxine) heterocycle. Additional consideration was given to the absolute stereochemistry of the methyl group. The results are detailed in Table 43 and show that these analogues were less potent than the unmodified ring systems. Another piperazine ring modification was the incorporation of a carbonyl moiety alpha to the ring nitrogens. Here, the amine to lactam conversion proximal to the 6-(2,3-dihydrobenzo[b][1,4]dioxine) heterocycle resulted in an active derivative (analogue 49, AC$_{50}$=114±10 nM, maximum response=105.1%; LDH assay showed AC$_{50}$=0.44±0.24 μM, maximum response=87±37%). The same amine to lactam conversion adjacent to the 2,6-difluorobenzene resulted in a loss of potency (analogue 50, AC$_{50}$=2.42±0.94 μM, maximum response=96.9%; LDH assay showed AC$_{50}$=3.16 μM, maximum response=82%). The activities of these agents again demonstrate the lack of symmetric SAR for this chemotype.

TABLE 4

| Compound No. | hPK, M2 AC$_{50}$(μM)[a] | hPK, M2 Max. Res.[b] |
|---|---|---|
| 45 | 4.34 ± 0.74 | 109.0 ± 9.4 |
| 46 | 3.10 ± 1.17 | 98.8 ± 2.6 |
| 47 | 9.18 ± 2.56 | 107.6 ± 9.9 |
| 48 | 2.96 ± 0.2 | 107.9 ± 8.4 |
| 49 | 0.114 ± 0.02 | 105.1 ± 9 |
| 50 | 2.42 ± 0.16 | 96.9 ± 5.6 |

[a] AC50 values were determined utilizing the luminescent pyruvate kinase-luciferase coupled assay and the data represents the results from three separate experiments.
[b] Max Res. (Maximum Response) is % activity that represents % activation at 57 μM of compound.

Selectivity of Chosen N,N'-diarylsulfonamide Analogues.

Figure 2:
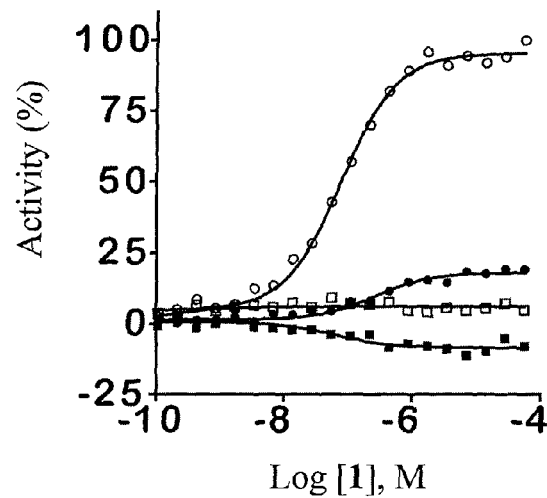
FIG. 2 illustrates the selectivity of compound 1 to PKM1, in accordance with another embodiment of the invention.

With a better understanding of the SAR for this chemotype, we next concerned ourselves with the selective activation of PKM2 versus PKM1, PKR and PKL. An appropriate tool compound aimed at further delineating the role of PKM2 as a critical contributor in the Warburg effect requires a high degree of selective activation of PKM2 relative to other PK targets with particular consideration for PKM1. Members of each chemotype were assayed versus PKM1, PKR and PKL. All analogues in the N,N'-diarylsulfonamides class were found to be inactive versus PKM1. This is consistent with the lack of allosteric regulation for the PKM1 isoform. Data varied from compound to compound, however all the compounds showed weak or no response versus PKR (<32% in both assay formats) and similar selectivity was observed for PKL (maximum response <30%, both assay formats). The selectivity for NCGC00030335 (1) is shown in FIG. 2; PKM2 (open circles), PKM1 (filled squares), PKL (open squares) and PKR (filled circles).

SAR of Substituted Thieno[3,2-b]pyrrole[3,2-d]pyridazinones and Selected Analogues.

As a standard practice, the lead substituted thieno[3,2-b]pyrrole[3,2-d]pyridazinone NCGC00031955 (66) was re-synthesized and found to possess an AC$_{50}$ value of 63±20 nM and maximum response of 122.1% in the luciferase-coupled assay and also showed good potency and efficacy in the LDH coupled reaction (AC$_{50}$ value of 326±90 nM, maximum response of 224±64%). In general, this series showed stronger activation than the analogs of 1. The SAR from the luciferase-coupled assay and mention the LDH-coupled assay for specific examples but the entire dataset for both assays is available in PubChem. Our first SAR evaluations involved changes directly to the heterocyclic core structure while retaining the standard 2-fluorobenzyl substitution from the pyridazinone ring amide (Table 4). Steric expansions of the methyl group at the 2 position of the thiophene ring were typically well tolerated [for instance the ethyl and isopropyl analogues 68 (AC$_{50}$=100±33 nM, maximum response=105.3% and 69 (AC$_{50}$=142±16 nM, maximum response=100%)]. Compound 69 did show weaker potency in the LDH assay (1.8±16 μM) but maintained an impressive max response (302%). In general, comparable potencies for these compounds were observed in the LDH assay, yet the efficacies were typically 2-3 fold higher. Removal of the methyl group resulted in a loss of potency and efficacy [see 70 (AC$_{50}$=605 nM, maximum response=93.2)]. Insertions of heteroatoms typically resulted in improved potency including SMe [see 7 (AC$_{50}$=24±8 nM, maximum response=96.3%; LDH assay showed an AC$_{50}$=110±10 nM and maximum response=259%)] and S(O)Me [see 73 (AC$_{50}$=25±6 nM, maximum response=97.9%; LDH assay showed an AC$_{50}$=190±10 nM and maximum response=211%)]. Interestingly, oxidation past the sulfoxide to the sulfone resulted in a completely inactive analogue. Carbonyls and alcohols were examined and found to retain good potencies and maximum responses [for instance 84 (AC$_{50}$=16±6 nM, maximum response=99.8%; LDH assay, AC$_{50}$=100±10 nM and maximum response=239%), 85 (AC$_{50}$=48±14 nM, maximum response=103.4%; LDH assay, AC$_{50}$=220±30 nM and maximum response=155%) and 87 (AC$_{50}$=11±3 nM, maximum response=107.6%; LDH assay, AC$_{50}$=150±30 nM and maximum response=200%)]. In stark contrast to substitutions on the 2 position of the thiophene ring, the methyl group on the pyrrole ring nitrogen was found to be an absolute necessity. Alterations from the methyl to the ethyl and isopropyl groups were ineffective and lack of substitution was found to result in an inactive analogue as well. Further, amides and sulfonamides were examined at this moiety and were not tolerated (data not shown). Addition of a methyl group to the 6 position of the pyridazinone ring was also not allowed [see 92 (AC$_{50}$>30 µM, maximum response <80%, in both assays)]. Alteration from the pyridazinone to a pyrimidinone ring system was additionally problematic [see 100 (AC$_{50}$>35 µM, maximum response <80%, in both assays)]. The necessity of the benzyl substituent was proven through examination of the corresponding phenyl analogue 101 and the n-pentyl analogue 102, both of which had marked loss of potency.

TABLE 5

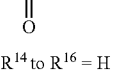

(II)

$R^{14}$ to $R^{16}$ = H

| Compound No. | $R^{11}$ | $R^{12}$ | $R^{13}$ | hPK, M2 AC$_{50}$ (µM)[a] | hPK, M2 Max. Res.[b] |
|---|---|---|---|---|---|
| 66 | Me | Me | 2-fluoro | 0.063 ± 0.02 | 122.1 ± 6.1 |
| 68 | Et | Me | 2-fluoro | 0.100 ± 0.03 | 105.3 ± 5.8 |
| 69 | iPr | Me | 2-fluoro | 0.142 ± 0.02 | 105.8 ± 6.2 |
| 70 | H | Me | 2-fluoro | 0.605 ± 0.18 | 93.2 ± 6.6 |
| 71 | OMe | Me | 2-fluoro | 0.086 ± 0.04 | 107.0 ± 8.7 |
| 72 | SMe | Me | 2-fluoro | 0.024 ± 0.01 | 96.3 ± 3.8 |
| 73 | S(O)Me | Me | 2-fluoro | 0.025 ± 0.01 | 97.9 ± 3.1 |
| 80 | NO$_2$ | Me | 2-fluoro | 0.018 ± 0.01 | 113.0 ± 3.5 |
| 81 | NHA$_c$ | Me | 2-fluoro | >25 | 58.6 ± 23.5 |
| 82 | CN | Me | 2-fluoro | 0.047 ± 0.02 | 84.1 ± 5.5 |
| 83 | COOMe | Me | 2-fluoro | 0.084 ± 0.03 | 70.4 ± 12.9 |
| 84 | CHO | Me | 2-fluoro | 0.016 ± 0.01 | 99.8 ± 6.5 |
| 85 | CH$_2$OH | Me | 2-fluoro | 0.048 ± 0.01 | 103.4 ± 7.2 |
| 86 | B(OH)$_2$ | Me | 2-fluoro | >10 | 101.3 ± 1.4 |
| 87 | COMe | Me | 2-fluoro | 0.011 ± 0 | 107.6 ± 4.9 |
| 88 | CHOH(Me) | Me | 2-fluoro | 0.136 ± 0.01 | 119.7 ± 2.6 |

TABLE 5-continued

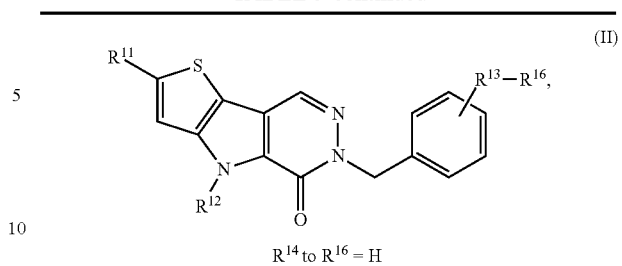

(II)

$R^{14}$ to $R^{16}$ = H

| Compound No. | $R^{11}$ | $R^{12}$ | $R^{13}$ | hPK, M2 AC$_{50}$ (µM)[a] | hPK, M2 Max. Res.[b] |
|---|---|---|---|---|---|
| 89 | Me | H | 2-fluoro | NA | 32.9 ± 3.8 |
| 90 | Me | Me | 2-fluoro | 5.9 ± 1.7 | 95.6 ± 6.3 |

[a]AC50 values were determined utilizing the luminescent pyruvate kinase-luciferase coupled assay and the data represents the results from three separate experiments.
[b]Max Res. (Maximum Response) is % activity that represents % activation at 57 µM of compound. See Methods for normalization.

TABLE 6

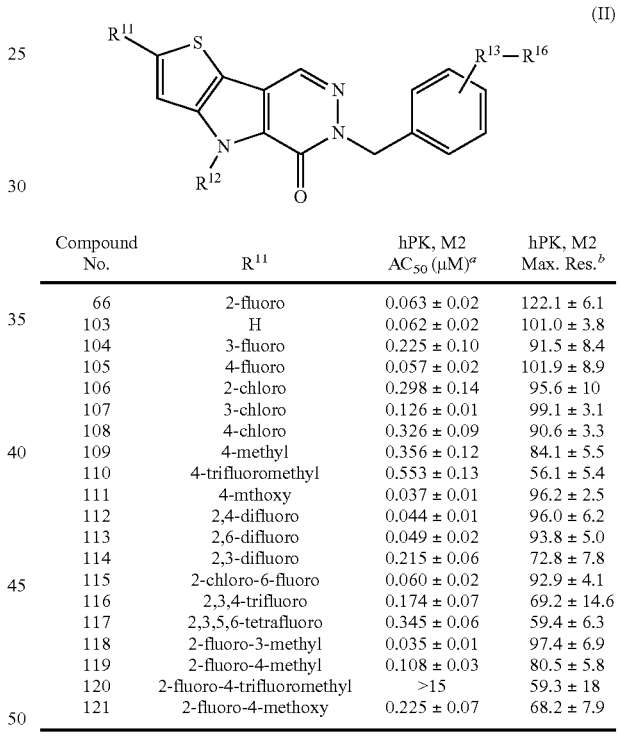

(II)

| Compound No. | $R^{11}$ | hPK, M2 AC$_{50}$ (µM)[a] | hPK, M2 Max. Res.[b] |
|---|---|---|---|
| 66 | 2-fluoro | 0.063 ± 0.02 | 122.1 ± 6.1 |
| 103 | H | 0.062 ± 0.02 | 101.0 ± 3.8 |
| 104 | 3-fluoro | 0.225 ± 0.10 | 91.5 ± 8.4 |
| 105 | 4-fluoro | 0.057 ± 0.02 | 101.9 ± 8.9 |
| 106 | 2-chloro | 0.298 ± 0.14 | 95.6 ± 10 |
| 107 | 3-chloro | 0.126 ± 0.01 | 99.1 ± 3.1 |
| 108 | 4-chloro | 0.326 ± 0.09 | 90.6 ± 3.3 |
| 109 | 4-methyl | 0.356 ± 0.12 | 84.1 ± 5.5 |
| 110 | 4-trifluoromethyl | 0.553 ± 0.13 | 56.1 ± 5.4 |
| 111 | 4-mthoxy | 0.037 ± 0.01 | 96.2 ± 2.5 |
| 112 | 2,4-difluoro | 0.044 ± 0.01 | 96.0 ± 6.2 |
| 113 | 2,6-difluoro | 0.049 ± 0.02 | 93.8 ± 5.0 |
| 114 | 2,3-difluoro | 0.215 ± 0.06 | 72.8 ± 7.8 |
| 115 | 2-chloro-6-fluoro | 0.060 ± 0.02 | 92.9 ± 4.1 |
| 116 | 2,3,4-trifluoro | 0.174 ± 0.07 | 69.2 ± 14.6 |
| 117 | 2,3,5,6-tetrafluoro | 0.345 ± 0.06 | 59.4 ± 6.3 |
| 118 | 2-fluoro-3-methyl | 0.035 ± 0.01 | 97.4 ± 6.9 |
| 119 | 2-fluoro-4-methyl | 0.108 ± 0.03 | 80.5 ± 5.8 |
| 120 | 2-fluoro-4-trifluoromethyl | >15 | 59.3 ± 18 |
| 121 | 2-fluoro-4-methoxy | 0.225 ± 0.07 | 68.2 ± 7.9 |

[a]AC50 values were determined utilizing the luminescent pyruvate kinase-luciferase coupled assay and the data represents the results from three separate experiments.
[b]Max Res. (Maximum Response) is % activity that represents % activation at 57 µM of compound. See Methods for normalization.

Additional compounds of Formula II and their properties are sets forth in Table 7. $R^{14}$ to $R^{16}$=H.

TABLE 7

| Compound No. | $R^{11}$ | $R^{12}$ | $R^{13}$ | KinaseGlo | | LDH | |
|---|---|---|---|---|---|---|---|
| | | | | hPK, M2 AC$_{50}$(µM)[a] | hPK, M2 Max. Res.[b] | hPK, M2 AC$_{50}$(µM)[a] | hPK, M2 Max. Res.[b] |
| 147 | Me | Me | 6-fluoro | 0.1834 | 83.26 | 0.2906 | 220.97 |
| 148 | S(O)Me | Me | 3-methoxy | 0.092 | 89.00 | nd | nd |
| 149 | S(O)Me | Me | 3-amino | 0.115 | 91.00 | nd | nd |

[a]Max Res. (Maximum Response) is % activity that represents % activation at 57 µM of compound.

Following the examination of the core heterocycle and selected appendages, a phenyl ring scan on the benzyl substituent was performed. The results suggest a less focused SAR for this moiety; however, selected trends did exist. For instance, bulky substituents were typically not successful at the para position of the ring [for instance 108 ($AC_{50}$=326±91 nM, maximum response=90.6%; LDH assay, $AC_{50}$=1,650±1,000 nM and maximum response=191%), 110 ($AC_{50}$=553±134 nM, maximum response=56.1%; LDH assay, $AC_{50}$=2,200±830 nM and maximum response=77%) and 120 ($AC_{50}$>15 µM, maximum response <80%, in both assays))]. Electron withdrawing substitutions were typically favored [for instance 112 ($AC_{50}$=44±11 nM, maximum response=96.0%; LDH assay, $AC_{50}$=170±30 nM and maximum response=217%), 113 ($AC_{50}$=49±18 nM, maximum response=93.8%; LDH assay, $AC_{50}$=140±10 nM and maximum response=240%)], however examples such as the 4-methoxybenzyl analogue 111 were exceptions ($AC_{50}$=37±13 nM, maximum response=96.2%; LDH assay, $AC_{50}$=230±40 nM and maximum response=258%). Substitutions that confer favorable SAR were not always additive as is demonstrated by the 2-fluoro-4-methoxy analogue 121 ($AC_{50}$=225±97 nM, maximum response=68.2%; LDH assay, $AC_{50}$=1,000±370 nM and maximum response=135±20%).

Mode of Action.

Figure 4A:
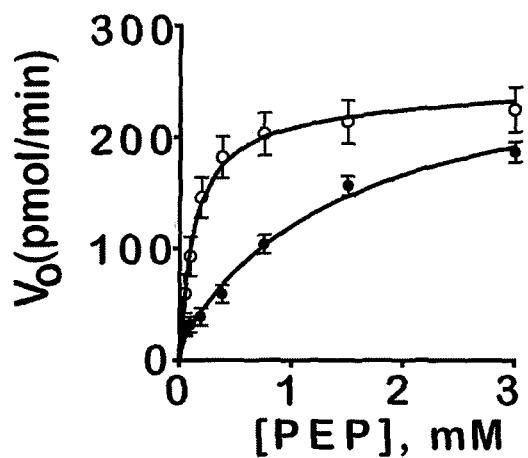
FIG. 4A illustrates that compound 66 increased the affinity of PKM2 for PEP, in accordance with another embodiment of the invention.
Figure 4B:
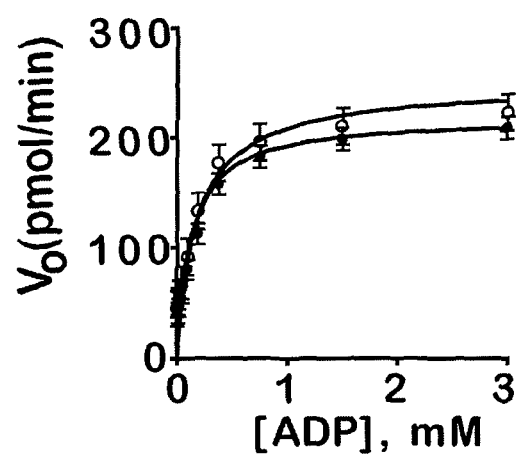
FIG. 4B illustrates the reduced effect of compound 66 on ADP kinetics.
Figure 5:
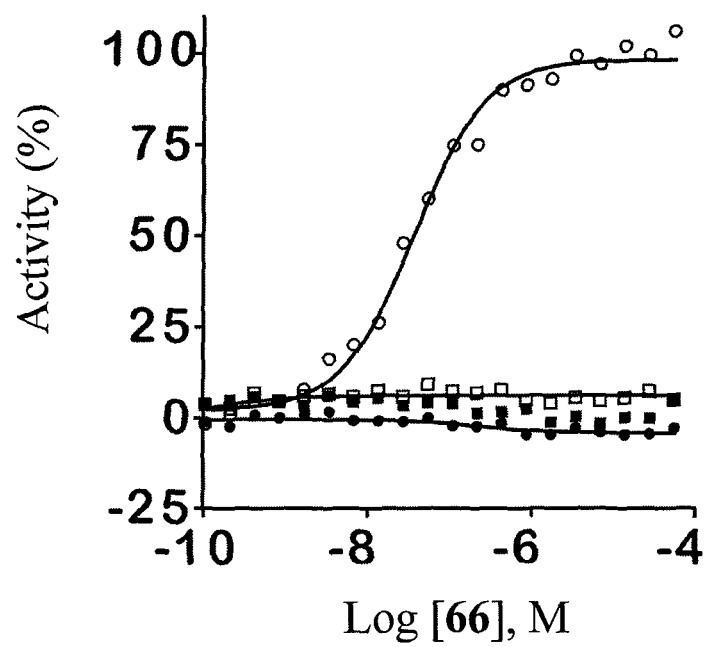
FIG. 5 illustrates the selectivity of compound 66 to PKM2, in accordance with an embodiment of the invention.

It was essential to establish the cooperative nature of these agents with the native substrates of PKM2. Given the allosteric activation of PKM2 by FBP, it was desirable to examine how the compounds affected the kinetics of PEP and ADP. In the absence of activator, hPK shows low affinity for PEP ($K_M$ ~1.5 mM). In the presence of 66 or FBP, the $K_M$ for PEP decreased to 0.13±0.04 mM or 0.1±0.02 mM for the two activators, respectively. Comparison of the ADP titration in the presence and absence of activators shows that these kinetics are not significantly affected ($K_M$ for ADP ~0.1 mM in either condition; $V_{max}$ values within 20% of each other). Thus, NCGC00031955 (the substituted thieno[3,2-b]pyrrole [3,2-d]pyridazinone 66) activates PKM2 by increasing the enzyme's affinity for PEP (FIG. 4A) and has little effect on ADP kinetics (FIG. 4B).

Selectivity of Substituted thieno[3,2-b]pyrrole[3,2-d]pyridazinones and Selected Analogues.

With the SAR surrounding this chemotype established it was essential to consider the selectivity of these compounds versus PKM1, PKR and PKL. The N,N'-diarylsulfonamide chemotype presented in the accompanying manuscript possessed a high degree of selectivity for activation of PKM2. Gratifyingly, the substituted thieno[3,2-b]pyrrole[3,2-d]pyridazinones presented here were equally selective for PKM2 activation versus PKM1. Further, all analogues examined were inactive versus PKL and PKR (see PubChem AIDs listed in Methods). FIG. 6 details the selectivity of NCGC00031955 (66) versus PKM2, PKM1, PKR and PKL.

Example 4

This example illustrates some of the properties of a compound of Formula III:

TABLE 8

| Compound No. | Formula | KinaseGlo | | LDH | |
|---|---|---|---|---|---|
| | | hPK, M2 $AC_{50}$(µM) | hPK, M2 Max. Res.[a] | hPK, M2 $AC_{50}$(µM) | hPK, M2 Max. Res.[a] |
| 150 | [structure 150] | 0.1634 | 84.04 | 0.1457 | 153.98 |

[a]Max Res. (Maximum Response) is % activity that represents % activation at 57 µM of compound.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (Ia')

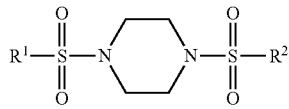

wherein $R^1$ and $R^2$ are as follows:
$R^1$ and $R^2$ are 6-(2,3-dihydro-benzo[b][1,4]dioxinyl);
$R^1$ is 4-cyanophenyl and $R^2$ is 6-(2,3-dihydro-benzo[b][1,4]dioxinyl);
$R^1$ is 4-chlorophenyl and $R^2$ is 6-(2,3-dihydro-benzo[b][1,4]dioxinyl);
$R^1$ is 4-fluorophenyl and $R^2$ is 6-(2,3-dihydro-benzo[b][1,4]dioxinyl);
$R^1$ is 3-fluorophenyl and $R^2$ is 6-(2,3-dihydro-benzo[b][1,4]dioxinyl);
$R^1$ is 2-fluorophenyl and $R^2$ is 6-(2,3-dihydro-benzo[b][1,4]dioxinyl);
$R^1$ is 2,6-difluorophenyl and $R^2$ is 6-(2,3-dihydro-benzo[b][1,4]dioxinyl);
$R^1$ is 2,4,5-trifluorophenyl and $R^2$ is 6-(2,3-dihydro-benzo[b][1,4]dioxinyl);
$R^1$ is 2,5-difluoro-3-propylphenyl and $R^2$ is 6-(2,3-dihydro-benzo [b][1,4]dioxinyl);
$R^1$ is 2,6-difluoro-3-hydroxyphenyl and $R^2$ is 6-(2,3-dihydro-benzo[b][1,4]dioxinyl);
$R^1$ is 2,4-difluorophenyl and $R^2$ is 6-(2,3-dihydro-benzo[b][1,4]dioxinyl);
$R^1$ is 3-(trifluoromethylphenyl) and $R^2$ is 6-(2,3-dihydro-benzo[b][1,4]dioxinyl);
$R^1$ is 2-pyridyl and $R^2$ is 6-(2,3-dihydro-benzo[b][1,4]dioxinyl);
$R^1$ is 2-pyridyl-1-oxide and $R^2$ is 6-(2,3-dihydro-benzo[b][1,4]dioxinyl);
$R^1$ is 2,6-difluorophenyl and $R^2$ is 2,6-difluorophenyl;
$R^1$ is 2,6-difluorophenyl and $R^2$ is 7-(3,4-dihydro-2H-benzo[b][1,4]dioxepinyl);
$R^1$ is 2,6-difluorophenyl and $R^2$ is 5-benzo[d][1,4]dioxinyl;
$R^1$ is 2,6-difluorophenyl and $R^2$ is 7-(4-methyl-3,4-dihydro-2H-pyrido[3,2-b][1,4]oxazinyl);
$R^1$ is 2,6-difluorophenyl and $R^2$ is 2-naphthalenyl;
$R^1$ is 2,6-difluorophenyl and $R^2$ is 6-(2,2-dimethylchromanyl);
$R^1$ is 2,6-difluorophenyl and $R^2$ is 5-(1-methyl-1H-indolyl); or
$R^1$ is 2,6-difluorophenyl and $R^2$ is 6-(2-methylbenzo[d]thiazolyl).

2. A compound of formula (Ia'') or a pharmaceutically acceptable salt thereof,

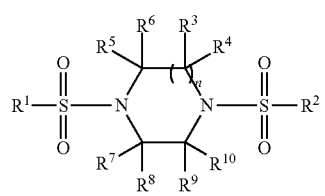

wherein n=1 to 3, $R^1$ and $R^2$ are aryl or heteroaryl, optionally substituted with one or more substituents selected from the group consisting of $C_1$-$C_{10}$ alkyl, $C_3$-$C_6$ alkylenyl, $C_2$-$C_{10}$ alkenyl, $C_2$-$C_{10}$ alkynyl, haloalkyl, $C_1$-$C_{10}$ dihaloalkyl, trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxy, alkylenedioxy, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together with the carbon atom to which they are attached, form C=O, $R^5$ and $R^7$ to $R^{10}$ are independently H, $C_1$-$C_{10}$ alkyl, or F,
$R^6$ is $C_1$-$C_{10}$ alkyl or $C_3$-$C_{10}$ cycloalkyl, or each of $R^7$ and $R^8$ and of $R^9$ and $R^{10}$, taken together with the carbon atom to which they are attached, form C=O.

3. The compound or salt of claim 2, wherein $R^1$ is selected from the group consisting of 4-methylphenyl, 2-methylphenyl, 2-fluorophenyl, 3-fluorophenyl, 4,2-difluorophenyl, 2,6-difluorophenyl, 2,4,5-trifluorophenyl, 2,6-difluoro-4-trifluoromethylphenyl, 4-chloro-2-fluoro, 3-chloro-2-fluoro, 4-trifluoromethylphenyl, 4-bromo-2-fluorophenyl, and 2-nitrophenyl.

4. A pharmaceutical composition comprising a compound or salt of claim 1 and a pharmaceutically acceptable carrier.

5. A pharmaceutical composition comprising a compound or salt of claim 2 and a pharmaceutically acceptable carrier.

6. A pharmaceutical composition comprising a compound or salt of claim 3 and a pharmaceutically acceptable carrier.

7. The compound of salt of claim 1, wherein $R^1$ and $R^2$ are 6-(2,3-dihydro-benzo[b][1,4]dioxinyl).

8. The compound of salt of claim 1, wherein $R^1$ is 4-cyanophenyl or 4-chlorophenyl, and $R^2$ is 6-(2,3-dihydro-benzo[b][1,4]dioxinyl).

9. The compound of salt of claim 1, wherein $R^1$ is 2-fluorophenyl, 3-fluoropheny, or 4-fluorophenyl and $R^2$ is 6-(2,3-dihydro-benzo[b][1,4]dioxinyl).

10. The compound of salt of claim 1, wherein $R^1$ is 2,4-difluorophenyl or 2,6-difluorophenyl and $R^2$ is 6-(2,3-dihydro-benzo [b][1,4]dioxinyl).

11. The compound of salt of claim 1, wherein $R^1$ is 2,4,5-trifluorophenyl, 2,5-difluoro-3-propylphenyl, 2,6-difluoro-3-hydroxyphenyl, or 3-(trifluoromethylphenyl) and $R^2$ is 6-(2,3-dihydro-benzo[b][1,4]dioxinyl).

12. The compound of salt of claim 1, wherein $R^1$ is 2-pyridyl or 2-pyridyl-1-oxide and $R^2$ is 6-(2,3-dihydro-benzo[b][1,4]dioxinyl).

13. The compound of salt of claim 1, wherein $R^1$ is 2,6-difluorophenyl and $R^2$ is 2,6-difluorophenyl, 7-(3,4-dihydro-2H-benzo[b][1,4]dioxepinyl), 5-benzo[d][1,4]dioxinyl, 7-(4-methyl-3,4-dihydro-2H-pyrido[3,2-b][1,4]oxazinyl), 2-naphthalenyl, 6-(2,2-dimethylchromanyl), 5-(1-methyl-1H-indolyl), or 6-(2-methylbenzo[d]thiazolyl).

14. The compound or salt of claim 2, wherein $R^1$ and $R^2$ are aryl, optionally substituted with one or more substituents selected from the group consisting of $C_1$-$C_{10}$ alkyl, $C_3$-$C_6$ alkylenyl, $C_2$-$C_{10}$ alkenyl, $C_2$-$C_{10}$ alkynyl, $C_1$-$C_{10}$ haloalkyl, dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxy, alkylenedioxy, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen.

15. The compound or salt of claim 14, wherein $R^1$ and $R^2$ are phenyl, optionally substituted with one or more substituents selected from the group consisting of $C_1$-$C_{10}$ alkyl, $C_3$-$C_6$ alkylenyl, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxy, alkylenedioxy, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen.

16. The compound or salt of claim 15, wherein n=1 and $R^3$, $R^4$, and $R^5$ are H.

17. A pharmaceutical composition comprising the compound or salt of claim 7 and a pharmaceutically acceptable carrier.

18. A pharmaceutical composition comprising the compound or salt of claim 8 and a pharmaceutically acceptable carrier.

19. A pharmaceutical composition comprising the compound or salt of claim 9 and a pharmaceutically acceptable carrier.

20. A pharmaceutical composition comprising the compound or salt of claim 10 and a pharmaceutically acceptable carrier.

21. A pharmaceutical composition comprising the compound or salt of claim 11 and a pharmaceutically acceptable carrier.

22. A pharmaceutical composition comprising the compound or salt of claim 12 and a pharmaceutically acceptable carrier.

23. A pharmaceutical composition comprising the compound or salt of claim 13 and a pharmaceutically acceptable carrier.

24. A pharmaceutical composition comprising the compound or salt of claim 14 and a pharmaceutically acceptable carrier.

25. A pharmaceutical composition comprising the compound or salt of claim 15 and a pharmaceutically acceptable carrier.

26. A pharmaceutical composition comprising the compound or salt of claim 16 and a pharmaceutically acceptable carrier.

* * * * *